(12) United States Patent
Maruo et al.

(10) Patent No.: US 10,396,399 B2
(45) Date of Patent: Aug. 27, 2019

(54) LIQUID ELECTROLYTE, AND METHOD FOR MANUFACTURING PHOSPHATE

(71) Applicant: DAIKIN INDUSTRIES, LTD., Osaka-shi, Osaka (JP)

(72) Inventors: Atsushi Maruo, Osaka (JP); Shigeaki Yamazaki, Osaka (JP); Hideo Sakata, Osaka (JP); Shinichi Kinoshita, Osaka (JP)

(73) Assignee: DAIKIN INDUSTRIES, LTD., Osaka (JP)

(*) Notice: Subject to any disclaimer, the term of this patent is extended or adjusted under 35 U.S.C. 154(b) by 182 days.

(21) Appl. No.: 15/323,761

(22) PCT Filed: Jul. 7, 2015

(86) PCT No.: PCT/JP2015/069532
§ 371 (c)(1),
(2) Date: Jan. 4, 2017

(87) PCT Pub. No.: WO2016/006607
PCT Pub. Date: Jan. 14, 2016

(65) Prior Publication Data
US 2017/0149087 A1    May 25, 2017

(30) Foreign Application Priority Data
Jul. 7, 2014  (JP) .................................. 2014-139825

(51) Int. Cl.
| | | |
|---|---|---|
| H01M 10/0567 | (2010.01) | |
| C07F 9/00 | (2006.01) | |
| C07F 9/02 | (2006.01) | |
| H01G 11/58 | (2013.01) | |
| C07F 9/09 | (2006.01) | |
| H01G 11/54 | (2013.01) | |
| H01G 11/64 | (2013.01) | |
| H01M 10/0525 | (2010.01) | |
| H01M 10/052 | (2010.01) | |
| H01M 10/0568 | (2010.01) | |
| H01M 10/0569 | (2010.01) | |
| H01G 11/60 | (2013.01) | |
| H01G 11/62 | (2013.01) | |

(52) U.S. Cl.
CPC ........... *H01M 10/0567* (2013.01); *C07F 9/00* (2013.01); *C07F 9/02* (2013.01); *C07F 9/09* (2013.01); *C07F 9/091* (2013.01); *H01G 11/54* (2013.01); *H01G 11/58* (2013.01); *H01G 11/64* (2013.01); *H01M 10/052* (2013.01); *H01M 10/0525* (2013.01); *H01G 11/60* (2013.01); *H01G 11/62* (2013.01); *H01M 10/0568* (2013.01); *H01M 10/0569* (2013.01); *H01M 2300/0025* (2013.01); *Y02E 60/13* (2013.01)

(58) Field of Classification Search
CPC ........... H01M 10/0567; H01M 10/052; H01M 10/0525; H01M 10/0568; H01M 10/0569; C07F 9/00; C07F 9/02; C07F 9/09; C07F 9/091; H01G 11/54; H01G 11/58; H01G 11/60; H01G 11/62; H01G 11/64
USPC ....................................................... 429/338
See application file for complete search history.

(56) References Cited

U.S. PATENT DOCUMENTS

| | | | |
|---|---|---|---|
| 2012/0094190 A1 | 4/2012 | Mimura et al. | |
| 2012/0183843 A1 | 7/2012 | Kawasaki et al. | |
| 2016/0365605 A1* | 12/2016 | Garsuch ............ | H01M 10/0565 |
| 2018/0237461 A1* | 8/2018 | Sakaguchi ................ | C07F 9/09 |

FOREIGN PATENT DOCUMENTS

| | | | | |
|---|---|---|---|---|
| CN | 102738503 A | 10/2012 | | |
| JP | 08-138733 A | 5/1996 | | |
| JP | 2002-231309 A | 8/2002 | | |
| JP | 2008-021560 A | 1/2008 | | |
| JP | 2011-113822 A | 6/2011 | | |
| JP | 2012-238524 A | 12/2012 | | |
| JP | 2014-022333 A | 2/2014 | | |
| JP | 2015166343 A * | 9/2015 | ............. | C07F 9/091 |
| KR | 10-2017-0112122 | * 12/2017 | ........ | H01M 10/0567 |
| WO | 2011/040447 A1 | 4/2011 | | |
| WO | 2013/002186 A1 | 1/2013 | | |
| WO | WO-2017111096 A1 * | 6/2017 | ........ | H01M 10/0587 |

OTHER PUBLICATIONS

Machine translation of JP 2014-022333 (no date).*
Machine translation of JP H08-138733 (no date).*
Machine translation of WO 2013/002186 (no date).*
Machine translation of JP2015-166343 (no date).*
International Preliminary Report on Patentability issued from the International Bureau in counterpart International Application No. PCT/JP2015/069532, dated Jan. 10, 2017.
Communication dated Mar. 1, 2018 from the European Patent Office in counterpart application No. 15819618.8.
M. I. Kabachnik et al., "New Homogeneous Catalysts for Phosphorylation of Polyfluoroalcohols by Phosphoryl Chlorides," Russian Journal of Applied Chemistry, 1995, pp. 1757-1762, vol. 68, No. 12, Part 2.
International Search Report of PCT/JP2015/069532 dated Oct. 13, 2015.
Communication dated Dec. 14, 2017 from the European Patent Office in counterpart application No. 15819618.8.
Communication dated Nov. 9, 2018, from European Patent Office in counterpart application No. 18192910.0.

* cited by examiner

*Primary Examiner* — Amanda C. Walke
(74) *Attorney, Agent, or Firm* — Sughrue Mion, PLLC

(57) ABSTRACT

An electrolyte solution capable of providing electrochemical devices whose internal resistance is less likely to increase even after repeated charge and discharge and whose cycle capacity retention ratio is high. The electrolyte solution contains a solvent, an electrolyte salt, and a phosphate in an amount of 0.001 to 15 mass % relative to the solvent and represented by the formula (1): $(R^{11}O)(R^{12}O)PO_2M$, where $R^{11}$, $R^{12}$ and M are as defined herein.

9 Claims, No Drawings

LIQUID ELECTROLYTE, AND METHOD FOR MANUFACTURING PHOSPHATE

CROSS REFERENCE TO RELATED APPLICATIONS

This application is a National Stage of International Application No. PCT/JP2015/069532 filed Jul. 7, 2015, claiming priority based on Japanese Patent Application No. 2014-139825 filed Jul. 7, 2014, the contents of all of which are incorporated herein by reference in their entirety.

TECHNICAL FIELD

The present invention relates to electrolyte solutions, and electrochemical devices, secondary batteries, and modules including the electrolyte solutions. The present invention also relates to a novel method for manufacturing phosphates.

BACKGROUND ART

Known electrolyte solutions used in electrochemical devices such as lithium ion secondary batteries include electrolyte solutions containing a fluorinated organophosphate.

For example, in order to provide a lithium secondary battery having excellent charge and discharge cycle characteristics as a result of restraining the reaction between the negative electrode and a non-aqueous electrolyte solution when charged and discharged, Patent Literature 1 discloses a lithium secondary battery including a positive electrode, a negative electrode, and a non-aqueous electrolyte solution containing a solute dissolved in a non-aqueous solvent, wherein the negative electrode is formed from a negative electrode material containing aluminum and the non-aqueous solvent is mixed with at least one selected from the group consisting of fluorinated organophosphates and fluorinated organophosphites.

Patent Literature 2 discloses a non-aqueous electrolyte battery including a positive electrode that contains a lithium-containing polyanionic metal complex compound wherein the non-aqueous electrolyte has incombustibility while having excellent high-rate discharge performance and cycle performance. The non-aqueous electrolyte battery is a non-aqueous electrolyte secondary battery and characteristically contains one or more fluorinated organophosphate compounds in which the end structure of an alkyl group is represented by $CF_3$ and one or more fluorinated organophosphate compounds in which the end structure of an alkyl group is represented by $CF_2H$.

Patent Literature 3 discloses an incombustible non-aqueous electrolyte solution having high solubility of an electrolyte salt, a large discharge capacity, and excellent charge and discharge cycle characteristics, and containing an organic solvent (II) which contains 0.5 to 30 vol % of a fluorine-containing organophosphate (I) represented by $O=P(CH_2Rf)_3$ and an electrolyte salt (III).

Patent Literature 4 discloses a secondary battery which can work for a long time, wherein an electrolyte solution used therein includes a liquid medium which is less likely to generate carbon dioxide at a concentration of 10 to 80 vol %, and discloses fluorinated organophosphate compounds as examples of the liquid medium which is less likely to generate carbon dioxide.

Patent Literature 5 discloses a non-aqueous electrolyte solution for non-aqueous secondary batteries which has high ion conductivity and is capable of maintaining the performance for a long time, and contains $LiPF_6$ as an electrolyte, a cyclic carbonate as a solvent, and a fluorine-containing organophosphate represented by $O=P(CH_2Rf)_3$ in an amount 0.1 to 2 times (mole ratio) larger than the amount of $LiPF_6$.

CITATION LIST

Patent Literature

Patent Literature 1: JP 2002-231309 A
Patent Literature 2: JP 2011-113822 A
Patent Literature 3: JP 2008-21560 A
Patent Literature 4: WO 2011/040447
Patent Literature 5: JP 2012-238524 A

Non-Patent Literature

Non-Patent Literature 1: M. I. Kabachnik, and two others, "NEW HOMOGENEOUS CATALYSTS FOR PHOSPHORYLATION OF POLYFLUOROALCOHOLS BY PHOSPHORYL CHLORIDES", Russian Journal of Applied Chemistry (English version), 1995, Vol. 68, No. 12, Part 2, p. 1760-1762

SUMMARY OF INVENTION

Technical Problem

Improvement of the output characteristics of electrochemical devices such as lithium ion secondary batteries requires reduction in the internal resistance of the electrochemical devices. However, electrochemical devices tend to have a higher internal resistance after repeated charge and discharge.

The present invention then aims to provide a novel electrolyte solution capable of providing electrochemical devices whose internal resistance is less likely to increase even after repeated charge and discharge and whose cycle capacity retention ratio is high.

The present invention also aims to provide a method for manufacturing a phosphate having a low residual alkali concentration and a high purity in high yield.

Solution to Problem

The inventors have performed various studies for solving the above problems to find that an electrolyte solution containing a specific phosphate at a specific composition enables production of electrochemical devices such as secondary batteries having excellent storage characteristics and cycle characteristics, thereby completing the present invention.

Specifically, the present invention relates to an electrolyte solution including a solvent; an electrolyte salt; and a phosphate in an amount of 0.001 to 15 mass % relative to the solvent, the phosphate being represented by the following formula (1):

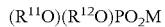

wherein $R^{11}$ and $R^{12}$ may be the same as or different from each other, and are individually a C1-C11 linear or branched alkyl group, a C2-C11 linear or branched alkenyl group, a C2-C11 linear or branched alkynyl group, a C3-C7 cycloalkyl group, a C3-C7 cycloalkenyl group, or a C4-C8 alkylsilyl group, the alkyl group, the alkenyl group, the alkynyl group, the cycloalkyl group, the cycloalkenyl group, or the alkylsilyl group may have a halogen atom which substitutes for a hydrogen atom bonding to a carbon atom, may have a cyclic structure, and may have an ether bond or a thioether bond; and M is at least one selected from the group consisting of Li, Na, K, and Cs.

Preferably, $R^{11}$ and $R^{12}$ may be the same as or different from each other, and are represented by $R^{13}CH_2$—, where $R^{13}$ is a hydrogen atom, a C1-C10 linear or branched alkyl group, a C1-C10 linear or branched alkenyl group, a C1-C10 linear or branched alkynyl group, a C3-C6 cycloalkyl group, a C3-C6 cycloalkenyl group, or a C4-C7 alkylsilyl group, the alkyl group, the alkenyl group, the alkynyl group, the cycloalkyl group, the cycloalkenyl group, or the alkylsilyl group may have a halogen atom which substitutes for a hydrogen atom bonding to a carbon atom, may have a cyclic structure, and may have an ether bond or a thioether bond.

Preferably, $R^{11}$ and $R^{12}$ may be the same as or different from each other, and are represented by $Rf^{11}CH_2$—, where $Rf^{11}$ is a C1-C10 linear or branched fluoroalkyl group; and M is Li.

Preferably, $R^{11}$ is represented by $Rf^{12}CH_2$—, where $Rf^{12}$ is a C1-C10 linear or branched fluoroalkyl group; $R^{12}$ is represented by $Rf^{13}CH_2$—, where $Rf^{13}$ is a C1-C10 linear or branched fluoroalkyl group; $Rf^{12}$ and $Rf^{13}$ are different fluoroalkyl groups; and M is Li.

The solvent preferably contains at least one selected from the group consisting of non-fluorinated saturated cyclic carbonates, fluorinated saturated cyclic carbonates, non-fluorinated acyclic carbonates, and fluorinated acyclic carbonates.

The electrolyte salt is preferably at least one lithium salt selected from the group consisting of $LiPF_6$, $LiBF_4$, $LiSO_3CF_3$, $LiN(SO_2CF_3)_2$, $LiN(SO_2C_2F_5)_2$, lithium difluoro(oxalato)borate, lithium bis(oxalato)borate, and a salt represented by $LiPF_a(C_nF_{2n+1})_{6-a}$, where a is an integer of 0 to 5 and n is an integer of 1 to 6.

The present invention also relates to an electrochemical device including the above electrolyte solution.

The present invention also relates to a secondary battery including the above electrolyte solution.

The present invention also relates to a module including the above electrochemical device or the above secondary battery.

The present invention also relates to a method for manufacturing a phosphate, including:

reacting, in a solvent, an organophosphate represented by the following formula (2) and an alkali metal hydroxide in an amount of 1.01 mole equivalents or more relative to the organophosphate to provide a composition containing a phosphate represented by the following formula (1), the alkali metal hydroxide, and the solvent; and adding hydrogen fluoride to the composition to neutralize the composition and to precipitate an alkali metal fluoride, thereby providing a composition containing the precipitated alkali metal fluoride, the phosphate represented by the formula (1), and the solvent, the formula (1) being $(R^{11}O)(R^{12}O)PO_2M$, where $R^{11}$ and $R^{12}$ may be the same as or different from each other, and are individually a C1-C11 linear or branched alkyl group, a C2-C11 linear or branched alkenyl group, a C2-C11 linear or branched alkynyl group, a C3-C7 cycloalkyl group, or a C3-C7 cycloalkenyl group, the alkyl group, the alkenyl group, the alkynyl group, the cycloalkyl group, or the cycloalkenyl group may have a halogen atom which substitutes for a hydrogen atom bonding to a carbon atom, may have a cyclic structure, and may have an ether bond or a thioether bond; and M is at least one selected from the group consisting of Li, Na, K, and Cs, and the formula (2) being $(R^{21}O)(R^{22}O)(R^{23}O)PO$, where $R^{21}$, $R^{22}$, and $R^{23}$ may be the same as or different from each other, and are individually a C1-C11 linear or branched alkyl group, a C2-C11 linear or branched alkenyl group, a C2-C11 linear or branched alkynyl group, a C3-C7 cycloalkyl group, or a C3-C7 cycloalkenyl group, the alkyl group, the alkenyl group, the alkynyl group, the cycloalkyl group, or the cycloalkenyl group may have a halogen atom which substitutes for a hydrogen atom bonding to a carbon atom, may have a cyclic structure, and may have an ether bond or a thioether bond.

In the above manufacturing method, preferably, the alkali metal hydroxide is lithium hydroxide, the alkali metal fluoride is lithium fluoride, M in each of the formulas (1) and (2) is Li, $R^{11}$ and $R^{12}$ may be the same as or different from each other, and are represented by $R^{13}CH_2$—, where $R^{13}$ is a hydrogen atom, a C1-C10 linear or branched alkyl group, a C1-C10 linear or branched alkenyl group, a C1-C10 linear or branched alkynyl group, a C3-C6 cycloalkyl group, or a C3-C6 cycloalkenyl group, the alkyl group, the alkenyl group, the alkynyl group, the cycloalkyl group, or the cycloalkenyl group may have a halogen atom which substitutes for a hydrogen atom bonding to a carbon atom, may have a cyclic structure, and may have an ether bond or a thioether bond, and $R^{21}$, $R^{22}$, and $R^{23}$ may be the same as or different from each other, and are represented by $R^{24}CH_2$—, where $R^{24}$ is a hydrogen atom, a C1-C10 linear or branched alkyl group, a C1-C10 linear or branched alkenyl group, a C1-C10 linear or branched alkynyl group, a C3-C6 cycloalkyl group, or a C3-C6 cycloalkenyl group, the alkyl group, the alkenyl group, the alkynyl group, the cycloalkyl group, or the cycloalkenyl group may have a halogen atom which substitutes for a hydrogen atom bonding to a carbon atom, may have a cyclic structure, and may have an ether bond or a thioether bond.

In the above manufacturing method, preferably, the alkali metal hydroxide is lithium hydroxide, the alkali metal fluoride is lithium fluoride, M in each of the formulas (1) and (2) is Li, $R^{11}$ and $R^{12}$ may be the same as or different from each other, and are represented by $Rf^{11}CH_2$—, where $Rf^{11}$ is a C1-C10 linear or branched fluoroalkyl group, and $R^{21}$, $R^{22}$, and $R^{23}$ may be the same as or different from each other, and are represented by $Rf^{21}CH_2$—, where $Rf^{21}$ is a C1-C10 linear or branched fluoroalkyl group.

In the above manufacturing method, preferably, the alkali metal hydroxide is lithium hydroxide, the alkali metal fluoride is lithium fluoride, M in each of the formulas (1) and (2) is Li, $R^{11}$ is represented by $Rf^{12}CH_2$—, where $Rf^{12}$ is a C1-C10 linear or branched fluoroalkyl group, $R^{12}$ is represented by $Rf^{13}CH_2$—, where $Rf^{13}$ is a C1-C10 linear or branched fluoroalkyl group, $Rf^{12}$ and $Rf^{13}$ are different fluoroalkyl groups, $R^{21}$ is represented by $Rf^{22}CH_2$—, where $Rf^{22}$ is a C1-C10 linear or branched fluoroalkyl group, $R^{22}$ is represented by $Rf^{23}CH_2$—, where $Rf^{23}$ is a C1-C10 linear or branched fluoroalkyl group, and $R^{23}$ is represented by $Rf^{24}CH_2$—, where $Rf^{24}$ is a C1-C10 linear or branched fluoroalkyl group.

The above manufacturing method preferably further includes filtering out the precipitated alkali metal fluoride from the composition containing the precipitated alkali metal fluoride, the phosphate represented by the formula (1), and the solvent to collect, as a filtrate, a composition containing the phosphate represented by the formula (1) and the solvent.

The above manufacturing method preferably further includes providing the phosphate represented by the formula (1) in the dry state from the collected filtrate.

The hydrogen fluoride is preferably at least one selected from the group consisting of anhydrous hydrogen fluoride and hydrofluoric acid.

The alkali metal hydroxide is preferably in an amount of 1.05 mole equivalents or more relative to the organophosphate represented by the formula (2).

The phosphate represented by the formula (1) preferably has a fluoride ion concentration of 1 mass % or less.

The solvent is preferably water.

Advantageous Effects of Invention

Utilizing the electrolyte solution of the present invention enables production of electrochemical devices whose internal resistance is less likely to increase even after repeated charge and discharge and whose cycle capacity retention ratio is high.

The manufacturing method of the present invention enables production of a phosphate having a low residual alkali concentration and a high purity in high yield.

DESCRIPTION OF EMBODIMENTS

The present invention will be specifically described hereinbelow.

The electrolyte solution of the present invention contains a phosphate represented by the formula (1):

$$(R^{11}O)(R^{12}O)PO_2M$$

wherein $R^{11}$ and $R^{12}$ may be the same as or different from each other, and are individually a C1-C11 linear or branched alkyl group, a C2-C11 linear or branched alkenyl group, a C2-C11 linear or branched alkynyl group, a C3-C7 cycloalkyl group, a C3-C7 cycloalkenyl group, or a C4-C8 alkylsilyl group, the alkyl group, the alkenyl group, the alkynyl group, the cycloalkyl group, the cycloalkenyl group, or the alkylsilyl group may have a halogen atom which substitutes for a hydrogen atom bonding to a carbon atom, may have a cyclic structure, and may have an ether bond or a thioether bond; and M is at least one selected from the group consisting of Li, Na, K, and Cs.

$R^{11}$ and $R^{12}$ are preferably individually a C1-C11 linear or branched alkyl group. The alkyl group preferably has a halogen atom, more preferably a fluorine atom, which substitutes for a hydrogen atom bonding to a carbon atom. The alkyl group preferably does not have a cyclic structure, an ether bond, or a thioether bond. The carbon number of the alkyl group is preferably 7 or smaller, while preferably 2 or greater, more preferably 3 or greater.

$R^{11}$ and $R^{12}$ may be the same as or different from each other, and are preferably represented by $R^{13}CH_2$—, where $R^{13}$ is a hydrogen atom, a C1-C10 linear or branched alkyl group, a C1-C10 linear or branched alkenyl group, a C1-C10 linear or branched alkynyl group, a C3-C6 cycloalkyl group, a C3-C6 cycloalkenyl group, or a C4-C7 alkylsilyl group, the alkyl group, the alkenyl group, the alkynyl group, the cycloalkyl group, the cycloalkenyl group, or the alkylsilyl group may have a halogen atom which substitutes for a hydrogen atom bonding to a carbon atom, may have a cyclic structure, and may have an ether bond or a thioether bond.

$R^{13}$ is preferably a C1-C10 linear or branched alkyl group. The alkyl group preferably has a halogen atom, more preferably a fluorine atom, which substitutes for a hydrogen atom bonding to a carbon atom. The alkyl group preferably does not have a cyclic structure, an ether bond, or a thioether bond. The carbon number of the alkyl group is preferably 6 or smaller while preferably 2 or greater.

M is at least one selected from the group consisting of Li, Na, K, and Cs, preferably Li.

In order to provide electrochemical devices whose internal resistance is much less likely to increase even after repeated charge and discharge and whose cycle capacity retention ratio is higher, preferably, $R^{11}$ and $R^{12}$ are the same as or different from each other and are represented by $Rf^{11}CH_2$— (where $Rf^{11}$ is a C1-C10 linear or branched fluoroalkyl group), and M is Li.

In other words, the phosphate represented by the formula (1) is preferably a phosphate (fluoroalkyl phosphate monolithium salt) represented by the formula (1-1):

$$(Rf^{11}CH_2O)_2PO_2Li$$

wherein $Rf^{11}$ is a C1-C10 linear or branched fluoroalkyl group.

$R^{11}$ and $R^{12}$ are preferably the same as each other. Two $Rf^{11}$s are preferably the same as each other.

The fluoroalkyl group is a group in which at least one hydrogen atom in the alkyl group is replaced by a fluorine atom.

$Rf^{11}$, if having a carbon number of 2 or greater, may contain an oxygen atom between carbon atoms to form, for example, a $CF_3$—O—$CF_2$— structure unless oxygen atoms are adjacent to each other. Still, it preferably contains no oxygen atom between carbon atoms.

The carbon number of $Rf^{11}$ is more preferably 6 or smaller, while preferably 2 or greater.

Examples of $Rf^{11}$ include $CF_3$—, $HCF_2$—, $FCH_2$—, $CF_3$—$CF_2$—, $HCF_2$—$CF_2$—, $FCH_2$—$CF_2$—, $CF_3$—$CH_2$—, $HCF_2$—$CH_2$—, $FCH_2$—$CH_2$—, $CH_3$—$CF_2$—, $CF_3$—$CF_2$—$CF_2$—, $FCH_2CF_2CF_2$—, $HCF_2CF_2CF_2$—, $CF_3$—$CF_2$—$CH_2$—, $CF_3$—$CH_2$—$CF_2$—, $CF_3$—$CH(CF_3)$—, $HCF_2$—$CH(CF_3)$—, $FCH_2$—$CH(CF_3)$—, $CF_3$—$CF(CH_3)$—, $HCF_2$—$CF(CH_3)$—, $FCH_2$—$CF(CH_3)$—, $CH_3CF_2CF_2$—, $CF_3CF_2CF_2$—, $CF_3CF_2CF_2CH_2$—, $CF_3CF_2CH_2CF_2$—, and $CF_3CH_2CF_2CF_2$—.

$Rf^{11}$ is preferably at least one selected from the group consisting of $FCH_2$—, $CF_3$—, $HCF_2$—, $HCF_2$—$CF_2$—, and $CF_3$—$CF_2$—, more preferably at least one selected from the group consisting of $CF_3$—, $HCF_2$—, $HCF_2$—$CF_2$—, and $CF_3$—$CF_2$—.

Specific examples of the phosphate represented by the formula (1) include bis-2-fluoroethyl phosphate monolithium salt $((CFH_2CH_2O)_2PO_2Li)$, bis-2,2,2-trifluoroethyl phosphate monolithium salt $((CF_3CH_2O)_2PO_2Li)$, bis-2-H-2,2-difluoroethyl phosphate monolithium salt $((HCF_2CH_2O)_2PO_2Li)$, bis-3-H-2,2,3,3-tetrafluoropropyl phosphate monolithium salt $((HCF_2CF_2CH_2O)_2PO_2Li)$, and $(CF_3CF_2CH_2O)_2PO_2Li$. For good effects of improving the battery characteristics, such as storage stability and cycle characteristics, preferred is at least one selected from the group consisting of $(CF_3CH_2O)_2PO_2Li$, $(HCF_2CH_2O)_2PO_2Li$, $(HCF_2CF_2CH_2O)_2PO_2Li$, and $(CF_3CF_2CH_2O)_2PO_2Li$.

The phosphate represented by the formula (1) to be used may satisfy that $R^{11}$ is represented by $Rf^{12}CH_2$— (where $Rf^{12}$ is a C1-C10 linear or branched fluoroalkyl group); $R^{12}$ is represented by $Rf^{13}CH_2$— (where $Rf^{13}$ is a C1-C10 linear or branched fluoroalkyl group), $Rf^{12}$ and $Rf^{13}$ are different fluoroalkyl groups; and M is Li.

$Rf^{12}$ and $Rf^{13}$, if having a carbon number of 2 or greater, may contain an oxygen atom between carbon atoms to form, for example, a $CF_3$—O—$CF_2$— structure unless oxygen atoms are adjacent to each other. Still, they preferably contain no oxygen atom between carbon atoms.

The carbon numbers of $Rf^{12}$ and $Rf^{13}$ are individually more preferably 6 or smaller while preferably 2 or greater.

Examples of $Rf^{12}$ and $Rf^{13}$ include $CF_3$—, $HCF_2$—, $FCH_2$—, $CF_3$—$CF_2$—, $HCF_2$—$CF_2$—, $FCH_2$—$CF_2$—, $CF_3$—$CH_2$—, $HCF_2$—$CH_2$—, $FCH_2$—$CH_2$—, $CH_3$—$CF_2$—, $CF_3$—$CF_2$—$CF_2$—, $FCH_2CF_2CF_2$—, $HCF_2CF_2CF_2$—, $CF_3$—$CF_2$—$CH_2$—, $CF_3$—$CH_2$—$CF_2$—, $CF_3$—$CH(CF_3)$—, $HCF_2$—$CH(CF_3)$—, $FCH_2$—$CH(CF_3)$—, $CF_3$—$CF(CH_3)$—, $HCF_2$—$CF(CH_3)$—, $FCH_2$—$CF(CH_3)$—, $CH_3CF_2CF_2$—, $CF_3CF_2CF_2CF_2$—, $CF_3CF_2CF_2CH_2$—, $CF_3CF_2CH_2CF_2$—, and $CF_3CH_2CF_2CF_2$—.

$Rf^{12}$ and $Rf^{13}$ are preferably individually at least one selected from the group consisting of $FCH_2$—, $CF_3$—, $HCF_2$—, $HCF_2$—$CF_2$—, and $CF_3$—$CF_2$—, more preferably at least one selected from the group consisting of $CF_3$—, $HCF_2$—, $HCF_2$—$CF_2$—, and $CF_3$—$CF_2$—.

$Rf^{12}$ and $Rf^{13}$ are different fluoroalkyl groups. Preferred examples of the combination thereof are as follows: $Rf^{12}$ is $CF_3$— or $CF_3$—$CF_2$ and $Rf^{13}$ is $CF_3$—, $HCF_2$—, or $HCF_2$—$CH_2$.

The electrolyte solution of the present invention contains 0.001 to 15 mass % of the phosphate represented by the formula (1) relative to the solvent. The amount of the phosphate represented by the formula (1) is preferably 0.005 mass % or more, more preferably 0.05 mass % or more, while preferably 10 mass % or less, more preferably 5 mass % or less.

The electrolyte solution of the present invention contains a solvent. The solvent is preferably a non-aqueous solvent and the electrolyte solution of the present invention is preferably a non-aqueous electrolyte solution.

The solvent preferably contains at least one selected from the group consisting of non-fluorinated saturated cyclic carbonates, fluorinated saturated cyclic carbonates, non-fluorinated acyclic carbonates, and fluorinated acyclic carbonates.

Examples of the non-fluorinated saturated cyclic carbonates include ethylene carbonate (EC), propylene carbonate (PC), and butylene carbonate.

In order to achieve a high permittivity and a suitable viscosity, the non-fluorinated saturated cyclic carbonate is preferably at least one compound selected from the group consisting of ethylene carbonate, propylene carbonate, and butylene carbonate.

The non-fluorinated saturated cyclic carbonate may include one of the above compounds or may include two or more thereof in combination.

The fluorinated saturated cyclic carbonate is a saturated cyclic carbonate with a fluorine atom attached thereto. Specific examples thereof include a fluorinated saturated cyclic carbonate (A) represented by the following formula (A):

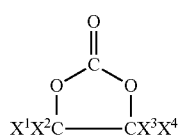

(A)

wherein $X^1$ to $X^4$ may be the same as or different from each other, and are individually a fluorinated alkyl group which may optionally have —H, —$CH_3$, —F, or an ether bond, or a fluorinated alkoxy group which may optionally have an ether bond; at least one of $X^1$ to $X^4$ is a fluorinated alkyl group which may optionally have —F or an ether bond, or a fluorinated alkoxy group which may optionally have an ether bond.

If the electrolyte solution of the present invention contains a fluorinated saturated cyclic carbonate (A) and is applied to a lithium ion secondary battery, a stable film is formed on the negative electrode so that side reactions of the electrolyte solution on the negative electrode may sufficiently be suppressed. As a result, significantly stable, excellent charge and discharge characteristics can be achieved.

The term "ether bond" herein means a bond represented by —O—.

In order to achieve a good permittivity and oxidation resistance, one or two of $X^1$ to $X^4$ in the formula (A) is/are preferably a fluorinated alkyl group which may optionally have —F or an ether bond or a fluorinated alkoxy group which may optionally have an ether bond.

In anticipation of a decrease in the viscosity at low temperatures, an increase in the flash point, and improvement in the solubility of the electrolyte salt, $X^1$ to $X^4$ in the formula (A) are preferably individually —H, —F, a fluorinated alkyl group (a), a fluorinated alkyl group (b) having an ether bond, or a fluorinated alkoxy group (c).

The fluorinated alkyl group (a) is an alkyl group in which at least one hydrogen atom is replaced by a fluorine atom. The fluorinated alkyl group (a) preferably has a carbon number of 1 to 20, more preferably 2 to 17, still more preferably 2 to 7, particularly preferably 2 to 5.

If the carbon number is too large, the low-temperature characteristics may be poor and the solubility of the electrolyte salt may be low. If the carbon number is too small, the solubility of the electrolyte salt may be low, the discharge efficiency may be low, and the viscosity may be high, for example.

Examples of the fluorinated alkyl group (a) which has a carbon number of 1 include $CFH_2$—, $CF_2H$—, and $CF_3$—.

In order to achieve a good solubility of the electrolyte salt, preferred examples of the fluorinated alkyl group (a) which has a carbon number of 2 or greater include fluorinated alkyl groups represented by the following formula (a-1):

(a-1)

wherein $R^1$ is an alkyl group which may optionally have a fluorine atom and which has a carbon number of 1 or greater; $R^2$ is a C1-C3 alkylene group which may optionally have a fluorine atom; and at least one of $R^1$ and $R^2$ has a fluorine atom.

$R^1$ and $R^2$ each may further have an atom other than the carbon atom, hydrogen atom, and fluorine atom.

$R^1$ is an alkyl group which may optionally have a fluorine atom and which has a carbon number of 1 or greater. $R^1$ is preferably a C1-C16 linear or branched alkyl group. The carbon number of $R^1$ is more preferably 1 to 6, still more preferably 1 to 3.

Specifically, for example, $CH_3$—, $CH_3CH_2$—, $CH_3CH_2CH_2$—, $CH_3CH_2CH_2CH_2$—, and the groups represented by the following formulas:

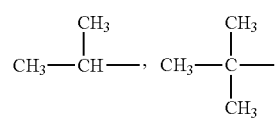

may be mentioned as linear or branched alkyl groups for $R^1$.

If $R^1$ is a linear alkyl group having a fluorine atom, examples thereof include $CF_3$—, $CF_3CH_2$—, $CF_3CF_2$—, $CF_3CH_2CH_2$—, $CF_3CF_2CH_2$—, $CF_3CF_2CF_2$—, $CF_3CH_2CF_2$—, $CF_3CH_2CH_2CH_2$—, $CF_3CF_2CH_2CH_2$—, $CF_3CH_2CF_2CH_2$—, $CF_3CF_2CF_2CH_2$—, $CF_3CF_2CH_2CF_2$—, $CF_3CH_2CH_2CH_2CH_2$—, $CF_3CF_2CH_2CH_2CH_2$—, $CF_3CH_2CF_2CH_2CH_2$—, $CF_3CF_2CF_2CH_2CH_2$—, $CF_3CF_2CF_2CF_2CH_2$—, $CF_3CF_2CH_2CH_2CH_2CH_2$—, $CF_3CF_2CF_2CF_2CH_2CH_2$—, $CF_3CF_2CH_2CF_2CH_2CH_2$—, $HCF_2$—, $HCF_2CH_2$—, $HCF_2CF_2$—, $HCF_2CH_2CH_2$—, $HCF_2CF_2CH_2$—, $HCF_2CH_2CF_2$—, $HCF_2CF_2CH_2CH_2$—, $HCF_2CH_2CF_2CH_2$—, $HCF_2CF_2CF_2CF_2$—, $HCF_2CF_2CH_2CH_2CH_2$—, $HCF_2CH_2CF_2CH_2CH_2$—, $HCF_2CF_2CF_2CF_2CH_2$—, $HCF_2CF_2CF_2CH_2CH_2$—, $FCH_2$—, $FCH_2CH_2$—, $FCH_2CF_2$—, $FCH_2CF_2CH_2$—, $FCH_2CF_2CF_2$—, $CH_3CF_2CH_2$—, $CH_3CF_2CF_2$—, $CH_3CH_2CH_2$—, $CH_3CF_2CH_2CF_2$—, $CH_3CF_2CF_2CF_2$—, $CH_3CH_2CF_2CF_2$—, $CH_3CF_2CH_2CF_2CH_2$—, $CH_3CF_2CF_2CF_2CH_2$—, $CH_3CF_2CH_2CH_2$—, $CH_3CH_2CF_2CF_2CH_2$—, $CH_3CF_2CH_2CF_2CH_2CH_2$—, $HCFClCF_2CH_2$—, $HCF_2CFClCH_2$—, $HCF_2CFClCF_2CFClCH_2$—, and $HCFClCF_2CFClCF_2CH_2$—.

If $R^1$ is a branched alkyl group having a fluorine atom, those represented by the following formulas:

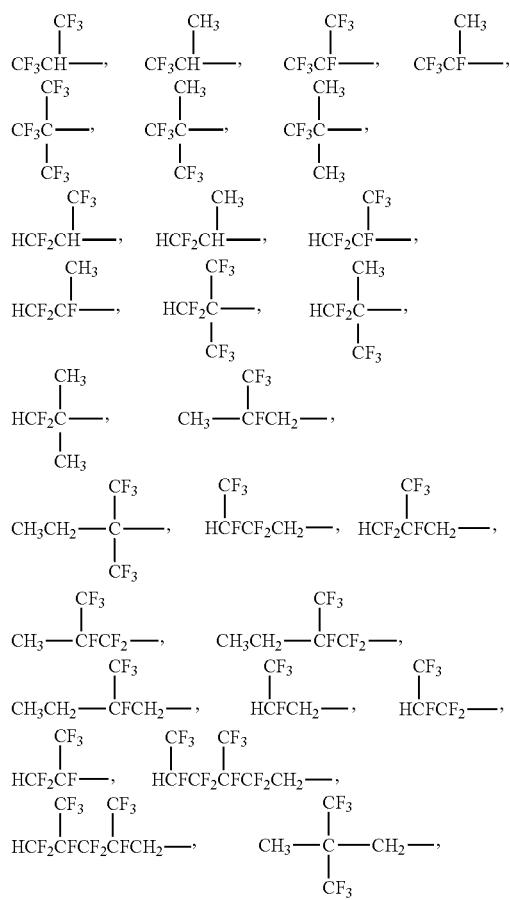

may be preferably mentioned. If the group has a branch represented by —$CH_3$ or —$CF_3$, for example, the viscosity is likely to be high. Thus, the number of such branches is more preferably small (one) or zero.

$R^2$ is a C1-C3 alkylene group which may optionally have a fluorine atom. $R^2$ may be a linear or branched group. Examples of a minimum structural unit constituting such a linear or branched alkylene group are shown below. $R^2$ is constituted by one or combination of these units.

(i) Linear minimum structural units
—$CH_2$—, —$CHF$—, —$CF_2$—, —$CHCl$—, —$CFCl$—, —$CCl_2$—

(ii) Branched minimum structural units

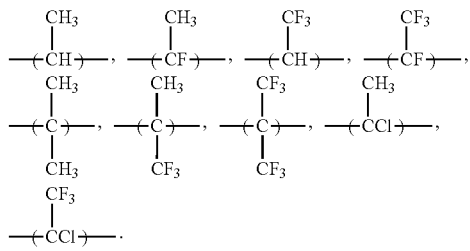

Preferred among these exemplified units are Cl-free structural units because such units are not dehydrochlorinated by a base, and thus are more stable.

If $R^2$ is a linear group, the group consists only of the above linear minimum structural unit, preferably —$CH_2$—, —$CH_2CH_2$—, or —$CF_2$—. In order to further improve the solubility of the electrolyte salt, —$CH_2$— or —$CH_2CH_2$— is more preferred.

If $R^2$ is a branched group, the group includes at least one of the above branched minimum structural units. Preferred examples thereof include those represented by the formula: —($CX^aX^b$)— (wherein $X^a$ is H, F, $CH_3$, or $CF_3$; $X^b$ is $CH_3$ or $CF_3$; if $X^b$ is $CF_3$, $X^a$ is H or $CH_3$). Such groups can further improve the solubility of the electrolyte salt.

For example, $CF_3CF_2$—, $HCF_2CF_2$—, $H_2CFCF_2$—, $CH_3CF_2$—, $CF_3CF_2CF_2$—, $HCF_2CF_2CF_2$—, $H_2CFCF_2CF_2$—, $CH_3CF_2CF_2$—, and those represented by the following formulas:

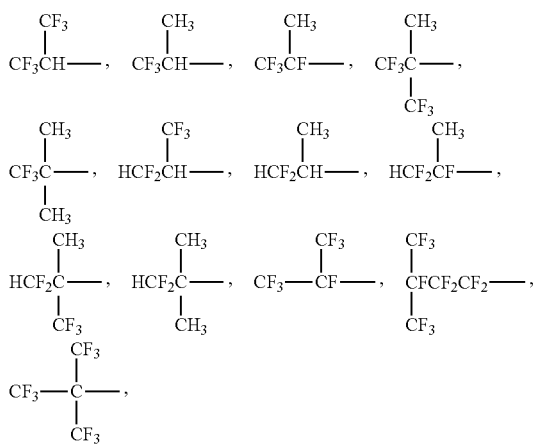

may be mentioned as preferred fluorinated alkyl groups (a).

The fluorinated alkyl group (b) having an ether bond is an alkyl group which has an ether bond and in which at least one hydrogen atom is replaced by a fluorine atom. The fluorinated alkyl group (b) having an ether bond preferably has a carbon number of 2 to 17. If the carbon number is too large, the fluorinated saturated cyclic carbonate (A) may have a high viscosity, and also the number of fluorine-containing groups increases. Thus, the solubility of the electrolyte salt may be poor due to reduction in the permittivity, and the compatibility with other solvents may be poor. Accordingly, the carbon number of the fluorinated alkyl group (b) having an ether bond is preferably 2 to 10, more preferably 2 to 7.

The alkylene group which constitutes the ether segment of the fluorinated alkyl group (b) having an ether bond may be a linear or branched alkylene group. Examples of a minimum structural unit constituting such a linear or branched alkylene group are shown below.

(i) Linear minimum structural units

—$CH_2$—, —CHF—, —$CF_2$—, —CHCl—, —CFCl—, —$CCl_2$—

(ii) Branched minimum structural units

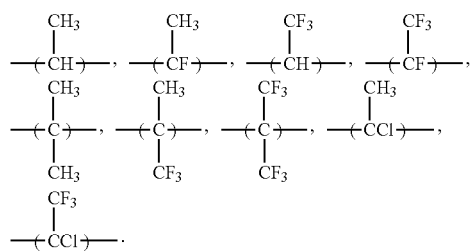

The alkylene group may be constituted by one of these minimum structural units alone, or may be constituted by a combination of linear units (i), of branched units (ii), or of a linear unit (i) and a branched unit (ii). Preferred examples will be mentioned in detail later.

Preferred among these exemplified units are Cl-free structural units because such units are not dehydrochlorinated by a base, and thus are more stable.

Still more preferred examples of the fluorinated alkyl group (b) having an ether bond include those represented by the following formula (b-1):

$R^3$—$(OR^4)_{n1}$— (b-1)

wherein $R^3$ is preferably a C1-C6 alkyl group which may optionally have a fluorine atom; $R^4$ is preferably a C1-C4 alkylene group which may optionally have a fluorine atom; n1 is an integer of 1 to 3; and at least one of $R^3$ and $R^4$ has a fluorine atom.

Examples of the groups for $R^3$ and $R^4$ include the following, and any appropriate combination of these groups can provide the fluorinated alkyl group (b) having an ether bond represented by the formula (b-1). Still, the groups are not limited thereto.

(1) $R^3$ is preferably an alkyl group represented by the formula: $X^c_3C$—$(R^5)_{n2}$—, where three $X^c$'s may be the same as or different from each other, and are individually H or F; $R^5$ is a C1-C5 alkylene group which may optionally have a fluorine atom; and n2 is 0 or 1.

If n2 is 0, $R^3$ may be $CH_3$—, $CF_3$—, $HCF_2$—, or $H_2CF$—, for example.

If n2 is 1, specific examples of a linear group for $R^3$ include $CF_3CH_2$—, $CF_3CF_2$—, $CF_3CH_2CH_2$—, $CF_3CF_2CH_2$—, $CF_3CF_2CF_2$—, $CF_3CH_2CF_2$—, $CF_3CH_2CH_2CH_2$—, $CF_3CF_2CH_2CH_2$—, $CF_3CF_2CF_2CH_2$—, $CF_3CF_2CF_2CF_2$—, $CF_3CF_2CH_2CF_2$—, $CF_3CH_2CH_2CH_2CH_2$—, $CF_3CF_2CH_2CH_2CH_2$—, $CF_3CH_2CF_2CH_2CH_2$—, $CF_3CF_2CF_2CH_2CH_2$—, $CF_3CF_2CF_2CF_2CH_2$—, $CF_3CF_2CH_2CH_2CH_2$—, $CF_3CF_2CH_2CF_2CH_2CH_2$—, $CF_3CF_2CH_2CF_2CH_2$—, $HCF_2CH_2$—, $HCF_2CF_2$—, $HCF_2CH_2CH_2$—, $HCF_2CF_2CH_2$—, $HCF_2CH_2CF_2$—, $HCF_2CF_2CH_2CH_2$—, $HCF_2CH_2CF_2CH_2$—, $HCF_2CF_2CF_2$—, $HCF_2CF_2CH_2CH_2CH_2$—, $HCF_2CH_2CF_2CH_2CH_2$—, $HCF_2CF_2CF_2CH_2$—, $HCF_2CF_2CF_2CH_2CH_2$—, $FCH_2CH_2$—, $FCH_2CF_2$—, $FCH_2CF_2CH_2$—, $FCH_2CF_2CH_2$—, $CH_3CF_2$—, $CH_3CH_2$—, $CH_3CF_2CH_2$—, $CH_3CF_2CF_2$—, $CH_3CH_2CH_2$—, $CH_3CF_2CH_2CF_2$—, $CH_3CF_2CF_2CF_2$—, $CH_3CH_2CF_2CF_2$—, $CH_3CH_2CH_2CH_2$—, $CH_3CF_2CH_2CF_2CH_2$—, $CH_3CF_2CF_2CF_2CH_2$—, $CH_3CF_2CF_2CH_2CH_2$—, $CH_3CH_2CF_2CF_2CH_2$—, $CH_3CF_2CH_2CF_2CH_2$, $CH_3CF_2CH_2CF_2CH_2CH_2$—, $CH_3CH_2CF_2CF_2CH_2CH_2$—, and $CH_3CF_2CH_2CF_2CH_2CH_2$—.

If n2 is 1, those represented by the following formulas:

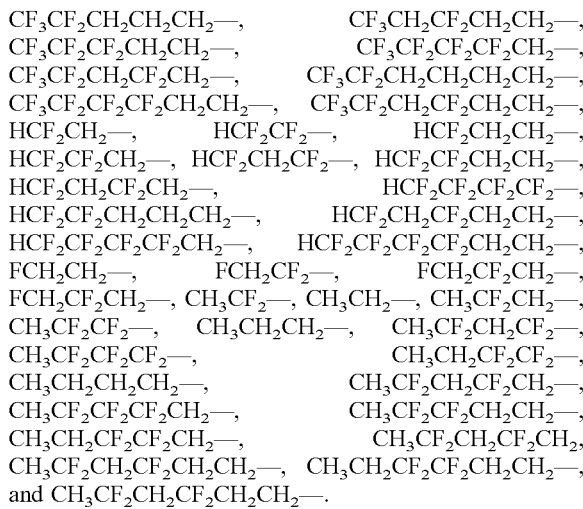

may be mentioned as branched groups for $R^3$.

If the group for $R^3$ has a branch such as —$CH_3$ or —$CF_3$, the viscosity is likely to be high. Thus, the group for $R^3$ is more preferably a linear group.

(2) In the segment —$(OR^4)_{n1}$— of the formula (b-1), n1 is an integer of 1 to 3, preferably 1 or 2. If n1 is 2 or 3, $R^4$'s may be the same as or different from each other.

Preferred specific examples of the group for $R^4$ include the following linear or branched groups.

Examples of the linear groups include —$CH_2$—, —CHF—, —$CF_2$—, —$CH_2CH_2$—, —$CF_2CH_2$—, —$CF_2CF_2$—, —$CH_2CF_2$—, —$CH_2CH_2CH_2$—, —$CH_2CH_2CF_2$—, —$CH_2CF_2CH_2$—, —$CH_2CF_2CF_2$—, —$CF_2CH_2CH_2$—, —$CF_2CF_2CH_2$—, —$CF_2CH_2CF_2$—, and —$CF_2CF_2CF_2$—.

Those represented by the following formulas:

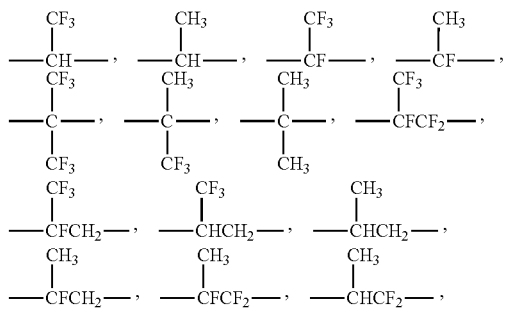

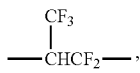

may be mentioned as branched groups.

The fluorinated alkoxy group (c) is an alkoxy group in which at least one hydrogen atom is replaced by a fluorine atom. The fluorinated alkoxy group (c) preferably has a carbon number of 1 to 17. The carbon number is more preferably 1 to 6.

The fluorinated alkoxy group (c) is particularly preferably a fluorinated alkoxy group represented by the formula: $X^d{}_3C-(R^6)_{n3}-O-$ (wherein three $X^d$'s may be the same as or different from each other, and are individually H or F; $R^6$ is preferably a C1-C5 alkylene group which may optionally have a fluorine atom; n3 is 0 or 1; and any of the three $X^d$'s contain a fluorine atom).

Specific examples of the fluorinated alkoxy group (c) include fluorinated alkoxy groups in which an oxygen atom is bonded to an end of the alkyl group for $R^1$ in the formula (a-1).

The fluorinated alkyl group (a), the fluorinated alkyl group (b) having an ether bond, and the fluorinated alkoxy group (c) in the fluorinated saturated cyclic carbonate (A) each preferably have a fluorine content of 10 mass % or more. If the fluorine content is too low, an effect of increasing the flash point may not be sufficiently achieved. Thus, the fluorine content is more preferably 20 mass % or more, still more preferably 30 mass % or more. The upper limit thereof is usually 85 mass %.

The fluorine content of each of the fluorinated alkyl group (a), the fluorinated alkyl group (b) having an ether bond, and the fluorinated alkoxy group (c) is a value calculated by the following formula:

{(Number of fluorine atoms×19)/(formula weight of the formula)}×100(%)

based on the corresponding structural formula.

In order to achieve a good permittivity and oxidation resistance, the fluorine content in the whole fluorinated saturated cyclic carbonate (A) is preferably 5 mass % or more, more preferably 10 mass % or more. The upper limit thereof is usually 76 mass %.

The fluorine content in the whole fluorinated saturated cyclic carbonate (A) is a value calculated based on the structural formula of the fluorinated saturated cyclic carbonate (A) by the following formula:

{(Number of fluorine atoms×19)/(molecular weight of fluorinated saturated cyclic carbonate (A))}×100(%).

Specific examples of the fluorinated saturated cyclic carbonate (A) include the following.

Those represented by the following formulas:

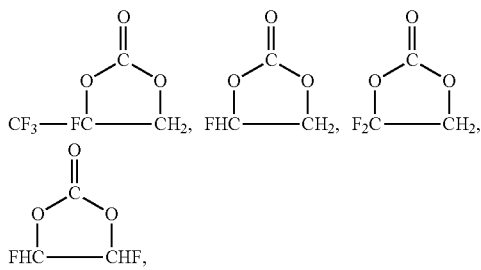

may be mentioned as specific examples of the fluorinated saturated cyclic carbonate (A) represented by the formula (A) in which at least one of $X^1$ to $X^4$ is —F. These compounds have a high withstand voltage and give a good solubility of the electrolyte salt.

Alternatively, those represented by the following formula:

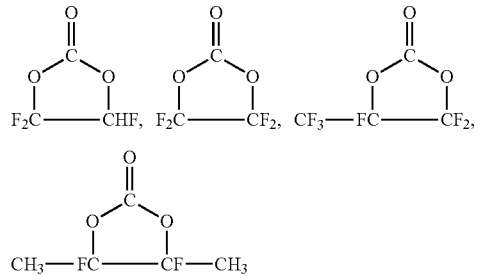

may also be used.

Those represented by the following formulas:

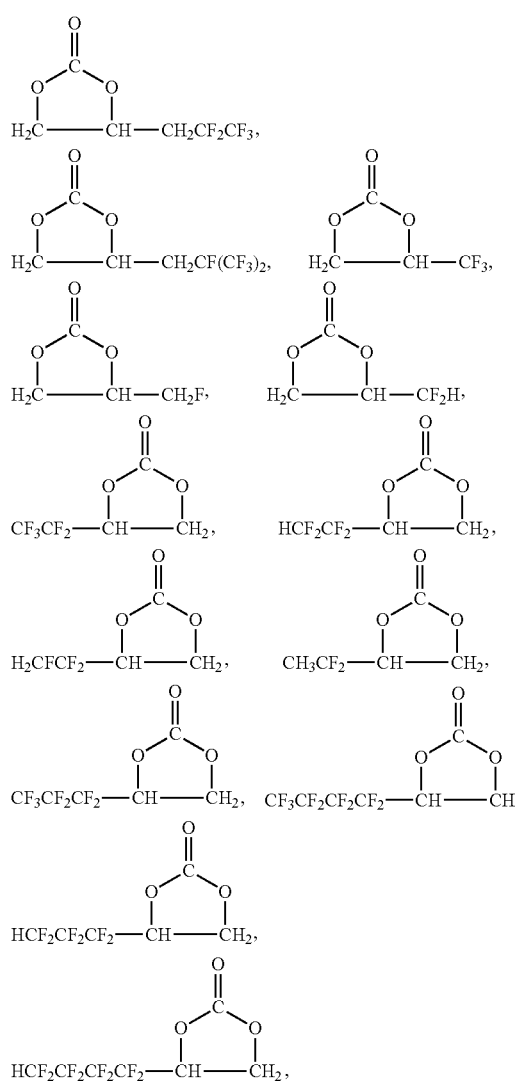

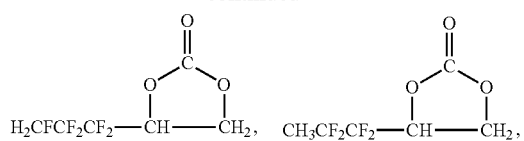
may be mentioned as specific examples of the fluorinated saturated cyclic carbonate (A) represented by the formula (A) in which at least one of $X^1$ to $X^4$ is a fluorinated alkyl group (a) and the others thereof are —H.
Those represented by the following formulas:
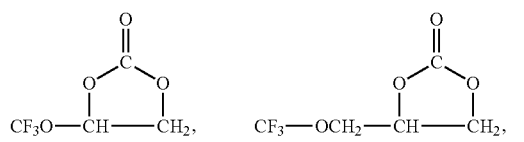
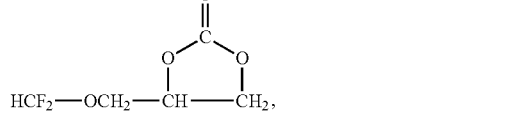
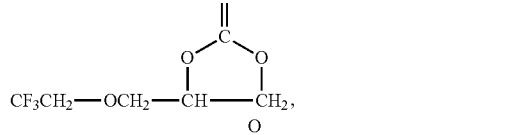
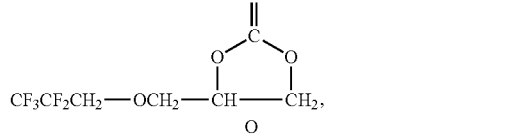
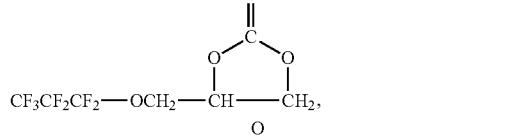
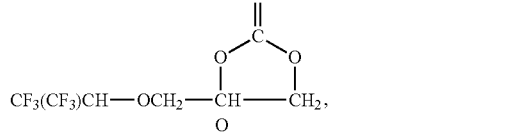
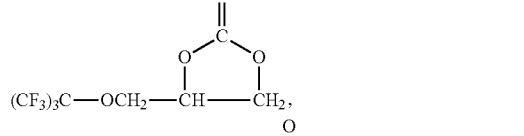
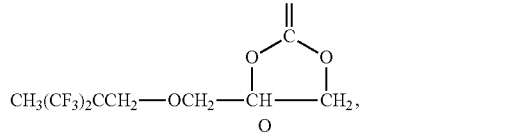
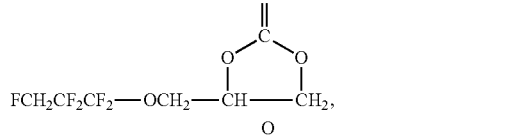
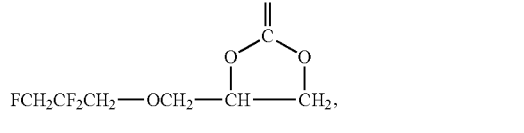
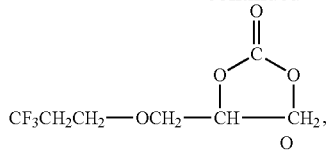
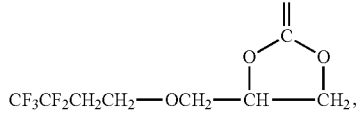
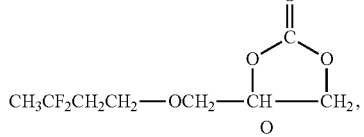
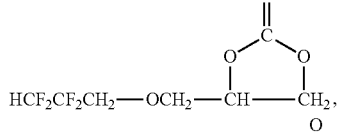
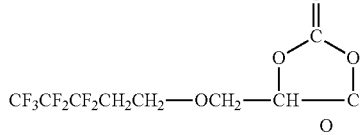
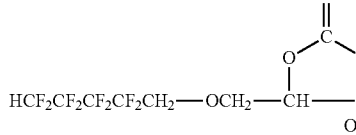
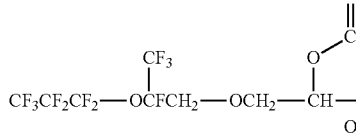
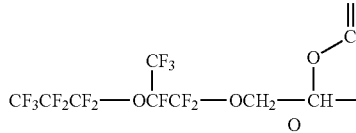
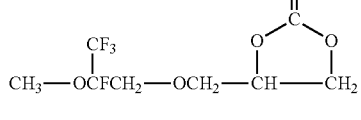
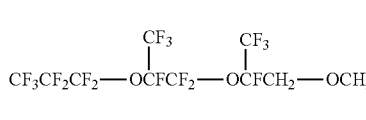
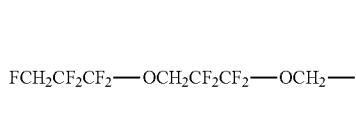
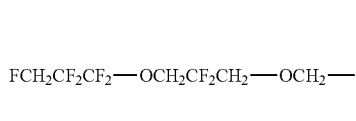
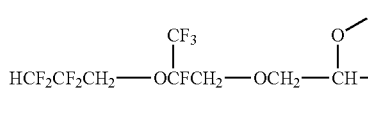

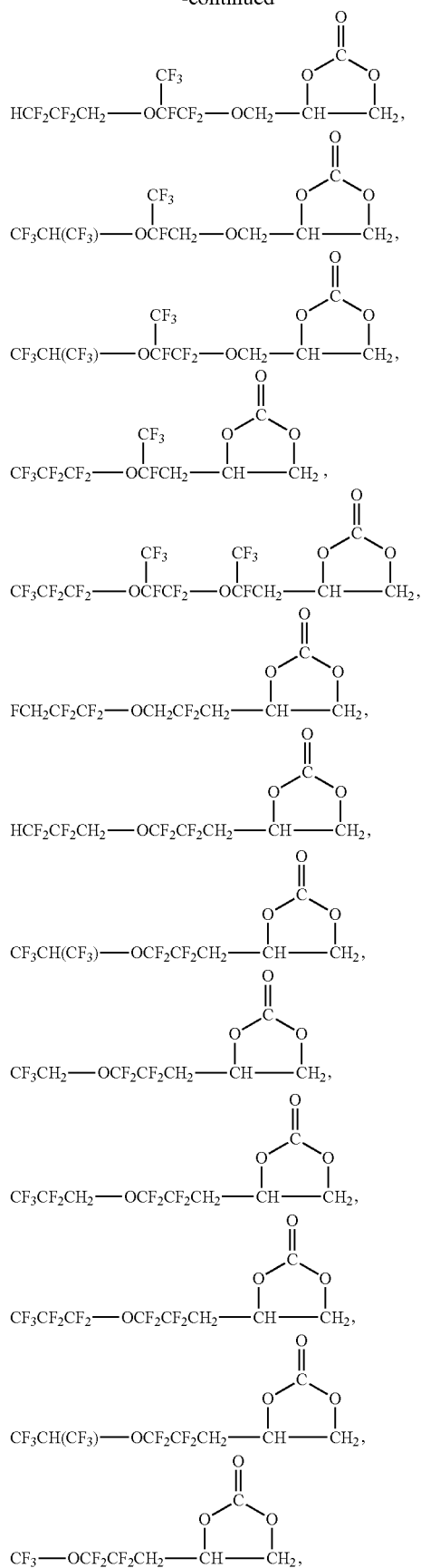
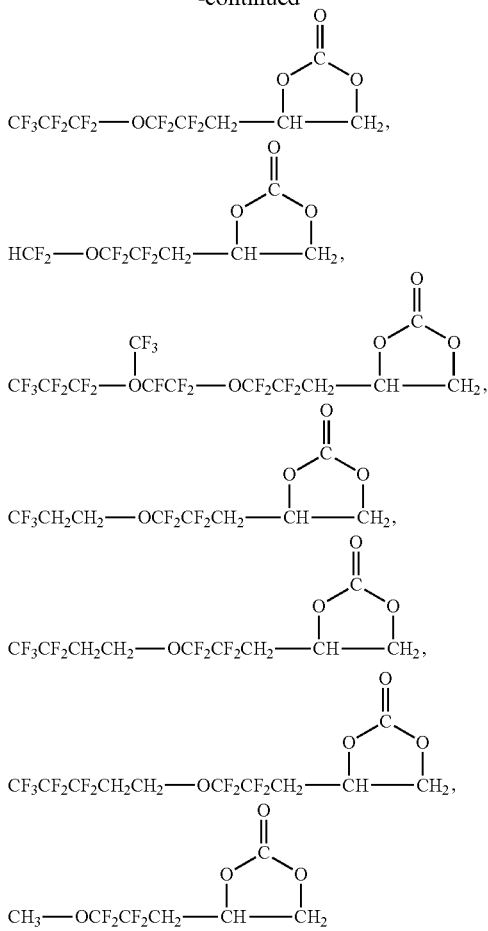

may be mentioned as specific examples of the fluorinated saturated cyclic carbonate (A) represented by the formula (A) in which at least one of $X^1$ to $X^4$ is a fluorinated alkyl group (b) having an ether bond or a fluorinated alkoxy group (c) and the others thereof are —H.

The fluorinated saturated cyclic carbonate (A) is not limited to the above specific examples. One of the above fluorinated saturated cyclic carbonates (A) may be used alone, or two or more thereof may be used in any combination at any ratio. Preferred amounts of the fluorinated saturated cyclic carbonates will be mentioned later, and such preferred amounts correspond to preferred amounts of the fluorinated saturated cyclic carbonates (A).

Preferred as the fluorinated saturated cyclic carbonate (A) are fluoroethylene carbonate and difluoroethylene carbonate.

Examples of the non-fluorinated acyclic carbonate include hydrocarbon acyclic carbonates such as $CH_3OCOOCH_3$ (dimethyl carbonate: DMC), $CH_3CH_2OCOOCH_2CH_3$ (diethyl carbonate: DEC), $CH_3CH_2OCOOCH_3$ (ethyl methyl carbonate: EMC), $CH_3OCOOCH_2CH_2CH_3$ (methyl propyl carbonate), methyl butyl carbonate, ethyl propyl carbonate, and ethyl butyl carbonate. Preferred among these is at least one compound selected from the group consisting of dimethyl carbonate, ethyl methyl carbonate, diethyl carbonate, methyl propyl carbonate, methyl butyl carbonate, ethyl propyl carbonate, and ethyl butyl carbonate.

The fluorinated acyclic carbonate is a chain carbonate containing a fluorine atom.

The fluorinated acyclic carbonate preferably has a fluorine content of 10 to 70.0 mass %. The fluorine content may be calculated based on the structural formula of the fluorinated acyclic carbonate by {(number of fluorine atoms×19)/(molecular weight of fluorinated acyclic carbonate)}×100(%).

Examples of the fluorinated acyclic carbonate include fluorinated acyclic carbonates represented by the formula: $Rf^1OCOORf^2$ (where $Rf^1$ and $Rf^2$ are the same as or different from each other and are individually a C1-C4 alkyl group or fluorine-containing alkyl group, but at least one of $Rf^1$ and $Rf^2$ is a C1-C4 fluorine-containing alkyl group.

$Rf^1$ and $Rf^2$ are the same as or different from each other and are individually a C1-C4 alkyl group or a C1-C4 fluorine-containing alkyl group, but at least one of $Rf^1$ and $Rf^2$ is a C1-C4 fluorine-containing alkyl group.

The above carbon number is preferably 1 to 3 in order to achieve good compatibility with the electrolyte solution.

Examples of $Rf^1$ include $CF_3$—, $CF_3CF_2$—, $(CF_3)_2CH$—, $CF_3CH_2$—, $C_2F_5CH_2$—, $HCF_2CH_2$—, $HCF_2CF_2CH_2$—, and $CF_3CFHCF_2CH_2$—. Preferred among these are $CF_3CH_2$— and $HCF_2CH_2$— in terms of high flame retardance, good rate characteristics, and good oxidation resistance.

Examples of $Rf^2$ include $CF_3$—, $CF_3CF_2$—, $(CF_3)_2CH$—, $CF_3CH_2$—, $C_2F_5CH_2$—, $HCF_2CH_2$—, $HCF_2CF_2CH_2$—, and $CF_3CFHCF_2CH_2$—. Preferred among these are $CF_3CH_2$— and $HCF_2CH_2$— in terms of high flame retardance, good rate characteristics, and good oxidation resistance.

Specific examples of the fluorinated acyclic carbonate include fluorinated acyclic carbonates such as $CF_3CH_2OCOOCH_2CF_3$, $CF_3CH_2OCOOCH_3$, $CF_3CF_2CH_2OCOOCH_2CF_2CF_3$, and $CF_3CF_2CH_2OCOOCH_3$. Examples thereof further include compounds disclosed in JP H06-21992 A, JP 2000-327634 A, and JP 2001-256983 A. Preferred among these is at least one compound selected from the group consisting of $CF_3CH_2OCOOCH_2CF_3$, $CF_3CH_2OCOOCH_3$, and $CF_3CF_2CH_2OCOOCH_2CF_2CF_3$ in terms of high effectiveness of suppressing generation of gas to improve the high-temperature storage characteristics. The fluorine content is more preferably 20 mass % or more, still more preferably 30 mass % or more, particularly preferably 33 mass % or more. The fluorine content is more preferably 60 mass % or less, still more preferably 55 mass % or less.

The electrolyte solution of the present invention preferably contains 10 to 99.99 mass %, more preferably 10 to 95 mass %, still more preferably 15 to 90 mass %, of the solvent relative to the electrolyte solution.

The solvent preferably contains 40 to 100 vol %, more preferably 60 to 100 vol %, still more preferably 90 to 100 vol %, particularly preferably 100 vol %, in total of the non-fluorinated saturated cyclic carbonate, fluorinated saturated cyclic carbonate, non-fluorinated acyclic carbonate, and fluorinated acyclic carbonate.

The solvent preferably contains at least one saturated cyclic carbonate selected from the group consisting of non-fluorinated saturated cyclic carbonates and fluorinated saturated cyclic carbonates and at least one acyclic carbonate selected from the group consisting of non-fluorinated acyclic carbonates and fluorinated acyclic carbonates.

The volume ratio of the saturated cyclic carbonate and the acyclic carbonate is preferably 10/90 to 90/10, more preferably 30/70 or higher, while more preferably 70/30 or lower.

The solvent preferably contains a non-fluorinated acyclic carbonate. The non-fluorinated acyclic carbonate is preferably in an amount of 30 vol % or more, more preferably 40 vol % or more, still more preferably 50 vol % or more, while preferably 90 vol % or less, more preferably 80 vol % or less, relative to the solvent. The electrolyte solution which contains a solvent containing a non-fluorinated acyclic carbonate can be suitably used for electrochemical devices used at relatively low voltages.

If the solvent contains a non-fluorinated acyclic carbonate, the solvent preferably further contains at least one saturated cyclic carbonate selected from the group consisting of non-fluorinated saturated cyclic carbonates and fluorinated saturated cyclic carbonates.

The solvent preferably contains 70 to 100 vol %, more preferably 80 to 100 vol %, still more preferably 90 to 100 vol %, particularly preferably 100 vol %, in total of the non-fluorinated acyclic carbonate and the saturated cyclic carbonate.

The volume ratio of the non-fluorinated acyclic carbonate and the saturated cyclic carbonate is preferably 10/90 to 95/5, more preferably 30/70 or higher, still more preferably 40/60 or higher, while more preferably 90/10 or lower.

If the solvent contains both the non-fluorinated saturated cyclic carbonate and the fluorinated saturated cyclic carbonate as the cyclic carbonates, the volume ratio of the non-fluorinated saturated cyclic carbonate and the fluorinated saturated cyclic carbonate is preferably 10/90 to 90/10, more preferably 30/70 or higher, while more preferably 70/30 or lower.

The solvent preferably contains a fluorinated acyclic carbonate. The fluorinated acyclic carbonate is preferably in an amount of 20 vol % or more, more preferably 30 vol % or more, while preferably 90 vol % or less, more preferably 80 vol % or less, relative to the solvent. The electrolyte solution which contains a solvent containing a fluorinated acyclic carbonate can be suitably used for electrochemical devices to be used at relatively high voltages.

If the solvent contains a fluorinated acyclic carbonate alone as the acyclic carbonate, the fluorinated acyclic carbonate is preferably in an amount of 50 vol % or more, more preferably 60 vol % or more, while preferably 90 vol % or less, more preferably 80 vol % or less, relative to the solvent.

If the solvent contains a fluorinated acyclic carbonate, the solvent also preferably further contains a non-fluorinated acyclic carbonate.

The solvent preferably contains 50 vol % or more, more preferably 60 vol % or more, while preferably 90 vol % or less, more preferably 80 vol % or less, in total of the fluorinated acyclic carbonate and the non-fluorinated acyclic carbonate.

The volume ratio of the fluorinated acyclic carbonate and the non-fluorinated acyclic carbonate is preferably 5/95 or higher, more preferably 10/90 or higher, while preferably 50/50 or lower, more preferably 40/60 or lower.

If the solvent contains a fluorinated acyclic carbonate, the solvent preferably further contains at least one saturated cyclic carbonate selected from the group consisting of non-fluorinated saturated cyclic carbonates and fluorinated saturated cyclic carbonates, more preferably contains a fluorinated saturated cyclic carbonate or fluorinated saturated cyclic carbonate and a non-fluorinated saturated cyclic carbonate.

The solvent preferably contains 40 to 100 vol %, more preferably 60 to 100 vol %, still more preferably 90 to 100 vol %, particularly preferably 100 vol %, in total of the fluorinated acyclic carbonate and the saturated cyclic carbonate.

The volume ratio of the fluorinated acyclic carbonate and the saturated cyclic carbonate is preferably 10/90 to 95/5, more preferably 30/70 or higher, still more preferably 40/60 or higher, while more preferably 90/10 or lower.

If the solvent contains both the non-fluorinated saturated cyclic carbonate and the fluorinated saturated cyclic carbonate as the cyclic carbonates, the volume ratio of the non-fluorinated saturated cyclic carbonate and the fluorinated saturated cyclic carbonate is preferably 10/90 to 90/10, more preferably 30/70 or higher, while more preferably 70/30 or lower.

The electrolyte solution of the present invention contains an electrolyte salt.

Any electrolyte salt usable for electrolyte solutions for electrochemical devices such as secondary batteries and electric double-layer capacitors may be used. Preferred is a lithium salt.

Examples of the lithium salt include inorganic lithium salts such as $LiClO_4$, $LiPF_6$, and $LiBF_4$; and fluoroorganic acid lithium salts such as $LiSO_3CF_3$, $LiN(SO_2CF_3)_2$, $LiN(SO_2C_2F_5)_2$, $LiN(SO_2CF_3)(SO_2C_4F_9)$, $LiC(SO_2CF_3)_3$, $LiPF_4(CF_3)_2$, $LiPF_4(C_2F_5)_2$, $LiPF_4(SO_2CF_3)_2$, $LiPF_4(SO_2C_2F_5)_2$, $LiBF_2(CF_3)_2$, $LiBF_2(C_2F_5)_2$, $LiBF_2(SO_2CF_3)_2$, $LiBF_2(SO_2C_2F_5)_2$, lithium difluoro(oxalato)borate, lithium bis(oxalato)borate, and salts represented by the formula: $LiPF_a(C_nF_{2n+1})_{6-a}$ (wherein a is an integer of 0 to 5; and n is an integer of 1 to 6). These may be used alone or in combination of two or more.

In order to suppress degradation of the electrolyte solution after high-temperature storage, the lithium salt is particularly preferably at least one selected from the group consisting of $LiPF_6$, $LiBF_4$, $LiSO_3CF_3$, $LiN(SO_2CF_3)_2$, $LiN(SO_2C_2F_5)_2$, lithium difluoro(oxalato)borate, lithium bis(oxalato)borate, and salts represented by the formula: $LiPF_a(C_nF_{2n+1})_{6-a}$ (wherein a is an integer of 0 to 5; and n is an integer of 1 to 6).

Examples of the salts represented by the formula: $LiPF_a(C_nF_{2n+1})_{6-a}$ include $LiPF_3(CF_3)_3$, $LiPF_3(C_2F_5)_3$, $LiPF_3(C_3F_7)_3$, $LiPF_3(C_4F_9)_3$, $LiPF_4(CF_3)_2$, $LiPF_4(C_2F_5)_2$, $LiPF_4(C_3F_7)_2$, and $LiPF_4(C_4F_9)_2$ wherein the alkyl group represented by $C_3F_7$ or $C_4F_9$ in the formula may be either linear or branched.

The concentration of the electrolyte salt in the electrolyte solution is preferably 0.5 to 3 mol/L. If the concentration thereof is outside this range, the electrolyte solution tends to have a low electric conductivity and the battery performance tends to be impaired.

The concentration of the electrolyte salt is more preferably 0.9 mol/L or more and 1.5 mol/L or less.

The electrolyte salt in the electrolyte solution for electric double layer capacitors is preferably an ammonium salt.

Examples of the ammonium salt include the following salts (IIa) to (IIe).

(IIa) Tetraalkyl Quaternary Ammonium Salts

Preferred examples thereof include tetraalkyl quaternary ammonium salts represented by the following formula (IIa):

$$R^{2a}-\underset{\underset{R^{3a}}{|}}{\overset{\overset{R^{1a}}{|}}{N^{\oplus}}}-R^{4a} \quad X^{\ominus} \tag{IIa}$$

(wherein $R^{1a}$, $R^{2a}$, $R^{3a}$, and $R^{4a}$ may be the same as or different from each other, and are individually a C1-C6 alkyl group which may optionally have an ether bond; and $X^-$ is an anion). In order to improve the oxidation resistance, part or all of the hydrogen atoms in the ammonium salt is/are also preferably replaced by a fluorine atom and/or a C1-C4 fluorine-containing alkyl group.

Preferred specific examples of the tetraalkyl quaternary ammonium salts include tetraalkyl quaternary ammonium salts represented by the following formula (IIa-1):

$$(R^{1a})_x(R^{2a})_y N^{\oplus} X^{\ominus} \tag{IIa-1}$$

(wherein $R^{1a}$, $R^{2a}$, and $X^-$ are defined in the same manner as mentioned above; x and y may be the same as or different from each other, and are individually an integer of 0 to 4, where x+y=4), and alkyl ether group-containing trialkyl ammonium salts represented by the following formula (IIa-2):

$$(R^{5a})_3 N^{\oplus} \quad X^{\ominus} \atop | \atop (R^{6a})_z-O-R^{7a} \tag{IIa-2}$$

(wherein $R^{5a}$ is a C1-C6 alkyl group; $R^{6a}$ is a C1-C6 divalent hydrocarbon group; $R^{7a}$ is a C1-C4 alkyl group; z is 1 or 2; and $X^-$ is an anion). Introduction of an alkyl ether group may lead to reduction in the viscosity.

The anion $X^-$ may be either an inorganic anion or an organic anion. Examples of the inorganic anion include $AlCl_4^-$, $BF_4^-$, $PF_6^-$, $AsF_6^-$, $TaF_6^-$, $I^-$, and $SbF_6^-$. Examples of the organic anion include $CF_3COO^-$, $CF_3SO_3^-$, $(CF_3SO_2)_2N^-$, and $(C_2F_5SO_2)_2N^-$.

In order to achieve good oxidation resistance and ionic dissociation, $BF_4^-$, $PF_6^-$, $AsF_6^-$, and $SbF_6^-$ are preferred.

Preferred specific examples of the tetraalkyl quaternary ammonium salts include $Et_4NBF_4$, $Et_4NClO_4$, $Et_4NPF_6$, $Et_4NAsF_6$, $Et_4NSbF_6$, $Et_4NCF_3SO_3$, $Et_4N(CF_3SO_2)_2N$, $Et_4NC_4F_9SO_3$, $Et_3MeNBF_4$, $Et_3MeNClO_4$, $Et_3MeNPF_6$, $Et_3MeNAsF_6$, $Et_3MeNSbF_6$, $Et_3MeNCF_3SO_3$, $Et_3MeN(CF_3SO_2)_2N$, $Et_3MeNC_4F_9SO_3$, and N,N-diethyl-N-methyl-N-(2-methoxyethyl)ammonium salt. Particularly preferred examples thereof include $Et_4NBF_4$, $Et_4NPF_6$, $Et_4NSbF_6$, $Et_4NAsF_6$, $Et_3MeNBF_4$, and an N,N-diethyl-N-methyl-N-(2-methoxyethyl)ammonium salt.

(IIb) Spirocyclic Bipyrrolidinium Salts

Preferred examples thereof include spirocyclic bipyrrolidinium salts represented by the following formula (IIb-1):

$$\text{(IIb-1)}$$

(wherein $R^{8a}$ and $R^{9a}$ may be the same as or different from each other, and are individually a C1-C4 alkyl group; $X^-$ is an anion; n1 is an integer of 0 to 5; and n2 is an integer of 0 to 5); spirocyclic bipyrrolidinium salts represented by the following formula (IIb-2):

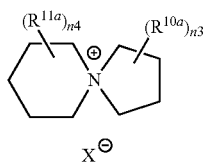

(IIb-2)

(wherein $R^{10a}$ and $R^{11a}$ may be the same as or different from each other, and are individually a C1-C4 alkyl group; $X^-$ is an anion; n3 is an integer of 0 to 5; and n4 is an integer of 0 to 5); and spirocyclic bipyrrolidinium salts represented by the following formula (IIb-3):

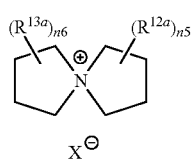

(IIb-3)

(wherein $R^{12a}$ and $R^{13a}$ may be the same as or different from each other, and are individually a C1-C4 alkyl group; $X^-$ is an anion; n5 is an integer of 0 to 5; and n6 is an integer of 0 to 5). In order to improve the oxidation resistance, part or all of the hydrogen atoms in the spirocyclic bipyrrolidinium salt is/are also preferably replaced by a fluorine atom and/or a C1-C4 fluorine-containing alkyl group.

Preferred specific examples of the anion $X^-$ are the same as those mentioned for the salts (IIa). In order to achieve good dissociation and a low internal resistance under high voltage, $BF_4^-$, $PF_6^-$, $(CF_3SO_2)_2N^-$, or $(C_2F_5SO_2)_2N^-$ is particularly preferred.

For example, those represented by the following formulas:

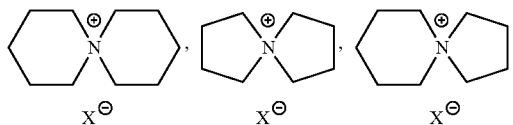

may be mentioned as preferred specific examples of the spirocyclic bipyrrolidinium salts.

These spirocyclic bipyrrolidinium salts are excellent in the solubility in a solvent, the oxidation resistance, and the ion conductivity.

(IIc) Imidazolium Salts

Preferred examples thereof include imidazolium salts represented by the following formula (IIc):

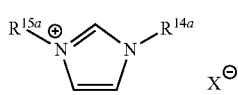

(IIc)

(wherein $R^{14a}$ and $R^{15a}$ may be the same as or different from each other, and are individually a C1-C6 alkyl group; and $X^-$ is an anion). In order to improve the oxidation resistance, part or all of the hydrogen atoms in the imidazolium salt is/are also preferably replaced by a fluorine atom and/or a C1-C4 fluorine-containing alkyl group.

Preferred specific examples of the anion $X^-$ are the same as those mentioned for the salts (IIa).

For example, one represented by the following formula:

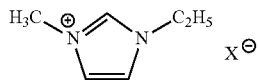

may be mentioned as a preferred specific example of the imidazolium salt.

This imidazolium salt is excellent in that it has a low viscosity and a good solubility.

(IId): N-alkylpyridinium Salts

Preferred examples thereof include N-alkylpyridinium salts represented by the formula (IId):

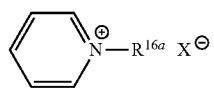

(IId)

(wherein $R^{16a}$ is a C1-C6 alkyl group; and $X^-$ is an anion) In order to improve the oxidation resistance, part or all of the hydrogen atoms in the N-alkylpyridinium salt is/are also preferably replaced by a fluorine atom and/or a C1-C4 fluorine-containing alkyl group.

Preferred specific examples of the anion $X^-$ are the same as those mentioned for the salts (IIa).

For example, those represented by the following formulas:

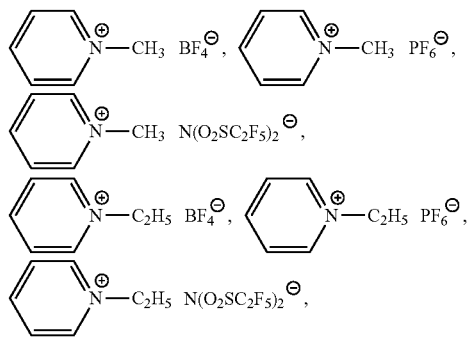

may be mentioned as preferred specific examples of the N-alkylpyridinium salts.

These N-alkylpyridinium salts are excellent in that they have a low viscosity and a good solubility.

(IIe) N,N-dialkylpyrrolidinium Salts

Preferred examples thereof include N,N-dialkylpyrrolidinium salts represented by the formula (IIe):

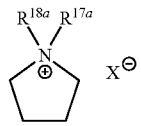

(IIe)

(wherein $R^{17a}$ and $R^{18a}$ may be the same as or different from each other, and are individually a C1-C6 alkyl group; and $X^-$ is an anion). In order to improve the oxidation resistance, part or all of the hydrogen atoms in the N,N-dialkylpyrrolidinium salt is/are also preferably replaced by a fluorine atom and/or a C1-C4 fluorine-containing alkyl group.

Preferred specific examples of the anion $X^-$ are the same as those mentioned for the salts (IIa).

For example, those represented by the following formulas:

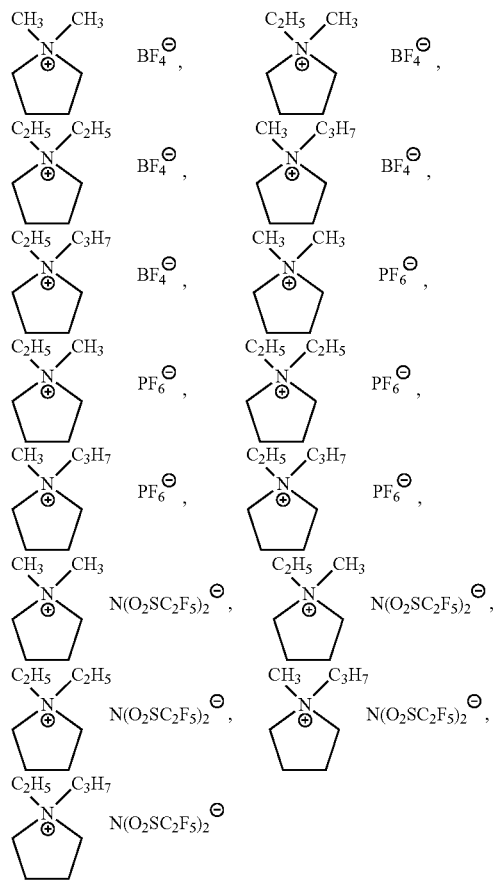

may be mentioned as preferred specific examples of the N,N-dialkylpyrrolidinium salts.

These N,N-dialkylpyrrolidinium salts are excellent in that they have a low viscosity and a good solubility.

Preferred among these ammonium salts are those represented by the formula (IIa), (IIb), or (IIc) because they have a good solubility, oxidation resistance, and ion conductivity. More preferred are those represented by the following formulas:

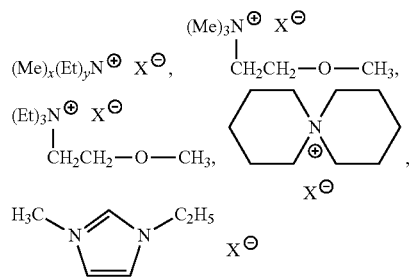

wherein Me is a methyl group; Et is an ethyl group; and $X^-$, x, and y are defined in the same manner as in the formula (IIa-1).

The electrolyte salt for electric double layer capacitors may be a lithium salt. Preferred examples of the lithium salt include $LiPF_6$, $LiBF_4$, $LiAsF_6$, $LiSbF_6$, and $LiN(SO_2C_2H_5)_2$.

In order to further increase the capacity, a magnesium salt may be used. Preferred examples of the magnesium salt include $Mg(ClO_4)_2$ and $Mg(OOC_2H_5)_2$.

If the electrolyte salt is any of the above ammonium salts, the concentration thereof is preferably 0.6 mol/L or higher. If the concentration thereof is lower than 0.6 mol/L, not only the low-temperature characteristics may be poor but also the initial internal resistance may be high. The concentration of the electrolyte salt is more preferably 0.9 mol/L or higher.

For good low-temperature characteristics, the upper limit of the concentration is preferably 3.0 mol/L or lower, more preferably 2.0 mol/L or lower.

If the ammonium salt is triethyl methyl ammonium tetrafluoroborate ($TEMABF_4$), the concentration thereof is preferably 0.8 to 1.9 mol/L in order to achieve excellent low-temperature characteristics.

If the ammonium salt is spirobipyrrolidinium tetrafluoroborate ($SBPBF_4$), the concentration thereof is preferably 0.7 to 2.0 mol/L.

The electrolyte solution of the present invention preferably further includes polyethylene oxide that has a weight average molecular weight of 2000 to 4000 and has —OH, —OCOOH, or —COOH at an end.

Containing such a compound improves the stability at the interfaces between the electrolyte solution and the respective electrodes, and thus can improve the battery characteristics.

Examples of the polyethylene oxide include polyethylene oxide monool, polyethylene oxide carboxylate, polyethylene oxide diol, polyethylene oxide dicarboxylate, polyethylene oxide triol, and polyethylene oxide tricarboxylate. These may be used alone or in combination of two or more.

In order to achieve good battery characteristics, a mixture of polyethylene oxide monool and polyethylene oxide diol and a mixture of polyethylene oxide carboxylate and polyethylene oxide dicarboxylate are preferred.

The polyethylene oxide having too small a weight average molecular weight may be easily oxidatively decomposed. The weight average molecular weight is more preferably 3000 to 4000.

The weight average molecular weight can be determined in terms of polystyrene equivalent by gel permeation chromatography (GPC).

The amount of the polyethylene oxide is preferably $1 \times 10^{-6}$ to $1 \times 10^{-2}$ mol/kg in the electrolyte solution. If the amount of the polyethylene oxide is too large, the battery characteristics may be poor.

The amount of the polyethylene oxide is more preferably $5 \times 10^{-6}$ mol/kg or more.

The electrolyte solution of the present invention preferably further contains, as an additive, at least one selected from the group consisting of unsaturated cyclic carbonates, fluorinated saturated cyclic carbonates, and cyclic sulfonic acid compounds. Containing these compounds suppresses degradation of the battery characteristics.

The unsaturated cyclic carbonate is a cyclic carbonate having an unsaturated bond, i.e., a cyclic carbonate having at least one carbon-carbon unsaturated bond in the molecule. Specific examples thereof include vinylene carbonate compounds such as vinylene carbonate, methyl vinylene carbonate, ethyl vinylene carbonate, 4,5-dimethyl vinylene carbonate, and 4,5-diethyl vinylene carbonate; and vinyl ethylene carbonate compounds such as 4-vinyl ethylene carbonate (VEC), 4-methyl-4-vinyl ethylene carbonate, 4-ethyl-4-vinyl ethylene carbonate, 4-n-propyl-4-vinylene ethylene carbonate, 5-methyl-4-vinyl ethylene carbonate, 4,4-divinyl ethylene carbonate, 4,5-divinyl ethylene carbonate, 4,4-dimethyl-5-methylene ethylene carbonate, and 4,4-diethyl-5-methylene ethylene carbonate. Preferred among these is vinylene carbonate, 4-vinyl ethylene carbonate, 4-methyl-4-vinyl ethylene carbonate, or 4,5-divinyl ethylene carbonate, and particularly preferred is vinylene carbonate or 4-vinyl ethylene carbonate.

The unsaturated cyclic carbonate may have any molecular weight that does not significantly deteriorate the effects of the present invention. The molecular weight is preferably 50 or higher and 250 or lower. The unsaturated cyclic carbonate having a molecular weight within this range is likely to assure its solubility in the electrolyte solution and to enable sufficient achievement of the effects of the present invention. The molecular weight of the unsaturated cyclic carbonate is more preferably 80 or higher, while more preferably 150 or lower.

The unsaturated cyclic carbonate may also be preferably a fluorinated unsaturated cyclic carbonate.

The number of fluorine atoms in the fluorinated unsaturated cyclic carbonate may be any number that is 1 or greater. The number of fluorine atoms is usually 6 or smaller, preferably 4 or smaller, most preferably 1 or 2.

Examples of the fluorinated unsaturated cyclic carbonate include fluorinated vinylene carbonate derivatives and fluorinated ethylene carbonate derivatives substituted with a substituent having an aromatic ring or a carbon-carbon double bond.

Examples of the fluorinated vinylene carbonate derivatives include 4-fluorovinylene carbonate, 4-fluoro-5-methyl vinylene carbonate, 4-fluoro-5-phenyl vinylene carbonate, 4-allyl-5-fluorovinylene carbonate, and 4-fluoro-5-vinyl vinylene carbonate.

Examples of the fluorinated ethylene carbonate derivatives substituted with a substituent having an aromatic ring or a carbon-carbon double bond include 4-fluoro-4-vinyl ethylene carbonate, 4-fluoro-4-allyl ethylene carbonate, 4-fluoro-5-vinyl ethylene carbonate, 4-fluoro-5-allyl ethylene carbonate, 4,4-difluoro-4-vinyl ethylene carbonate, 4,4-difluoro-4-allyl ethylene carbonate, 4,5-difluoro-4-vinyl ethylene carbonate, 4,5-difluoro-4-allyl ethylene carbonate, 4-fluoro-4,5-divinyl ethylene carbonate, 4-fluoro-4,5-diallyl ethylene carbonate, 4,5-difluoro-4,5-divinyl ethylene carbonate, 4,5-difluoro-4,5-diallyl ethylene carbonate, 4-fluoro-4-phenyl ethylene carbonate, 4-fluoro-5-phenyl ethylene carbonate, 4,4-difluoro-5-phenyl ethylene carbonate, and 4,5-difluoro-4-phenyl ethylene carbonate.

The fluorinated unsaturated cyclic carbonate may have any molecular weight that does not significantly deteriorate the effects of the present invention. The molecular weight is preferably 50 or higher and 500 or lower. The fluorinated unsaturated cyclic carbonate having a molecular weight within this range is likely to assure the solubility of the fluorinated unsaturated cyclic carbonate in the electrolyte solution and to enable sufficient achievement of the effects of the present invention.

The unsaturated cyclic carbonates may be used alone or in any combination of two or more at any ratio.

Examples of the fluorinated saturated cyclic carbonate include compounds mentioned as examples of the fluorinated saturated cyclic carbonates usable for the solvent.

Examples of the cyclic sulfonic acid compounds include 1,3-propane sultone, 1,4-butane sultone, 1-fluoro-1,3-propane sultone, 2-fluoro-1,3-propane sultone, and 3-fluoro-1,3-propane sultone.

In order to improve the high-temperature characteristics, the electrolyte solution of the present invention preferably contains 1,3-propane sultone and/or 1,4-butane sultone.

If at least one compound selected from the group consisting of the unsaturated cyclic carbonates, fluorinated saturated cyclic carbonates, and the cyclic sulfonic acid compounds is used as an additive, the amount thereof in the electrolyte solution is preferably 0.1 to 10 mass %, more preferably 1 mass % or more, while more preferably 5 mass % or less.

The electrolyte solution of the present invention may further contain any other solvents or additives such as cyclic or acyclic carboxylates, ether compounds, nitrogen-containing compounds, boron-containing compounds, organic silicon-containing compounds, fireproof agents (flame retardants), surfactants, additives for increasing the permittivity, improvers for cycle characteristics and rate characteristics, and overcharge inhibitors, to the extent that the effects of the present invention are not impaired.

Examples of the cyclic carboxylates include those having 3 to 12 carbon atoms in total in the structural formula. Specific examples thereof include gamma-butyrolactone, gamma-valerolactone, gamma-caprolactone, and epsilon-caprolactone. Particularly preferred is gamma-butyrolactone because it can improve the battery characteristics owing to improvement in the degree of dissociation of lithium ions.

In general, the amount of the cyclic carboxylate is preferably 0.1 mass % or more, more preferably 1 mass % or more, in 100 mass % of the solvent. The cyclic carboxylate in an amount within this range is likely to improve the electric conductivity of the electrolyte solution, and thus to improve the large-current discharge characteristics of electrolyte batteries. The amount of the cyclic carboxylate is also preferably 10 mass % or less, more preferably 5 mass % or less. Such an upper limit may allow the electrolyte solution to have a viscosity within an appropriate range, may make it possible to avoid a reduction in the electric conductivity, may suppress an increase in the resistance of the negative electrode, and may allow electrolyte batteries to have large-current discharge characteristics within a favorable range.

The cyclic carboxylate to be suitably used may be a fluorinated cyclic carboxylate (fluorolactone). Examples of the fluorolactone include fluorolactones represented by the following formula (C):

(C)

wherein $X^{15}$ to $X^{20}$ may be the same as or different from each other, and are individually —H, —F, —Cl, —CH$_3$, or a fluorinated alkyl group; and at least one of $X^{15}$ to $X^{20}$ is a fluorinated alkyl group.

Examples of the fluorinated alkyl group for $X^{15}$ to $X^{20}$ include —CFH$_2$, —CF$_2$H, —CF$_3$, —CH$_2$CF$_3$, —CF$_2$CF$_3$, —CH$_2$CF$_2$CF$_3$, and —CF(CF$_3$)$_2$. In order to achieve high oxidation resistance and an effect of improving the safety, —CH$_2$CF$_3$ and —CH$_2$CF$_2$CF$_3$ are preferred.

One of $X^{15}$ to $X^{20}$ or a plurality thereof may be replaced by —H, —F, —Cl, —CH$_3$ or a fluorinated alkyl group only when at least one of $X^{15}$ to $X^{20}$ is a fluorinated alkyl group. In order to achieve a good solubility of the electrolyte salt, the number of substituents is preferably 1 to 3, more preferably 1 or 2.

The substitution may be at any of the above sites in the fluorinated alkyl group. In order to achieve a good synthesizing yield, the substitution site is preferably $X^{17}$ and/or $X^{18}$. In particular, $X^{17}$ or $X^{18}$ is preferably a fluorinated alkyl group, especially, —CH$_2$CF$_3$ or —CH$_2$CF$_2$CF$_3$. The substituent for $X^{15}$ to $X^{20}$ other than the fluorinated alkyl group is —H, —F, —Cl, or CH$_3$. In order to achieve a good solubility of the electrolyte salt, —H is preferred.

In addition to those represented by the above formula, the fluorolactone may also be a fluorolactone represented by the following formula (D):

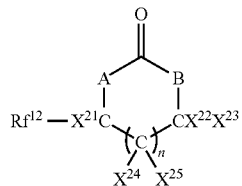

(D)

wherein one of A and B is $CX^{26}X^{27}$ (where $X^{26}$ and $X^{27}$ may be the same as or different from each other, and are individually —H, —F, —Cl, —CF$_3$, —CH$_3$, or an alkylene group in which a hydrogen atom may optionally be replaced by a halogen atom and which may optionally has a hetero atom in the chain) and the other is an oxygen atom; $Rf^{12}$ is a fluorinated alkyl group or fluorinated alkoxy group which may optionally have an ether bond; $X^{21}$ and $X^{22}$ may be the same as or different from each other, and are individually —H, —F, —Cl, —CF$_3$, or CH$_3$; $X^{23}$ to $X^{25}$ may be the same as or different from each other, and are individually —H, —F, —Cl, or an alkyl group in which a hydrogen atom may optionally be replaced by a halogen atom and which may optionally contain a hetero atom in the chain; and n=0 or 1.

Preferred examples of the fluorolactone represented by the formula (D) include a 5-membered ring structure represented by the following formula (E):

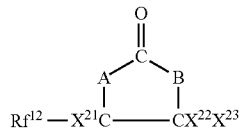

(E)

(wherein A, B, $Rf^{12}$, $X^{21}$, $X^{22}$, and $X^{23}$ are defined in the same manner as in the formula (D)) because it is easily synthesized and has good chemical stability. Further, in relation to the combination of A and B, fluorolactones represented by the following formula (F):

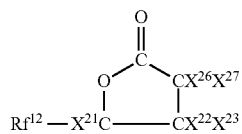

(F)

(wherein $Rf^{12}$, $X^{21}$, $X^{22}$, $X^{23}$, $X^{26}$, and $X^{27}$ are defined in the same manner as in the formula (D)) and fluorolactones represented by the following formula (G):

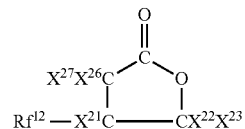

(G)

(wherein $Rf^{12}$, $X^{21}$, $X^{22}$, $X^{23}$, $X^{26}$, and $X^{27}$ are defined in the same manner as in the formula (D)) may be mentioned.

In order to particularly achieve excellent characteristics such as a high permittivity and a high withstand voltage, and to improve the characteristics of the electrolyte solution in the present invention, for example, to achieve a good solubility of the electrolyte salt and to well reduce the internal resistance, those represented by the following formulas:

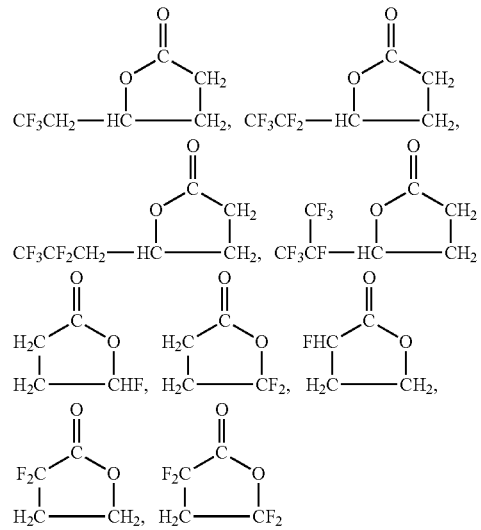

may be mentioned.

Containing a fluorinated cyclic carboxylate leads to effects of, for example, improving the ion conductivity, improving the safety, and improving the stability at high temperature.

Examples of the acyclic carboxylate include those having three to seven carbon atoms in total in the structural formula. Specific examples thereof include methyl acetate, ethyl acetate, n-propyl acetate, isopropyl acetate, n-butyl acetate, isobutyl acetate, t-butyl acetate, methyl propionate, ethyl propionate, n-propyl propionate, isopropyl propionate, n-butyl propionate, isobutyl propionate, t-butyl propionate, methyl butyrate, ethyl butyrate, n-propyl butyrate, isopropyl butyrate, methyl isobutyrate, ethyl isobutyrate, n-propyl isobutyrate, and isopropyl isobutyrate.

In order to improve the ion conductivity owing to a reduction in the viscosity, preferred are methyl acetate, ethyl acetate, n-propyl acetate, n-butyl acetate, methyl propionate, ethyl propionate, n-propyl propionate, isopropyl propionate, methyl butyrate, and ethyl butyrate, for example.

Also, a fluorinated acyclic carboxylate may also suitably be used. Preferred examples of the fluorine-containing ester include fluorinated acyclic carboxylates represented by the following formula (H):

$Rf^{10}COORf^{11}$ (H)

(wherein $Rf^{10}$ is a C1-C2 fluorinated alkyl group; and $Rf^{11}$ is a C1-C4 fluorinated alkyl group) because they are high in flame retardance and have good compatibility with other solvents and good oxidation resistance.

Examples of the group for $Rf^{10}$ include $CF_3$—, $CF_3CF_2$—, $HCF_2CF_2$—, $HCF_2$—, $CH_3CF_2$—, and $CF_3CH_2$—. In order to achieve good rate characteristics, $CF_3$— and $CF_3CF_2$— are particularly preferred.

Examples of the group for $Rf^{11}$ include —$CF_3$, —$CF_2CF_3$, —$CH(CF_3)_2$, —$CH_2CF_3$, —$CH_2CH_2CF_3$, —$CH_2CF_2CFHCF_3$, —$CH_2C_2F_5$, —$CH_2CF_2CF_2H$, —$CH_2CH_2C_2F_5$, —$CH_2CF_2CF_3$, and —$CH_2CF_2CF_2CF_3$. In order to achieve good compatibility with other solvents, —$CH_2CF_3$, —$CH(CF_3)_2$, —$CH_2C_2F_5$, and —$CH_2CF_2CF_2H$ are particularly preferred.

Specifically, for example, the fluorinated acyclic carboxylate may include one or two or more of $CF_3C(=O)OCH_2CF_3$, $CF_3C(=O)OCH_2CH_2CF_3$, $CF_3C(=O)OCH_2C_2F_5$, $CF_3C(=O)OCH_2CF_2CF_2H$, and $CF_3C(=O)OCH(CF_3)_2$. In order to achieve good compatibility with other solvents and good rate characteristics, $CF_3C(=O)OCH_2C_2F_5$, $CF_3C(=O)OCH_2CF_2CF_2H$, $CF_3C(=O)OCH_2CF_3$, and $CF_3C(=O)OCH(CF_3)_2$ are particularly preferred.

The ether compound is preferably a C3-C10 acyclic ether or a C3-C6 cyclic ether.

Examples of the C3-C10 acyclic ether include diethyl ether, di-n-butyl ether, dimethoxy methane, methoxy ethoxy methane, diethoxy methane, dimethoxy ethane, methoxy ethoxy ethane, diethoxy ethane, ethylene glycol di-n-propyl ether, ethylene glycol di-n-butyl ether, and diethylene glycol dimethyl ether.

The ether compound may suitably be a fluorinated ether.

One example of the fluorinated ether is a fluorinated ether (I) represented by the following formula (I):

$$Rf^{13}\text{—O—}Rf^{14} \qquad (I)$$

(wherein $Rf^{13}$ and $Rf^{14}$ may be the same as or different from each other, and are individually a C1-C10 alkyl group or a C1-C10 fluorinated alkyl group; and at least one of $Rf^{13}$ and $Rf^{14}$ is a fluorinated alkyl group). Containing the fluorinated ether (I) can improve the flame retardance of the electrolyte solution, as well as improve the stability and safety at high temperature under high voltage.

In the formula (I), at least one of $Rf^{13}$ and $Rf^{14}$ has only to be a C1-C10 fluorinated alkyl group. In order to further improve the flame retardance and the stability and safety at high temperature under high voltage of the electrolyte solution, both $Rf^{13}$ and $Rf^{14}$ are preferably a C1-C10 fluorinated alkyl group. In this case, $Rf^{13}$ and $Rf^{14}$ may be the same as or different from each other.

More preferably, $Rf^{13}$ and $Rf^{14}$ are the same as or different from each other, and $Rf^{13}$ is a C3-C6 fluorinated alkyl group and $Rf^{14}$ is a C2-C6 fluorinated alkyl group.

If the sum of the carbon numbers of $Rf^{13}$ and $Rf^{14}$ is too small, the fluorinated ether may have too low a boiling point. If the carbon number of $Rf^{13}$ or $Rf^{14}$ is too large, the solubility of the electrolyte salt may be low, which may cause a bad influence on the compatibility with other solvent, and the viscosity may be high so that the rate characteristics (viscosity) may be poor. In order to achieve excellent rate characteristics and boiling point, advantageously, the carbon number of $Rf^{13}$ is 3 or 4 and the carbon number of $Rf^{14}$ is 2 or 3.

The fluorinated ether (I) preferably has a fluorine content of 40 to 75 mass %. The fluorinated ether (I) having a fluorine content within this range may lead to particularly excellent balance between the flame retardance and the compatibility. The above range is also preferred for good oxidation resistance and safety.

The lower limit of the fluorine content is more preferably 45 mass %, still more preferably 50 mass %, particularly preferably 55 mass %. The upper limit thereof is more preferably 70 mass %, still more preferably 66 mass %.

The fluorine content of the fluorinated ether (I) is a value calculated based on the structural formula of the fluorinated ether (I) by the following formula:

{(number of fluorine atoms×19)/(molecular weight of fluorinated ether (I))}×100(%).

Examples of the group for $Rf^{13}$ include $CF_3CF_2CH_2$—, $CF_3CFHCF_2$—, $HCF_2CF_2CF_2$—, $HCF_2CF_2CH_2$—, $CF_3CF_2CH_2CH_2$—, $CF_3CFHCF_2CH_2$—, $HCF_2CF_2CF_2CF_2$—, $HCF_2CF_2CF_2CH_2$—, $HCF_2CF_2CH_2CH_2$—, and $HCF_2CF(CF_3)CH_2$—. Examples of the group for $Rf^{14}$ include —$CH_2CF_2CF_3$, —$CF_2CFHCF_3$, —$CF_2CF_2CF_2H$, —$CH_2CF_2CF_2H$, —$CH_2CH_2CF_2CF_3$, —$CH_2CF_2CFHCF_3$, —$CF_2CF_2CF_2CF_3$, —$CF_2CF_2CF_2CF_2H$, —$CH_2CH_2CF_2CF_2H$, —$CH_2CF(CF_3)CF_2H$, —$CF_2CF_2H$, —$CH_2CF_2H$, and —$CF_2CH_3$.

Specific examples of the fluorinated ether (I) include $HCF_2CF_2CH_2OCF_2CF_2H$, $CF_3CF_2CH_2OCF_2CF_2H$, $HCF_2CF_2CH_2OCF_2CFHCF_3$, $CF_3CF_2CH_2OCF_2CFHCF_3$, $C_6F_{13}OCH_3$, $C_6F_{13}OC_2H_5$, $C_8F_{17}OCH_3$, $C_8F_{17}OC_2H_5$, $CF_3CFHCF_2CH(CH_3)OCF_2CFHCF_3$, $HCF_2CF_2OCH(C_2H_5)_2$, $HCF_2CF_2OC_4H_9$, $HCF_2CF_2OCH_2CH(C_2H_5)_2$, and $HCF_2CF_2OCH_2CH(CH_3)_2$.

In particular, those having $HCF_2$— or $CF_3CFH$— at one end or both ends can provide a fluorinated ether (I) excellent in polarizability and having a high boiling point. The boiling point of the fluorinated ether (I) is preferably 67° C. to 120° C. It is more preferably 80° C. or higher, still more preferably 90° C. or higher.

Such a fluorinated ether (I) may include one or two or more of $CF_3CH_2OCF_2CFHCF_3$, $CF_3CF_2CH_2OCF_2CFHCF_3$, $HCF_2CF_2CH_2OCF_2CFHCF_3$, $HCF_2CF_2CH_2OCH_2CF_2CF_2H$, $CF_3CFHCF_2CH_2OCF_2CFHCF_3$, $HCF_2CF_2CH_2OCF_2CF_2H$, $CF_3CF_2CH_2OCF_2CF_2H$, and the like.

In order to advantageously achieve a high boiling point, good compatibility with other solvents, and a good solubility of the electrolyte salt, the fluorinated ether (I) is preferably at least one selected from the group consisting of $HCF_2CF_2CH_2OCF_2CFHCF_3$ (boiling point: 106° C.), $CF_3CF_2CH_2OCF_2CFHCF_3$ (boiling point: 82° C.), $HCF_2CF_2CH_2OCF_2CF_2H$ (boiling point: 92° C.), and $CF_3CF_2CH_2OCF_2CF_2H$ (boiling point: 68° C.), more preferably at least one selected from the group consisting of $HCF_2CF_2CH_2OCF_2CFHCF_3$ (boiling point: 106° C.) and $HCF_2CF_2CH_2OCF_2CF_2H$ (boiling point: 92° C.).

Examples of the C3-C6 cyclic ether include 1,3-dioxane, 2-methyl-1,3-dioxane, 4-methyl-1,3-dioxane, 1,4-dioxane, and fluorinated compounds thereof. Preferred are dimethoxy methane, diethoxy methane, ethoxy methoxy methane, ethylene glycol n-propyl ether, ethylene glycol di-n-butyl ether, and diethylene glycol dimethyl ether because they have a high ability to solvate with lithium ions and improve the degree of ion dissociation. Particularly preferred are dimethoxy methane, diethoxy methane, and ethoxy methoxy methane because they have a low viscosity and give a high ion conductivity.

Examples of the nitrogen-containing compound include nitrile, fluorine-containing nitrile, carboxylic acid amide, fluorine-containing carboxylic acid amide, sulfonic acid amide, and fluorine-containing sulfonic acid amide. Also, 1-methyl-2-pyrrolidinone, 1-methyl-2-piperidone, 3-methyl-2-oxazilidinone, 1,3-dimethyl-2-imidazolidinone, and N-methylsuccinimide may be used.

Examples of the boron-containing compounds include borate esters such as trimethyl borate and triethyl borate, boric acid ethers, and alkyl borates.

Examples of the organic silicon-containing compounds include $(CH_3)_4$—Si and $(CH_3)_3$—Si—Si$(CH_3)_3$.

Examples of the fireproof agents (flame retardants) include organophosphates and phosphazene-based compounds. Examples of the organophosphates include fluoroalkyl phosphates, non-fluoroalkyl phosphates, and aryl phosphates. Particularly preferred are fluoroalkyl phosphates because they can show a flame retardant effect even at a small amount.

Specific examples of the fluoroalkyl phosphates include fluorodialkyl phosphates disclosed in JP H11-233141 A, alkyl phosphates disclosed in JP H11-283669 A, and fluorotrialkyl phosphates.

Preferred as the fireproof agents (flame retardants) are $(CH_3O)_3P\!=\!O$ and $(CF_3CH_2O)_3P\!=\!O$, for example.

The surfactant may be any of cationic surfactants, anionic surfactants, nonionic surfactants, and amphoteric surfactants. In order to achieve good cycle characteristics and rate characteristics, the surfactant is preferably one containing a fluorine atom.

Preferred examples of such a surfactant containing a fluorine atom include fluorine-containing carboxylic acid salts represented by the following formula (J):

$$Rf^{15}COO^-M^+ \qquad (J)$$

(wherein $Rf^{15}$ is a C3-C10 fluorine-containing alkyl group which may optionally have an ether bond; $M^+$ is $Li^+$, $Na^+$, $K^+$, or $NHR'_3{}^+$ (where R's may be the same as or different from each other, and are individually H or a C1-C3 alkyl group)), and fluorine-containing sulfonic acid salts represented by the following formula (K):

$$Rf^{16}SO_3{}^-M^+ \qquad (K)$$

(wherein $Rf^{16}$ is a C3-C10 fluorine-containing alkyl group which may optionally have an ether bond; $M^+$ is $Li^+$, $Na^+$, $K^+$, or $NHR'_3{}^+$ (where R's may be the same as or different from each other, and are individually H or a C1-C3 alkyl group))

In order to reduce the surface tension of the electrolyte solution without impairing the charge and discharge cycle characteristics, the amount of the surfactant is preferably 0.01 to 2 mass % in the electrolyte solution.

Examples of the additives for increasing the permittivity include sulfolane, methyl sulfolane, γ-butyrolactone, γ-valerolactone, acetonitrile, and propionitrile.

Examples of the improvers for cycle characteristics and rate characteristics include methyl acetate, ethyl acetate, tetrahydrofuran, and 1,4-dioxane.

In order to suppress burst or combustion of batteries in case of overcharge, for example, the overcharge inhibitor is preferably an overcharge inhibitor having an aromatic ring. Examples of the overcharge inhibitor having an aromatic ring include aromatic compounds such as cyclohexyl benzene, biphenyl, alkyl biphenyl, terphenyl, partially hydrogenated terphenyl, t-butyl benzene, t-amyl benzene, diphenyl ether, benzofuran, dibenzofuran, dichloroaniline, and toluene; fluorinated aromatic compounds such as hexafluorobenzene, fluorobenzene, 2-fluorobiphenyl, o-cyclohexyl fluorobenzene, and p-cyclohexyl fluorobenzene; and fluoroanisole compounds such as 2,4-difluoroanisole, 2,5-difluoroanisole, 2,6-difluoroanisole, and 3,5-difluoroanisole. Preferred are aromatic compounds such as biphenyl, alkyl biphenyl, terphenyl, partially hydrogenated terphenyl, cyclohexyl benzene, t-butyl benzene, t-amyl benzene, diphenyl ether, and dibenzofuran. These compounds may be used alone or in combination of two or more. In the case of combination use of two or more compounds, preferred is a combination of cyclohexyl benzene and t-butyl benzene or t-amyl benzene, or a combination of at least one oxygen-free aromatic compound selected from biphenyl, alkyl biphenyl, terphenyl, partially hydrogenated terphenyl, cyclohexyl benzene, t-butyl benzene, t-amyl benzene, and the like, and at least one oxygen-containing aromatic compound selected from diphenyl ether, dibenzofuran, and the like. Such combinations lead to good balance between the overcharge inhibiting characteristics and the high-temperature storage characteristics.

In order to suppress burst or combustion of batteries in case of overcharge, for example, the amount of the overcharge inhibitor is preferably 0.1 to 5 mass % in the electrolyte solution.

The electrolyte solution of the present invention may further contain other known assistants to the extent that the effects of the present invention are not impaired. Examples of such known assistants include carbonate compounds such as erythritan carbonate, spiro-bis-dimethylene carbonate, and methoxy ethyl-methyl carbonate; carboxylic anhydrides such as succinic anhydride, glutaric anhydride, maleic anhydride, citraconic anhydride, glutaconic anhydride, itaconic anhydride, diglycolic anhydride, cyclohexanedicarboxylic anhydride, cyclopentanetetracarboxylic dianhydride, and phenylsuccinic anhydride; spiro compounds such as 2,4,8,10-tetraoxaspiro[5.5]undecane and 3,9-divinyl-2,4,8,10-tetraoxaspiro[5.5]undecane; sulfur-containing compounds such as ethylene sulfite, methyl fluorosulfonate, ethyl fluorosulfonate, methyl methanesulfonate, ethyl methanesulfonate, busulfan, sulfolene, diphenyl sulfone, N,N-dimethyl methane sulfone amide, N,N-diethyl methane sulfone amide, and like other chain sulfones, fluorine-containing chain sulfones, chain sulfonates, fluorine-containing chain sulfonates, cyclic sulfones, fluorine-containing cyclic sulfones, halides of sulfonic acid, and halides of fluorine-containing sulfonic acid; and fluoroaromatic compounds such as hydrocarbon compounds, including heptane, octane, nonane, decane, and cycloheptane. These compounds may be used alone or in combination of two or more. These assistants can improve the capacity retention characteristics and the cycle characteristics after high-temperature storage.

The electrolyte solution of the present invention may be combined with a polymer material and thereby formed into a gel-like (plasticized), gel electrolyte solution.

Examples of such a polymer material include conventionally known polyethylene oxide and polypropylene oxide, modified products thereof (see JP H08-222270 A, JP 2002-100405 A); polyacrylate-based polymers, polyacrylonitrile, and fluororesins such as polyvinylidene fluoride and vinylidene fluoride-hexafluoropropylene copolymers (see JP H04-506726 T, JP H08-507407 T, JP H10-294131 A); and complexes of any of these fluororesins and any hydrocarbon resin (see JP H11-35765 A, JP H11-86630 A). In particular, polyvinylidene fluoride or a vinylidene fluoride-hexafluoropropylene copolymer is preferably used as a polymer material for gel electrolytes.

The electrolyte solution of the present invention may also contain an ion conductive compound disclosed in Japanese Patent Application No. 2004-301934.

This ion conductive compound is an amorphous fluoropolyether compound having a fluorine-containing group at a side chain and is represented by the formula (1-1):

$$A\text{-}(D)\text{-}B \tag{1-1}$$

wherein D is represented by the formula (2-1):

$$\text{-}(D1)_n\text{-}(FAE)_m\text{-}(AE)_p\text{-}(Y)_q\text{-} \tag{2-1}$$

[wherein D1 is an ether unit having a fluoro ether group at a side chain and is represented by the formula (2a):

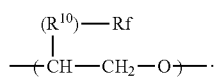 (2a)

(wherein Rf is a fluoro ether group which may optionally have a cross-linkable functional group; and $R^{10}$ is a group or a bond that links Rf and the main chain);

FAE is an ether unit having a fluorinated alkyl group at a side chain and is represented by the formula (2b):

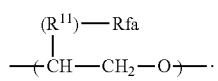 (2b)

(wherein Rfa is a hydrogen atom or a fluorinated alkyl group which may optionally have a cross-linkable functional group; and $R^{11}$ is a group or a bond that links Rfa and the main chain);

AE is an ether unit represented by the formula (2c):

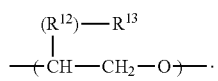 (2c)

(wherein $R^{13}$ is a hydrogen atom, an alkyl group which may optionally have a cross-linkable functional group, an aliphatic cyclic hydrocarbon group which may optionally have a cross-linkable functional group, or an aromatic hydrocarbon group which may optionally have a cross-linkable functional group; and $R^{12}$ is a group or a bond that links $R^{13}$ and the main chain);

Y is a unit having at least one selected from the formulas (2d-1) to (2d-3):

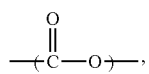 (2d-1)

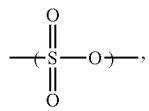 (2d-2)

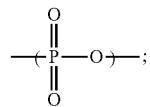 (2d-3)

n is an integer of 0 to 200;
m is an integer of 0 to 200;
p is an integer of 0 to 10000;
q is an integer of 1 to 100;
n+m is not 0; and
the bonding order of D1, FAE, AE, and Y is not specified]; and A and B may be the same as or different from each other, and are individually a hydrogen atom, an alkyl group which may optionally have a fluorine atom and/or a cross-linkable functional group, a phenyl group which may optionally have a fluorine atom and/or a cross-linkable functional group, a —COOH group, —OR (where R is a hydrogen atom or an alkyl group which may optionally have a fluorine atom and/or a cross-linkable functional group), an ester group, or a carbonate group (if an end of D is an oxygen atom, A and B each are none of a —COOH group, —OR, an ester group, and a carbonate group).

The electrolyte solution of the present invention may further contain other additives, if necessary. Examples of such other additives include metal oxides and glass.

The electrolyte solution of the present invention may be prepared by any method using the aforementioned components.

The electrolyte solution of the present invention contains a phosphate. Such a configuration enables production of secondary batteries whose internal resistance is less likely to increase even after repeated charge and discharge and whose cycle capacity retention ratio is high. Accordingly, the electrolyte solution of the present invention can be suitably applied to electrochemical devices such as secondary batteries. Such an electrochemical device or secondary battery including the electrolyte solution of the present invention is also one aspect of the present invention.

Examples of the electrochemical devices include lithium ion secondary batteries, capacitors (electric double-layer capacitors), radical batteries, solar cells (in particular, dye-sensitized solar cells), fuel cells, various electrochemical sensors, electrochromic elements, electrochemical switching elements, aluminum electrolytic capacitors, and tantalum electrolytic capacitors. Preferred are lithium ion secondary batteries and electric double-layer capacitors.

In the following, a lithium ion secondary battery is described as an example of the electrochemical device or secondary battery of the present invention.

The lithium ion secondary battery includes a positive electrode, a negative electrode, and the aforementioned electrolyte solution.

<Positive Electrode>

The positive electrode is formed from a positive electrode mixture containing a positive electrode active material, which is a material of the positive electrode, and a current collector.

The positive electrode active material may be any material that can electrochemically occlude and release lithium ions. For example, a substance containing lithium and at least one transition metal is preferred. Specific examples thereof include lithium-containing transition metal complex oxides and lithium-containing transition metal phosphoric acid compounds. In particular, the positive electrode active material is preferably a lithium-containing transition metal complex oxide that generates a high voltage.

Examples of the lithium-containing transition metal complex oxides include lithium-manganese spinel complex oxides represented by the formula (L): $Li_aMn_{2-b}M^1{}_bO_4$ (wherein $0.9 \le a$; $0 \le b \le 1.5$; and $M^1$ is at least one metal selected from the group consisting of Fe, Co, Ni, Cu, Zn, Al, Sn, Cr, V, Ti, Mg, Ca, Sr, B, Ga, In, Si, and Ge), lithium-nickel complex oxides represented by the formula (M): $LiNi_{1-c}M^2{}_cO_2$ (wherein $0 \le c \le 0.5$; and $M^2$ is at least one metal selected from the group consisting of Fe, Co, Mn, Cu, Zn, Al, Sn, Cr, V, Ti, Mg, Ca, Sr, B, Ga, In, Si, and Ge), and lithium-cobalt complex oxides represented by the formula (N): $LiCO_{1-d}M^3{}_dO_2$ (wherein $0 \le d \le 0.5$; and $M^3$ is at least one metal selected from the group consisting of Fe, Ni, Mn, Cu, Zn, Al, Sn, Cr, V, Ti, Mg, Ca, Sr, B, Ga, In, Si, and Ge).

In order to provide a high-power lithium ion secondary battery having a high energy density, preferred is $LiCoO_2$, $LiMnO_2$, $LiNiO_2$, $LiMn_2O_4$, $LiNi_{0.8}Co_{0.15}Al_{0.05}O_2$, $LiNi_{0.5}Mn_{1.5}O_4$, or $LiNi_{1/3}Co_{1/3}Mn_{1/3}O_2$.

Examples of other positive electrode active materials include $LiFePO_4$, $LiNi_{0.8}Co_{0.2}O_2$, $Li_{1.2}Fe_{0.4}Mn_{0.4}O_2$, $LiNi_{0.5}Mn_{0.5}O_2$, and $LiV_3O_6$.

In order to improve the continuous charge characteristics, the positive electrode active material preferably contains lithium phosphate. The use of lithium phosphate may be achieved in any manner, and the positive electrode active material and lithium phosphate are preferably used in admixture. The lower limit of the amount of lithium phosphate in the sum of the amounts of the positive electrode active material and the lithium phosphate is preferably 0.1 mass % or more, more preferably 0.3 mass % or more, still more preferably 0.5 mass % or more, whereas the upper limit thereof is preferably 10 mass % or less, more preferably 8 mass % or less, still more preferably 5 mass % or less.

To the surface of the positive electrode active material may be attached a substance having a composition different from the positive electrode active material. Examples of the substance attached to the surface include oxides such as aluminum oxide, silicon oxide, titanium oxide, zirconium oxide, magnesium oxide, calcium oxide, boron oxide, antimony oxide, and bismuth oxide; sulfates such as lithium sulfate, sodium sulfate, potassium sulfate, magnesium sulfate, calcium sulfate, and aluminum sulfate; carbonates such as lithium carbonate, calcium carbonate, magnesium carbonate; and carbon.

Such a substance may be attached to the surface of the positive electrode active material by, for example, a method of dissolving or suspending the substance in a solvent, impregnating the solution or suspension into the positive electrode active material, and drying the impregnated material; a method of dissolving or suspending a precursor of the substance in a solvent, impregnating the solution or suspension into the positive electrode active material, and reacting the material and the precursor by heating; or a method of adding the substance to a precursor of the positive electrode active material and simultaneously sintering the materials. In the case where carbon is to be attached, a carbonaceous material in the form of activated carbon, for example, may be mechanically attached to the surface afterward.

The lower limit of the amount (in terms of mass) of the substance attached to the surface relative to the amount of the positive electrode active material is preferably 0.1 ppm or more, more preferably 1 ppm or more, still more preferably 10 ppm or more, whereas the upper limit thereof is preferably 20% or less, more preferably 10% or less, still more preferably 5% or less. The substance attached to the surface suppresses the oxidation of the electrolyte solution on the surface of the positive electrode active material, so that the battery life is improved. If the amount thereof is too small, the substance fails to sufficiently provide the effect. If the amount thereof is too large, the substance may hinder the entrance and exit of lithium ions, so that the resistance may be increased.

Particles of the positive electrode active material may have any conventionally used shape, such as an agglomerative shape, a polyhedral shape, a spherical shape, an ellipsoidal shape, a plate shape, a needle shape, or a pillar shape. The primary particles may agglomerate to form secondary particles.

The positive electrode active material has a tap density of preferably 0.5 g/cm$^3$ or higher, more preferably 0.8 g/cm$^3$ or higher, still more preferably 1.0 g/cm$^3$ or higher. If the tap density of the positive electrode active material is below the lower limit, an increased amount of a dispersion medium is required, as well as increased amounts of a conductive material and a binder are required in formation of a positive electrode active material layer. Thus, the filling rate of the positive electrode active material into the positive electrode active material layer may be limited and the battery capacity may be limited. With a complex oxide powder having a high tap density, a positive electrode active material layer with a high density can be formed. The tap density is preferably as high as possible and has no upper limit, in general. Still, if the tap density is too high, diffusion of lithium ions in the positive electrode active material layer with the electrolyte solution serving as a diffusion medium may function as a rate-determining step, so that the load characteristics may be easily impaired. Thus, the upper limit of the tap density is preferably 4.0 g/cm$^3$ or lower, more preferably 3.7 g/cm$^3$ or lower, still more preferably 3.5 g/cm$^3$ or lower.

The tap density is determined as a powder filling density (tap density) g/cc when 5 to 10 g of the positive electrode active material powder is filled into a 10-ml glass graduated cylinder and the cylinder is tapped 200 times with a stroke of about 20 mm.

The particles of the positive electrode active material have a median size d50 (if the primary particles agglomerate to form secondary particles, the secondary particle size) of preferably 0.3 μm or greater, more preferably 0.5 μm or greater, still more preferably 0.8 μm or greater, most preferably 1.0 μm or greater, whereas the median size d50 is preferably 30 μm or smaller, more preferably 27 μm or smaller, still more preferably 25 μm or smaller, most preferably 22 μm or smaller. If the median size is below the lower limit, products with a high tap density may not be obtained. If the median size exceeds the upper limit, diffusion of lithium into the particles may take a long time, so that the battery performance may be poor or streaks may be formed in formation of positive electrodes for batteries, i.e., when the active material and components such as a conductive material and a binder are formed into slurry by adding a solvent and the slurry is applied in the form of a film, for example. Mixing two or more positive electrode active materials having different median sizes d50 leads to further improved filling in formation of positive electrodes.

The median size d50 is determined using a known laser diffraction/scattering particle size distribution analyzer. In the case of using LA-920 (Horiba, Ltd.) as the particle size distribution analyzer, the dispersion medium used in the measurement is a 0.1 mass % sodium hexametaphosphate aqueous solution and the measurement refractive index is set to 1.24 after 5-minute ultrasonic dispersion.

If the primary particles agglomerate to form secondary particles, the average primary particle size of the positive electrode active material is preferably 0.05 μm or greater, more preferably 0.1 μm or greater, still more preferably 0.2 μm or greater. The upper limit thereof is preferably 5 μm or smaller, more preferably 4 μm or smaller, still more preferably 3 μm or smaller, most preferably 2 μm or smaller. If the average primary particle size exceeds the upper limit, spherical secondary particles are difficult to form, which may have a bad influence on the powder filling or may cause a great reduction in the specific surface area. Thus, the battery performance such as output characteristics is more likely to be impaired. In contrast, if the average primary particle size is below the lower limit, the crystals usually do not sufficiently grow. Thus, charge and discharge may be poorly reversible.

The primary particle size is measured by scanning electron microscopic (SEM) observation. Specifically, the primary particle size is determined as follows. A photograph at a magnification of 10000× is first taken. Any 50 primary particles are selected and the maximum length between the left and right boundary lines of each primary particle is measured along the horizontal line. Then, the average value of the maximum lengths is calculated, which is defined as the primary particle size.

The positive electrode active material has a BET specific surface area of preferably 0.1 m$^2$/g or larger, more preferably 0.2 m$^2$/g or larger, still more preferably 0.3 m$^2$/g or larger. The BET specific surface area is preferably 50 m$^2$/g or smaller, more preferably 40 m$^2$/g or smaller, still more preferably 30 m$^2$/g or smaller. If the BET specific surface area is smaller than the above range, the battery performance may be easily impaired. If it is larger than the above range, the tap density is less likely to be high and formation of the positive electrode active material layer may involve a difficulty in applying the material.

The BET specific surface area is defined by a value determined by single point BET nitrogen adsorption utilizing a gas flow method using a surface area analyzer (e.g., fully automatic surface area measurement device, Ohkura Riken Co., Ltd.), a sample pre-dried in the stream of nitrogen at 150° C. for 30 minutes, and a nitrogen-helium gas mixture with the nitrogen pressure relative to the atmospheric pressure being accurately adjusted to 0.3.

When the lithium ion secondary battery is used as a large-size lithium ion secondary battery for hybrid vehicles or distributed generation, it is required to achieve a high output. Thus, the particles of the positive electrode active material preferably mainly include secondary particles.

The particles of the positive electrode active material preferably include 0.5 to 7.0 vol % of fine particles having an average secondary particle size of 40 μm or smaller and having an average primary particle size of 1 μm or smaller. Containing fine particles having an average primary particle size of 1 μm or smaller leads to an increase in the contact area with the electrolyte solution and more rapid diffusion of lithium ions between the electrode and the electrolyte solution. As a result, the output performance of the battery can be improved.

The positive electrode active material can be produced by any usual method of producing inorganic compounds. In particular, a spherical or ellipsoidal active material can be produced by various methods. For example, a material substance of transition metal is dissolved or crushed and dispersed in a solvent such as water, and the pH of the solution or dispersion is adjusted under stirring to form a spherical precursor. The precursor is recovered and, if necessary, dried. Then, a Li source such as LiOH, Li$_2$CO$_3$, or LiNO$_3$ is added thereto and the mixture is sintered at high temperature, thereby providing an active material.

In order to produce a positive electrode, the aforementioned positive electrode active materials may be used alone or in any combination with one or more having different compositions at any ratio. Preferred examples of the combination in this case include a combination with LiCoO$_2$ and LiMn$_2$O$_4$ in which part of Mn may optionally be replaced by a different transition metal (e.g., LiNi$_{0.33}$Co$_{0.33}$Mn$_{0.33}$O$_2$), and a combination with LiCoO$_2$ in which part of Co may optionally be replaced by a different transition metal.

In order to achieve a high battery capacity, the amount of the positive electrode active material is preferably 50 to 99 mass %, more preferably 80 to 99 mass %, of the positive electrode mixture. The amount of the positive electrode active material in the positive electrode active material layer is preferably 80 mass % or more, more preferably 82 mass % or more, particularly preferably 84 mass % or more. The amount thereof is preferably 99 mass % or less, more preferably 98 mass % or less. Too small an amount of the positive electrode active material in the positive electrode active material layer may lead to an insufficient electric capacity. In contrast, too large an amount thereof may lead to an insufficient strength of the resulting positive electrode.

The positive electrode mixture preferably further includes a binder, a thickening agent, and a conductive material.

The binder may be any material that is safe against a solvent to be used in production of electrodes and the electrolyte solution. Examples thereof include polyvinylidene fluoride, polytetrafluoroethylene, polyethylene, polypropylene, SBR (styrene-butadiene rubber), isoprene rubber, butadiene rubber, ethylene-acrylic acid copolymers, ethylene-methacrylic acid copolymers, polyethylene terephthalate, polymethyl methacrylate, polyimide, aromatic polyamide, cellulose, nitro cellulose, NBR (acrylonitrile-butadiene rubber), fluororubber, ethylene-propylene rubber, styrene-butadiene-styrene block copolymers or hydrogenated products thereof, EPDM (ethylene-propylene-diene terpolymers), styrene-ethylene-butadiene-ethylene copolymers, styrene-isoprene-styrene block copolymers or hydrogenated products thereof, syndiotactic-1,2-polybutadiene, polyvinyl acetate, ethylene-vinyl acetate copolymers, propylene-α-olefin copolymers, fluorinated polyvinylidene fluoride, polytetrafluoroethylene-ethylene copolymers, and polymer compositions having an ion conductivity of alkali metal ions (especially, lithium ions). These agents may be used alone or in any combination of two or more at any ratio.

The amount of the binder, which is expressed as the proportion of the binder in the positive electrode active material layer, is usually 0.1 mass % or more, preferably 1 mass % or more, more preferably 1.5 mass % or more. The proportion is also usually 80 mass % or less, preferably 60 mass % or less, still more preferably 40 mass % or less, most preferably 10 mass % or less. Too low a proportion of the binder may fail to sufficiently hold the positive electrode active material so that the resulting positive electrode may have an insufficient mechanical strength, resulting in deteriorated battery performance such as cycle characteristics. In contrast, too high a proportion thereof may lead to a reduction in battery capacity and conductivity.

Examples of the thickening agent include carboxymethyl cellulose, methyl cellulose, hydroxymethyl cellulose, ethyl cellulose, polyvinyl alcohol, oxidized starch, monostarch phosphate, casein, and salts thereof. These agents may be used alone or in any combination of two or more at any ratio.

The proportion of the thickening agent relative to the active material is usually 0.1 mass % or more, preferably 0.2 mass % or more, more preferably 0.3 mass % or more. It is usually 5 mass % or less, preferably 3 mass % or less, more preferably 2 mass % or less. If the proportion thereof is below this range, easiness of application may be significantly impaired. If the proportion is above this range, the proportion of the active material in the positive electrode active material layer decreases, so that the capacity of the battery may decrease or the resistance between the positive electrode active materials may increase.

The conductive material may be any known conductive material. Specific examples thereof include metal materials such as copper and nickel, and carbon materials such as graphite (e.g., natural graphite, artificial graphite), carbon black (e.g., acetylene black), and amorphous carbon (e.g., needle coke). These materials may be used alone or in any combination of two or more at any ratio. The conductive material is used such that the amount thereof in the positive electrode active material layer is usually 0.01 mass % or more, preferably 0.1 mass % or more, more preferably 1 mass % or more, whereas the amount thereof is usually 50 mass % or less, preferably 30 mass % or less, more preferably 15 mass % or less. If the amount thereof is below this range, the conductivity may be insufficient. In contrast, if the amount thereof is above this range, the battery capacity may decrease.

The solvent for forming slurry may be any solvent that can dissolve or disperse therein the positive electrode active material, the conductive material, and the binder, as well as a thickening agent used if necessary. The solvent may be either of an aqueous solvent or an organic solvent. Examples of the aqueous medium include water and solvent mixtures of an alcohol and water. Examples of the organic medium include aliphatic hydrocarbons such as hexane; aromatic hydrocarbons such as benzene, toluene, xylene, and methyl naphthalene; heterocyclic compounds such as quinoline and pyridine; ketones such as acetone, methyl ethyl ketone, and cyclohexanone; esters such as methyl acetate and methyl acrylate; amines such as diethylene triamine and N,N-dimethylaminopropylamine; ethers such as diethyl ether, propylene oxide, and tetrahydrofuran (THF); amides such as N-methylpyrrolidone (NMP), dimethyl formamide, and dimethyl acetamide; and aprotic polar solvents such as hexamethyl phospharamide and dimethyl sulfoxide.

The current collector for positive electrodes may be formed from any metal material such as aluminum, titanium, tantalum, stainless steel, or nickel, or any alloy thereof; or any carbon material such as carbon cloth or carbon paper. Preferred is any metal material, especially aluminum or alloy thereof.

In the case of a metal material, the current collector may be in the form of metal foil, metal cylinder, metal coil, metal plate, metal film, expanded metal, punched metal, metal foam, or the like. In the case of a carbon material, it may be in the form of carbon plate, carbon film, carbon cylinder, or the like. Preferred among these is a metal film. The film may be in the form of mesh, as appropriate. The film may have any thickness, and the thickness is usually 1 μm or greater, preferably 3 μm or greater, more preferably 5 μm or greater, whereas the thickness is usually 1 mm or smaller, preferably 100 μm or smaller, more preferably 50 μm or smaller. If the film is thinner than this range, it may have an insufficient strength as a current collector. In contrast, if the film is thicker than this range, it may have poor handleability.

In order to reduce the electronic contact resistance between the current collector and the positive electrode active material layer, the current collector also preferably has a conductive auxiliary agent applied on the surface thereof. Examples of the conductive auxiliary agent include carbon and noble metals such as gold, platinum, and silver.

The ratio between the thicknesses of the current collector and the positive electrode active material layer may be any value, and the ratio {(thickness of positive electrode active material layer on one side immediately before injection of electrolyte solution)/(thickness of current collector)} is preferably 20 or lower, more preferably 15 or lower, most preferably 10 or lower. The ratio is also preferably 0.5 or higher, more preferably 0.8 or higher, most preferably 1 or higher. If the ratio exceeds this range, the current collector may generate heat due to Joule heating during high-current-density charge and discharge. If the ratio is below this range, the ratio by volume of the current collector to the positive electrode active material is so high that the capacity of the battery may decrease.

The positive electrode may be produced by a usual method. One example of the production method is a method in which the positive electrode active material is mixed with the aforementioned binder, thickening agent, conductive material, solvent, and other components to form a slurry-like positive electrode mixture, and then this mixture is applied to a current collector, dried, and pressed so as to be densified.

The densification may be achieved using a manual press or a roll press, for example. The density of the positive electrode active material layer is preferably 1.5 $g/cm^3$ or higher, more preferably 2 $g/cm^3$ or higher, still more preferably 2.2 $g/cm^3$ or higher, whereas the density thereof is preferably 5 $g/cm^3$ or lower, more preferably 4.5 $g/cm^3$ or lower, still more preferably 4 $g/cm^3$ or lower. If the density is above this range, the permeability of the electrolyte solution toward the vicinity of the interface between the current collector and the active material may decrease, in particular, the charge and discharge characteristics at high current density may be impaired, so that a high output may not be achieved. If the density is below this range, the conductivity between the active materials may decrease and the resistance of the battery may increase, so that a high output may not be achieved.

In order to improve the stability at high output and high temperature, the area of the positive electrode active material layer is preferably large relative to the outer surface area of an external case of the battery in the case of using the electrolyte solution of the present invention. Specifically, the sum of the areas of the positive electrodes is preferably 15 times or more, more preferably times or more, greater than the surface area of the external case of the secondary battery. For closed, square-shaped cases, the outer surface area of an external case of the battery herein refers to the total area calculated from the dimension of length, width, and thickness of the case portion into which a power-generating element is filled except for a protruding portion of a terminal. For closed, cylinder-like cases, the outer surface area of an external case of the battery herein refers to a geometric surface area of an approximated cylinder of the case portion into which a power-generating element is filled except for a protruding portion of a terminal. The sum of the areas of the positive electrodes herein refers to a geometric surface area of a positive electrode mixture layer opposite to a mixture layer including the negative electrode active material. For structures including a current collector foil and positive electrode mixture layers on both sides of the current collector, the sum of the areas of the positive electrodes is the sum of the areas calculated on the respective sides.

The positive electrode plate may have any thickness. In order to achieve a high capacity and a high output, the lower limit of the thickness of the mixture layer on one side of the current collector excluding the thickness of the base metal foil is preferably 10 μm or greater, more preferably 20 μm or greater, whereas the thickness thereof is preferably 500 μm or smaller, more preferably 450 μm or smaller.

To the surface of the positive electrode plate may be attached a substance having a different composition. Examples of the substance attached to the surface include oxides such as aluminum oxide, silicon oxide, titanium oxide, zirconium oxide, magnesium oxide, calcium oxide, boron oxide, antimony oxide, and bismuth oxide; sulfates such as lithium sulfate, sodium sulfate, potassium sulfate, magnesium sulfate, calcium sulfate, and aluminum sulfate; carbonates such as lithium carbonate, calcium carbonate, and magnesium carbonate; and carbon.

<Negative Electrode>

The negative electrode includes a negative electrode mixture including a negative electrode active material, and a current collector.

Examples of the negative electrode active material include carbonaceous materials that can occlude and release lithium such as pyrolysates of organic matter under various pyrolysis conditions, artificial graphite, and natural graphite; metal oxide materials that can occlude and release lithium such as tin oxide and silicon oxide; lithium metals; various lithium alloys; and lithium-containing metal complex oxide materials. Two or more of these negative electrode active materials may be used in admixture.

The carbonaceous material that can occlude and release lithium is preferably artificial graphite produced by high-temperature treatment of easily graphitizable pitch from various materials, purified natural graphite, or a material obtained by surface-treating such graphite with pitch or other organic matter and then carbonizing the surface-treated graphite. In order to achieve a good balance between the initial irreversible capacity and the high-current-density charge and discharge characteristics, it is more preferably selected from carbonaceous materials obtained by one or more heat treatments at 400° C. to 3200° C. on natural graphite, artificial graphite, artificial carbonaceous substances, or artificial graphite substances; carbonaceous materials which allow the negative electrode active material layer to include at least two or more carbonaceous matters having different crystallinities and/or has an interface between the carbonaceous matters having the different crystallinities; and carbonaceous materials which allow the negative electrode active material layer to have an interface between at least two or more carbonaceous matters having different orientations. These carbonaceous materials may be used alone or in any combination of two or more at any ratio.

Examples of the carbonaceous materials obtained by one or more heat treatments at 400° C. to 3200° C. on artificial carbonaceous substances or artificial graphite substances include natural graphite, coal-based coke, petroleum-based coke, coal-based pitch, petroleum-based pitch, and those prepared by oxidizing these pitches; needle coke, pitch coke, and carbon materials prepared by partially graphitizing these cokes; pyrolysates of organic matter such as furnace black, acetylene black, and pitch-based carbon fibers; carbonizable organic matter and carbides thereof; and solutions prepared by dissolving carbonizable organic matter in a low-molecular-weight organic solvent such as benzene, toluene, xylene, quinoline, or n-hexane, and carbides thereof.

The metal material (excluding lithium-titanium complex oxides) to be used as the negative electrode active material may be any compound that can occlude and release lithium, and examples thereof include simple lithium, simple metals and alloys that constitute lithium alloys, and oxides, carbides, nitrides, silicides, sulfides, and phosphides thereof. The simple metals and alloys constituting lithium alloys are preferably materials containing any of metal and semi-metal elements in the Groups 13 and 14, more preferably simple metal of aluminum, silicon, and tin (hereinafter, referred to as "specific metal elements"), and alloys and compounds containing any of these atoms. These materials may be used alone or in combination of two or more at any ratio.

Examples of the negative electrode active material having at least one atom selected from the specific metal elements include simple metal of any one specific metal element, alloys of two or more specific metal elements, alloys of one or two or more specific metal elements and one or two or more other metal elements, compounds containing one or two or more specific metal elements, and composite compounds such as oxides, carbides, nitrides, silicides, sulfides, and phosphides of the compounds. Use of such a simple metal, alloy, or metal compound as the negative electrode active material can give a high capacity to batteries.

Examples thereof further include compounds in which any of the above composite compounds are complexly bonded with several elements such as simple metals, alloys, and nonmetal elements. Specifically, in the case of silicon or tin, for example, an alloy of this element and a metal that does not serve as a negative electrode can be used. In the case of tin, for example, a composite compound including a combination of 5 or 6 elements, including tin, a metal (excluding silicon) that serves as a negative electrode, a metal that does not serve as a negative electrode, and a nonmetal element, can be used.

Specific examples thereof include simple Si, $SiB_4$, $SiB_6$, $Mg_2Si$, $Ni_2Si$, $TiSi_2$, $MoSi_2$, $CoSi_2$, $NiSi_2$, $CaSi_2$, $CrSi_2$, $Cu_6Si$, $FeSi_2$, $MnSi_2$, $NbSi_2$, $TaSi_2$, $VSi_2$, $WSi_2$, $ZnSi_2$, SiC, $Si_3N_4$, $Si_2N_2O$, $SiO_v$ ($0<v\leq2$), LiSiO, simple tin, $SnSiO_3$, LiSnO, $Mg_2Sn$, and $SnO_w$ ($0<w\leq2$).

Examples thereof further include composite materials of Si or Sn used as a first constitutional element, and second and third constitutional elements. The second constitutional element is at least one selected from cobalt, iron, magnesium, titanium, vanadium, chromium, manganese, nickel, copper, zinc, gallium, and zirconium, for example. The third constitutional element is at least one selected from boron, carbon, aluminum, and phosphorus, for example.

In order to achieve a high battery capacity and excellent battery characteristics, the metal material is preferably simple silicon or tin (which may contain trace impurities), $SiO_v$ ($0<v\leq2$), $SnO_w$ ($0\leq w\leq2$), a Si—Co—C composite material, a Si—Ni—C composite material, a Sn—Co—C composite material, or a Sn—Ni—C composite material.

The lithium-containing metal complex oxide material to be used as the negative electrode active material may be any material that can occlude and release lithium. In order to achieve good high-current-density charge and discharge characteristics, materials containing titanium and lithium are preferred, lithium-containing metal complex oxide materials containing titanium are more preferred, and complex oxides of lithium and titanium (hereinafter, abbreviated as "lithium titanium complex oxides") are still more preferred. In other words, use of a spinel-structured lithium titanium complex oxide contained in the negative electrode active material for electrolyte batteries is particularly preferred because such a compound markedly reduces the output resistance.

Preferred examples of the lithium titanium complex oxides include compounds represented by the formula (O):

$$Li_xTi_yM_zO_4 \quad (O)$$

wherein M is at least one element selected from the group consisting of Na, K, Co, Al, Fe, Ti, Mg, Cr, Ga, Cu, Zn, and Nb.

Particularly preferred compositions represented by the formula (O) are those satisfying one of the following:
(i) $1.2 \leq x \leq 1.4$, $1.5 \leq y \leq 1.7$, $z=0$
(ii) $0.9 \leq x \leq 1.1$, $1.9 \leq y \leq 2.1$, $z=0$
(iii) $0.7 \leq x \leq 0.9$, $2.1 \leq y \leq 2.3$, $z=0$
because the compound structure satisfying any of these compositions gives good balance of the battery performance.

Particularly preferred representative composition of the compound is $Li_{4/3}Ti_{5/3}O_4$ corresponding to the composition (i), $Li_1Ti_2O_4$ corresponding to the composition (ii), and $Li_{4/5}Ti_{11/5}O_4$ corresponding to the composition (iii).

Preferred examples of the structure satisfying $z \neq 0$ include $Li_{4/3}Ti_{4/3}Al_{1/3}O_4$.

The negative electrode mixture preferably further contains a binder, a thickening agent, and a conductive material.

Examples of the binder include the same binders as those mentioned for the positive electrode. The proportion of the binder relative to the negative electrode active material is preferably 0.1 mass % or more, more preferably 0.5 mass % or more, particularly preferably 0.6 mass % or more. The proportion is also preferably 20 mass % or less, more preferably 15 mass % or less, still more preferably 10 mass % or less, particularly preferably 8 mass % or less. If the proportion of the binder relative to the negative electrode active material exceeds the above range, a large amount of the binder may fail to contribute to the battery capacity, so that the battery capacity may decrease. If the proportion is lower than the above range, the negative electrode may have a lowered strength.

In particular, in the case of using a rubbery polymer typified by SBR as a main component, the proportion of the binder relative to the negative electrode active material is usually 0.1 mass % or more, preferably 0.5 mass % or more, more preferably 0.6 mass % or more, whereas the proportion thereof is usually 5 mass % or less, preferably 3 mass % or less, more preferably 2 mass % or less. In the case of using a fluoropolymer typified by polyvinylidene fluoride as a main component, the proportion of the binder relative to the negative electrode active material is usually 1 mass % or more, preferably 2 mass % or more, more preferably 3 mass % or more, whereas the proportion thereof is usually 15 mass % or less, preferably 10 mass % or less, more preferably 8 mass % or less.

Examples of the thickening agent include the same thickening agents as those mentioned for the positive electrode. The proportion of the thickening agent relative to the negative electrode active material is usually 0.1 mass % or more, preferably 0.5 mass % or more, still more preferably 0.6 mass % or more, whereas the proportion thereof is usually 5 mass % or less, preferably 3 mass % or less, still more preferably 2 mass % or less. If the proportion of the thickening agent relative to the negative electrode active material is below the range, easiness of application may be significantly impaired. If the proportion thereof is above the range, the proportion of the negative electrode active material in the negative electrode active material layer decreases, so that the capacity of the battery may decrease or the resistance between the negative electrode active materials may increase.

Examples of the conductive material of the negative electrode include metal materials such as copper and nickel; and carbon materials such as graphite and carbon black.

The solvent for forming slurry may be any solvent that can dissolve or disperse the negative electrode active material and the binder, and a thickening agent and a conductive material that are used as necessary. The slurry-forming solvent may be an aqueous solvent or an organic solvent.

Examples of the aqueous solvent include water and alcohols. Examples of the organic solvent include N-methylpyrrolidone (NMP), dimethyl formamide, dimethyl acetamide, methyl ethyl ketone, cyclohexanone, methyl acetate, methyl acrylate, diethyl triamine, N,N-dimethyl aminopropyl amine, tetrahydrofuran (THF), toluene, acetone, diethyl ether, dimethyl acetamide, hexamethyl phospharamide, dimethyl sulfoxide, benzene, xylene, quinoline, pyridine, methyl naphthalene, and hexane.

Examples of the material of the current collector for negative electrodes include copper, nickel, and stainless steel. For easy processing of the material into a film and low cost, copper is preferred.

The current collector usually has a thickness of 1 μm or larger, preferably 5 μm or larger. The thickness is also usually 100 μm or smaller, preferably 50 μm or smaller. Too thick a negative electrode current collector may cause an excessive reduction in capacity of the whole battery, whereas too thin a current collector may be difficult to handle.

The negative electrode may be produced by a usual method. One example of the production method is a method in which the negative electrode material is mixed with the aforementioned binder, thickening agent, conductive material, solvent, and other components to form a slurry-like mixture, and then this mixture is applied to a current collector, dried, and pressed so as to be densified. In the case of using an alloyed material, a thin film layer containing the above negative electrode active material (negative electrode active material layer) can be produced by vapor deposition, sputtering, plating, or the like technique.

The electrode formed from the negative electrode active material may have any structure. The density of the negative electrode active material existing on the current collector is preferably 1 g·cm$^{-3}$ or higher, more preferably 1.2 g·cm$^{-3}$ or higher, particularly preferably 1.3 g·cm$^{-3}$ or higher, whereas the density thereof is preferably 2.2 g·cm$^{-3}$ or lower, more preferably 2.1 g·cm$^{-3}$ or lower, still more preferably 2.0 g·cm$^{-3}$ or lower, particularly preferably 1.9 g·cm$^{-3}$ or lower. If the density of the negative electrode active material existing on the current collector exceeds the above range, the particles of the negative electrode active material may be broken, the initial irreversible capacity may increase, and the permeability of the electrolyte solution toward the vicinity of the interface between the current collector and the negative electrode active material may be impaired, so that the high-current-density charge and discharge characteristics may be impaired. If the density thereof is below the above range, the conductivity between the negative electrode active materials may be impaired, the resistance of the battery may increase, and the capacity per unit volume may decrease.

The thickness of the negative electrode plate is a design matter in accordance with the positive electrode plate to be used, and may be any value. The thickness of the mixture layer excluding the thickness of the base metal foil is usually 15 μm or greater, preferably 20 μm or greater, more preferably 30 μm or greater, whereas the thickness thereof is usually 300 µm or smaller, preferably 280 µm or smaller, more preferably 250 µm or smaller.

To the surface of the negative electrode plate may be attached a substance having a different composition. Examples of the substance attached to the surface include oxides such as aluminum oxide, silicon oxide, titanium oxide, zirconium oxide, magnesium oxide, calcium oxide, boron oxide, antimony oxide, and bismuth oxide; sulfates such as lithium sulfate, sodium sulfate, potassium sulfate, magnesium sulfate, calcium sulfate, and aluminum sulfate; and carbonates such as lithium carbonate, calcium carbonate, and magnesium carbonate.

<Separator>

The lithium ion secondary battery preferably further includes a separator.

The separator may be formed from any known material and may have any known shape as long as the resulting separator is stable to the electrolyte solution and is excellent in a liquid-retaining ability. The separator is preferably in the form of a porous sheet or a nonwoven fabric which is formed from a material stable to the electrolyte solution of the present invention, such as resin, glass fiber, or inorganic matter, and which is excellent in a liquid-retaining ability.

Examples of the material of a resin or glass-fiber separator include polyolefins such as polyethylene and polypropylene, aromatic polyamide, polytetrafluoroethylene, polyether sulfone, and glass filters. These materials may be used alone or in any combination of two or more at any ratio, for example, in the form of a polypropylene/polyethylene bilayer film or a polypropylene/polyethylene/polypropylene trilayer film. In order to achieve good permeability of the electrolyte solution and a good shut-down effect, the separator is particularly preferably a porous sheet or a nonwoven fabric formed from polyolefin such as polyethylene or polypropylene.

The separator may have any thickness, and the thickness is usually 1 µm or larger, preferably 5 µm or larger, more preferably 8 µm or larger, whereas the thickness is usually 50 µm or smaller, preferably 40 µm or smaller, more preferably 30 µm or smaller. If the separator is thinner than the above range, the insulation and mechanical strength may be poor. If the separator is thicker than the above range, not only the battery performance, such as rate characteristics, may be poor but also the energy density of the whole electrolyte battery may be low.

If the separator is a porous one such as a porous sheet or a nonwoven fabric, the separator may have any porosity. The porosity is usually 20% or higher, preferably 35% or higher, more preferably 45% or higher, whereas the porosity is usually 90% or lower, preferably 85% or lower, more preferably 75% or lower. If the porosity is lower than the range, the film resistance tends to be high and the rate characteristics tend to be poor. If the porosity is higher than the range, the mechanical strength of the separator tends to be low and the insulation tends to be poor.

The separator may also have any average pore size. The average pore size is usually 0.5 µm or smaller, preferably 0.2 µm or smaller, whereas the average pore size is usually 0.05 µm or larger. If the average pore size exceeds the range, short circuits may easily occur. If the average pore size is lower than the range, the film resistance may be high and the rate characteristics may be poor.

Examples of the inorganic material include oxides such as alumina and silicon dioxide, nitrides such as aluminum nitride and silicon nitride, and sulfates such as barium sulfate and calcium sulfate. The inorganic material is in the form of particles or fibers.

The separator is in the form of a thin film such as a nonwoven fabric, a woven fabric, or a microporous film. The thin film favorably has a pore size of 0.01 to 1 µm and a thickness of 5 to 50 µm. In addition to the form of the above separate thin film, the separator may have a structure in which a composite porous layer containing particles of the above inorganic material is formed on the surface of one or both of the positive and negative electrodes using a resin binder. For example, alumina particles having a 90% particle size of smaller than 1 µm are applied to the respective surfaces of the positive electrode with fluororesin used as a binder to form a porous layer.

<Battery Design>

The electrode group may be either a laminated structure including the above positive and negative electrode plates with the above separator in between, or a wound structure including the above positive and negative electrode plates in spiral with the above separator in between. The proportion of the volume of the electrode group in the battery internal volume (hereinafter, referred to as an electrode group proportion) is usually 40% or higher, preferably 50% or higher, whereas the proportion thereof is usually 90% or lower, preferably 80% or lower.

If the electrode group proportion is lower than the above range, the battery capacity may be low. If the electrode group proportion exceeds the above range, the battery may have small space for voids. Thus, when the battery temperature rises to high temperature, the components may swell or the liquid fraction of the electrolyte solution shows a high vapor pressure, so that the internal pressure rises. As a result, the battery characteristics such as charge and discharge repeatability and the high-temperature storageability may be impaired, and a gas-releasing valve for releasing the internal pressure toward the outside may work.

The current collecting structure may be any structure. In order to more effectively improve the high-current-density charge and discharge characteristics by the electrolyte solution of the present invention, the current collecting structure is preferably a structure which reduces the resistances at wiring portions and jointing portions. When the internal resistance is reduced in such a manner, the effects of using the electrolyte solution of the present invention can particularly favorably be achieved.

In an electrode group having the layered structure, the metal core portions of the respective electrode layers are preferably bundled and welded to a terminal. If an electrode has a large area, the internal resistance is high. Thus, multiple terminals may preferably be formed in the electrode to reduce the resistance. In an electrode group having the wound structure, multiple lead structures may be disposed on each of the positive electrode and the negative electrode and bundled to a terminal. Thereby, the internal resistance can be reduced.

The external case may be made of any material that is stable to an electrolyte solution to be used. Specific examples thereof include metals such as nickel-plated steel plates, stainless steel, aluminum and aluminum alloys, and magnesium alloys, and layered film (laminate film) of resin and aluminum foil. In order to reduce the weight, a metal such as aluminum or an aluminum alloy or a laminate film is favorably used.

External cases made of metal may have a sealed up structure formed by welding the metal by laser welding, resistance welding, or ultrasonic welding or a caulking structure using the metal via a resin gasket. External cases made of a laminate film may have a sealed up structure formed by hot melting the resin layers. In order to improve the sealability, a resin which is different from the resin of the laminate film may be disposed between the resin layers. Especially, in the case of forming a sealed up structure by hot melting the resin layers via current collecting terminals, metal and resin are to be bonded. Thus, the resin to be disposed between the resin layers is favorably a resin having a polar group or a modified resin having a polar group introduced thereinto.

The lithium ion secondary battery may have any shape, and examples thereof include cylindrical batteries, square batteries, laminated batteries, coin batteries, and large-size batteries. The shapes and the configurations of the positive electrode, the negative electrode, and the separator may be changed in accordance with the shape of the battery.

A module including the electrochemical device or secondary battery that includes the electrolyte solution of the present invention is also one aspect of the present invention.

Examples of the electrochemical device using the electrolyte solution of the present invention include an electric double-layer capacitor.

In the electric double-layer capacitor, at least one of the positive electrode and the negative electrode is a polarizable electrode. Examples of the polarizable electrode and a non-polarizable electrode include the following electrodes specifically disclosed in JP H09-7896 A.

The polarizable electrode mainly containing activated carbon is preferably one containing inactivated carbon having a large specific surface area and a conductive material, such as carbon black, providing electronic conductivity. The polarizable electrode can be formed by any of various methods. For example, a polarizable electrode including activated carbon and carbon black can be produced by mixing activated carbon powder, carbon black, and phenolic resin, press-molding the mixture, and then sintering and activating the mixture in an inert gas atmosphere and water vapor atmosphere. Preferably, this polarizable electrode is bonded to a current collector using a conductive adhesive, for example.

Alternatively, a polarizable electrode can also be formed by kneading activated carbon powder, carbon black, and a binder in the presence of alcohol and forming the mixture into a sheet shape, and then drying the sheet. This binder may be polytetrafluoroethylene, for example. Alternatively, a polarizable electrode integrated with a current collector can be produced by mixing activated carbon powder, carbon black, a binder, and a solvent to form slurry, applying this slurry to metal foil of a current collector, and then drying the slurry.

The electric double-layer capacitor may have polarizable electrodes mainly containing activated carbon on the respective sides. Still, the electric double-layer capacitor may have a non-polarizable electrode on one side, for example, a positive electrode mainly including an electrode active material such as a metal oxide and a negative electrode including a polarizable electrode that mainly contains activated carbon may be combined; or a negative electrode mainly including a carbon material that can reversibly occlude and release lithium ions or a negative electrode of lithium metal or lithium alloy and a polarizable electrode mainly including activated carbon may be combined.

In place of or in combination with activated carbon, any carbonaceous material such as carbon black, graphite, expanded graphite, porous carbon, carbon nanotube, carbon nanohorn, and Kethenblack may be used.

The non-polarizable electrode is preferably an electrode mainly containing a carbon material that can reversibly occlude and release lithium ions, and this carbon material is made to occlude lithium ions in advance. In this case, the electrolyte used is a lithium salt. The electric double-layer capacitor having such a configuration achieves a much higher withstand voltage of exceeding 4 V.

The solvent used in preparation of slurry in the production of electrodes is preferably one that dissolves a binder. In accordance with the type of a binder, N-methylpyrrolidone, dimethyl formamide, toluene, xylene, isophorone, methyl ethyl ketone, ethyl acetate, methyl acetate, dimethyl phthalate, ethanol, methanol, butanol, or water is appropriately selected.

Examples of the activated carbon used for the polarizable electrode include phenol resin-type activated carbon, coconut shell-type activated carbon, and petroleum coke-type activated carbon. In order to achieve a large capacity, petroleum coke-type activated carbon or phenol resin-type activated carbon is preferably used. Examples of methods of activating the activated carbon include steam activation and molten KOH activation. In order to achieve a larger capacity, activated carbon prepared by molten KOH activation is preferably used.

Preferred examples of the conductive material used for the polarizable electrode include carbon black, Ketjenblack, acetylene black, natural graphite, artificial graphite, metal fiber, conductive titanium oxide, and ruthenium oxide. In order to achieve good conductivity (i.e., low internal resistance), and because too large an amount thereof may lead to a decreased capacity of the product, the amount of the conductive material such as carbon black used for the polarizable electrode is preferably 1 to 50 mass % in the sum of the amounts of the activated carbon and the conductive material.

In order to provide an electric double-layer capacitor having a large capacity and a low internal resistance, the activated carbon used for the polarizable electrode preferably has an average particle size of 20 μm or smaller and a specific surface area of 1500 to 3000 $m^2/g$. Preferred examples of the carbon material for providing an electrode mainly containing a carbon material that can reversibly occlude and release lithium ions include natural graphite, artificial graphite, graphitized mesocarbon microsphere, graphitized whisker, vapor-grown carbon fiber, sintered furfuryl alcohol resin, and sintered novolak resin.

The current collector may be any chemically and electrochemically corrosion-resistant one. Preferred examples of the current collector used for the polarizable electrode mainly containing activated carbon include stainless steel, aluminum, titanium, and tantalum. Particularly preferred materials in terms of the characteristics and cost of the resulting electric double-layer capacitor are stainless steel and aluminum. Preferred examples of the current collector used for the electrode mainly containing a carbon material that can reversibly occlude and release lithium ions include stainless steel, copper, and nickel.

The carbon material that can reversibly occlude and release lithium ions can be allowed to occlude lithium ions in advance by (1) a method of mixing powdery lithium to a carbon material that can reversibly occlude and release lithium ions, (2) a method of placing lithium foil on an electrode including a carbon material that can reversibly occlude and release lithium ions and a binder so that the lithium foil is electrically in contact with the electrode, immersing this electrode in an electrolyte solution containing a lithium salt dissolved therein so that the lithium is ionized, and allowing the carbon material to take in the resulting lithium ions, or (3) a method of placing an electrode including a carbon material that can reversibly occlude and release lithium ions and a binder at a minus side and placing a lithium metal at a plus side, immersing the electrodes in a non-aqueous electrolyte solution containing a lithium salt as an electrolyte, and supplying a current so that the carbon material is allowed to electrochemically take in the ionized lithium.

Examples of known electric double-layer capacitors include wound electric double-layer capacitors, laminated electric double-layer capacitors, and coin-type electric double-layer capacitors. The electric double-layer capacitor of the present invention may also be any of these types.

For example, a wound electric double-layer capacitor is assembled by winding a positive electrode and a negative electrode each of which includes a laminate (electrode) of a current collector and an electrode layer, and a separator in between to provide a wound element, putting this wound element in a case made of, for example, aluminum, filling the case with an electrolyte solution, preferably a non-aqueous electrolyte solution, and sealing the case with a rubber sealant.

In the present invention, a separator formed from a conventionally known material and having a conventionally known structure can also be used. Examples thereof include polyethylene porous membranes, and nonwoven fabric of polypropylene fiber, glass fiber, or cellulose fiber.

In accordance with any known method, the capacitor may be formed into a laminated electric double-layer capacitor in which a sheet-like positive electrode and negative electrode are stacked with an electrolyte solution and a separator in between or a coin-type electric double-layer capacitor in which a positive electrode and a negative electrode are fixed by a gasket with an electrolyte solution and a separator in between.

As mentioned above, use of the electrolyte solution of the present invention can suitably provide secondary batteries excellent in high-temperature storage characteristics, modules using the secondary batteries, and electric double-layer capacitors.

The method for manufacturing the aforementioned phosphate represented by the formula (1) is also one aspect of the present invention.

Non-Patent Literature 1 discloses that bis-2,2,2-trifluoroethyl phosphate monolithium salt is obtained in a yield of about 74% by reacting tris-2,2,2-trifluoroethyl phosphate with an equimolecular amount of lithium hydroxide monohydrate, followed by concentration, recrystallization, and washing steps.

In order to use bis-2,2,2-trifluoroethyl phosphate monolithium salt for electrolyte solutions, contamination of impurities in the bis-2,2,2-trifluoroethyl phosphate monolithium salt needs to be avoided to the utmost so as to restrain reactions with and decomposition of a solvent and/or an electrolyte. However, the method of reacting tris-2,2,2-trifluoroethyl phosphate with an equimolecular amount of lithium hydroxide monohydrate may highly possibly fail to complete the reaction, causing tris-2,2,2-trifluoroethyl phosphate to remain in the crystals. Since tris-2,2,2-trifluoroethyl phosphate has a high boiling point, it is difficult to remove. In Non-Patent Literature 1, the crystals of bis-2,2,2-trifluoroethyl phosphate monolithium salt precipitated in water is washed with pentane. Still, even washing of wet crystals precipitated in water with pentane, which does not mix with water, may highly possibly fail to sufficiently remove the organic matter. Thus, such a method of reacting tris-2,2,2-trifluoroethyl phosphate with an equimolecular amount of lithium hydroxide monohydrate will fail to provide a high-purity fluoroalkyl phosphate monolithium salt usable for electrolyte solutions.

In contrast, if a slightly excessive amount of lithium hydroxide is used, lithium hydroxide may remain in the crystals. Strong alkali substances such as lithium hydroxide cause decomposition of components such as lithium hexafluorophosphate used as an electrolyte and carbonate solvents, and thus contamination thereof must be avoided.

The inventors have performed various studies to find that a phosphate having a low residual alkali concentration and a high purity can be obtained in high yield by reacting a specific organophosphate with 1.01 mole equivalents or more of lithium hydroxide, and then neutralizing the reaction product containing an excessive amount of an alkali metal hydroxide with hydrogen fluoride.

Specifically, the method for manufacturing a phosphate of the present invention includes:

reacting, in a solvent, an organophosphate represented by the formula (2) with an alkali metal hydroxide in an amount of 1.01 mole equivalents or more relative to the organophosphate to provide a composition containing a phosphate represented by the formula (1), the alkali metal hydroxide, and the solvent; and adding hydrogen fluoride to the composition to neutralize the composition and to precipitate an alkali metal fluoride, thereby providing a composition containing the precipitated alkali metal fluoride, the phosphate represented by the formula (1), and the solvent, the formula (1) being the same formula as mentioned above, where neither $R^{11}$ nor $R^{12}$ are C4-C8 alkylsilyl groups, and the formula (2) being $(R^{21}O)(R^{22}O)(R^{23}O)PO$, where $R^{21}$, $R^{22}$, and $R^{23}$ may be the same as or different from each other, and are individually a C1-C11 linear or branched alkyl group, a C2-C11 linear or branched alkenyl group, a C2-C11 linear or branched alkynyl group, a C3-C7 cycloalkyl group, or a C3-C7 cycloalkenyl group, the alkyl group, the alkenyl group, the alkynyl group, the cycloalkyl group, or the cycloalkenyl group may have a halogen atom which substitutes for a hydrogen atom bonding to a carbon atom, may have a cyclic structure, and may have an ether bond or a thioether bond.

The alkali metal hydroxide is preferably lithium hydroxide.

The alkali metal fluoride is preferably lithium fluoride.

In each of the formulas (1) and (2), M is preferably Li.

$R^{21}$, $R^{22}$, and $R^{23}$ may be the same as or different from each other, and are preferably individually represented by $R^{24}CH_2-$, where $R^{24}$ is a hydrogen atom, a C1-C10 linear or branched alkyl group, a C1-C10 linear or branched alkenyl group, a C1-C10 linear or branched alkynyl group, a C3-C6 cycloalkyl group, or a C3-C6 cycloalkenyl group; the alkyl group, the alkenyl group, the alkynyl group, the cycloalkyl group, or the cycloalkenyl group may contain a halogen atom which substitutes for a hydrogen atom bonding to a carbon atom, may have a cyclic structure, and may have an ether bond or a thioether bond.

In the manufacturing method of the present invention, preferably, the alkali metal hydroxide is lithium hydroxide; the alkali metal fluoride is lithium fluoride; M in each of the formulas (1) and (2) is Li; $R^{11}$ and $R^{12}$ may be the same as or different from each other, and are represented by $Rf^{11}CH_2-$ (where $Rf^{11}$ is a C1-C10 linear or branched fluoroalkyl group); and $R^{21}$, $R^{22}$, and $R^{23}$ may be the same as or different from each other, and are represented by $Rf^{21}CH_2$— (where $Rf^{21}$ is a C1-C10 linear or branched fluoroalkyl group).

In other words, the method for manufacturing a phosphate of the present invention is preferably a manufacturing method including the steps of:

reacting an organophosphate (fluoroalkyl phosphate) represented by the formula (2-1) with lithium hydroxide in 1.01 mole equivalents or more relative to the organophosphate in a solvent to provide a composition containing a phosphate (fluoroalkyl phosphate monolithium salt) represented by the formula (1-1), the lithium hydroxide, and the solvent; and adding hydrogen fluoride to the composition to neutralize the composition and to precipitate poorly soluble lithium fluoride, thereby providing a composition containing powder of the lithium fluoride, the phosphate represented by the formula (1), and the solvent, the formula (1-1) being $(Rf^{11}CH_2O)_2PO_2Li$, wherein $Rf^{11}$ is a C1-C10 linear or branched fluoroalkyl group, and the formula (2-1) being $(Rf^{21}CH_2O)_3PO$, wherein $Rf^{21}$ is a C1-C10 linear or branched fluoroalkyl group.

The specification of $Rf^{11}$ and preferred specific examples thereof described for the phosphates represented by the formulas (1) and (1-1) can be directly applied to the specification of $Rf^{21}$ and preferred specific examples thereof for the organophosphates represented by the formulas (2) and (2-1).

Specific examples of the organophosphate represented by the formula (2) or the formula (2-1) include tris-2-fluoroethyl phosphate monolithium salt $((CFH_2CH_2O)_3PO)$, tris-2,2,2-trifluoroethyl phosphate $((CF_3CH_2O)_3PO)$, tris-2-H-2,2-difluoroethyl phosphate $((HCF_2CH_2O)_3PO)$, tris-3-H-2,2,3,3-tetrafluoropropyl phosphate $((HCF_2CF_2CH_2O)_3PO)$, and $(CF_3CF_2CH_2O)_3PO$. For easy availability, preferred among these is at least one selected from the group consisting of tris-2,2,2-trifluoroethyl phosphate $((CF_3CH_2O)_3PO)$, tris-2-H-2,2-difluoroethyl phosphate $((HCF_2CH_2O)_3PO)$, tris-3-H-2,2,3,3-tetrafluoropropyl phosphate $((HCF_2CF_2CH_2O)_3PO)$, and $(CF_3CF_2CH_2O)_3PO$.

In preferred examples of the manufacturing method of the present invention, the alkali metal hydroxide is lithium hydroxide, the alkali metal fluoride is lithium fluoride, M in each of the formulas (1) and (2) is Li, $R^{11}$ is represented by $Rf^{12}CH_2$— (where $Rf^{12}$ is a C1-C10 linear or branched fluoroalkyl group), $R^{12}$ is represented by $Rf^{13}CH_2$— (where $Rf^{13}$ is a C1-C10 linear or branched fluoroalkyl group), $Rf^{12}$ and $Rf^{13}$ are different fluoroalkyl groups, $R^{21}$ is represented by $Rf^{22}CH_2$— (where $Rf^{22}$ is a C1-C10 linear or branched fluoroalkyl group), $R^{22}$ is represented by $Rf^{23}CH_2$— (where $Rf^{23}$ is a C1-C10 linear or branched fluoroalkyl group), and $R^{23}$ is represented by $Rf^{24}CH_2$— (where $Rf^{24}$ is a C1-C10 linear or branched fluoroalkyl group).

$Rf^{22}$, $Rf^{23}$, and $Rf^{24}$, if having a carbon number of 2 or greater, may contain an oxygen atom between carbon atoms to form, for example, a $CF_3$—O—$CF_2$— structure unless oxygen atoms are adjacent to each other. Still, it preferably contains no oxygen atom between carbon atoms.

The carbon numbers of $Rf^{22}$, $Rf^{23}$, and $Rf^{24}$ are individually more preferably 6 or smaller, while preferably 2 or greater.

Examples of $Rf^{22}$, $Rf^{23}$, and $Rf^{24}$ include $CF_3$—, $HCF_2$—, $FCH_2$—, $CF_3$—$CF_2$—, $HCF_2$—$CF_2$—, $FCH_2$—$CF_2$—, $CF_3$—$CH_2$—, $HCF_2$—$CH_2$—, $FCH_2$—$CH_2$—, $CH_3$—$CF_2$—, $CF_3$—$CF_2$—$CF_2$—, $FCH_2CF_2CF_2$—, $HCF_2CF_2CF_2$—, $CF_3$—$CF_2$—$CH_2$—, $CF_3$—$CH_2$—$CF_2$—, $CF_3$—$CH(CF_3)$—, $HCF_2$—$CH(CF_3)$—, $FCH_2$—$CH(CF_3)$—, $CF_3$—$CF(CH_3)$—, $HCF_2$—$CF(CH_3)$—, $FCH_2$—$CF(CH_3)$—, $CH_3CF_2CF_2$—, $CF_3CF_2CF_2CF_2$—, $CF_3CF_2CF_2CH_2$—, $CF_3CF_2CH_2CF_2$—, and $CF_3CH_2CF_2CF_2$—.

Each of $Rf^{22}$, $Rf^{23}$, and $Rf^{24}$ is preferably at least one selected from the group consisting of $FCH_2$—, $CF_3$—, $HCF_2$—, $HCF_2$—$CF_2$—, and $CF_3$—$CF_2$—, more preferably at least one selected from the group consisting of $CF_3$—, $HCF_2$—, $HCF_2$—$CF_2$—, and $CF_3$—$CF_2$—.

$Rf^{22}$, $Rf^{23}$, and $Rf^{24}$ may be different fluoroalkyl groups. Preferred examples of the combination thereof are as follows: $Rf^{22}$ is $CF_3CF_2CF_2$—, $CF_3CF_2$—, $CF_3$—, $HCF_2CF_2$—, $HCF_2$—, or $H_2CF$—; $Rf^{23}$ is $CF_3CF_2$—, $CF_3$—, $HCF_2CF_2$—, $HCF_2$—, or $H_2CF$—; and $Rf^{24}$ is $CF_3$—, $HCF_2CF_2$—, $HCF_2$—, or $H_2CF$—.

Examples of the solvent include water; alcohols such as methanol, ethanol, and 2,2,2-trifluoroethanol; ethers such as diethyl ether, diisopropyl ether, tetrahydrofuran, 1,4-dioxane, and 1,2-dimethoxyethane; and fluorine-containing ethers such as $HCF_2CF_2CH_2OCF_2CFHCF_3$, $CF_3CF_2CH_2OCF_2CFHCF_3$, and $HCF_2CF_2CH_2OCF_2CF_2H$. In order to restrain excessive hydrolysis and avoid remaining of the solvent in the crystals, water is preferred. In order to precipitate the alkali metal fluoride easily, ethers or fluorine-containing ethers are preferred.

If the solvent is water, the alkali metal hydroxide is preferably lithium hydroxide or magnesium hydroxide, more preferably lithium hydroxide. Use of these hydroxides leads to generation of lithium fluoride or magnesium fluoride by neutralization. These fluorides are poorly soluble in water, and thus easily precipitate.

The alkali metal hydroxide is in an amount of 1.01 mole equivalents or more, preferably 1.05 mole equivalents or more, more preferably 1.15 mole equivalents or more, relative to the organophosphate represented by the formula (2). The alkali metal hydroxide is also preferably 2 mole equivalents or less, more preferably 1.5 mole equivalents or less, relative to the organophosphate represented by the formula (2). Too small an amount of the alkali metal hydroxide causes the organophosphate represented by the formula (2) with a high boiling point to remain unreacted. Thus, a purification step is needed additionally, complicating the procedure. Too large an amount of the alkali metal hydroxide fails to give effects corresponding to such an amount, and causes necessity for a large amount of hydrogen fluoride for neutralization.

The alkali metal hydroxide is preferably used in a state of being dissolved in water. For example, an aqueous solution containing 1 mass % or more of the alkali metal hydroxide may be used, or a saturated aqueous solution may be used. Too low a concentration of the alkali metal hydroxide may cause a large amount of the solution after neutralization, so that the concentration may need a large amount of heat, which is possibly wasteful.

The reaction between the organophosphate represented by the formula (2) and the alkali metal hydroxide is preferably performed at 0° C. to 80° C., more preferably 20° C. to 50° C. Too low a reaction temperature may cause freezing of the aqueous solution or precipitation of the alkali metal hydroxide, possibly failing to complete the reaction. Too high a reaction temperature may cause progress of the reaction between the phosphate represented by the formula (1) and the alkali metal hydroxide, possibly lowering the purity of the phosphate represented by the formula (1).

Examples of a method of bringing the organophosphate represented by the formula (2) and the alkali metal hydroxide into contact with each other include a method of adding dropwise an aqueous solution of the alkali metal hydroxide to the organophosphate represented by the formula (2) adjusted to a predetermined temperature; a method of adding the alkali metal hydroxide in the form of solid to the organophosphate represented by the formula (2) adjusted to a predetermined temperature; and a method of adding dropwise the organophosphate represented by the formula (2) to an aqueous solution of the alkali metal hydroxide adjusted to a predetermined temperature. For the reasons such as easy handleability of a device, easiness of the operation, and restraint of the reaction between the resulting phosphate represented by the formula (1) and the alkali metal hydroxide, preferred is a method of adding dropwise an aqueous solution of the alkali metal hydroxide to the organophosphate represented by the formula (2).

The reaction between the organophosphate represented by the formula (2) and the alkali metal hydroxide provides a composition containing the phosphate represented by the formula (1), the alkali metal hydroxide, and the solvent. The resulting composition may have two separated layers. In this case, the composition is preferably stirred to be a homogeneous solution. The resulting composition is alkaline, and usually has a pH of 10 to 12. The phosphate represented by the formula (1) and the alkali metal hydroxide are dissolved in the solvent. When hydrogen fluoride is added to the composition and the composition is neutralized, fine powder of poorly soluble alkali metal fluoride precipitates. The neutralization is preferably performed until the pH reaches 8 to 8.5. Surprisingly, hydrolysis of the phosphate represented by the formula (1) does not proceed in this step, and thus the yield and the purity are not impaired.

Since the manufacturing method includes a step of neutralizing, with hydrogen fluoride, the reaction product containing an excessive amount of the alkali metal hydroxide obtained in the reaction step, the method can provide the phosphate represented by the formula (1) having a high purity even without any purification step such as recrystallization. Thus, the yield is also high.

Examples of the hydrogen fluoride include anhydrous hydrogen fluoride, hydrofluoric acid, and triethylamine hydrofluoride. In order to prevent contamination of impurities, preferred is at least one selected from the group consisting of anhydrous hydrogen fluoride and hydrofluoric acid.

The manufacturing method preferably further includes filtering out the precipitated alkali metal fluoride from the composition containing the precipitated alkali metal fluoride, the phosphate represented by the formula (1), and the solvent, to collect, as a filtrate, a composition containing the phosphate represented by the formula (1) and the solvent. This step enables separation of the alkali metal fluoride powder and the phosphate represented by the formula (1), providing the phosphate represented by the formula (1) hardly containing impurities.

The manufacturing method preferably further includes the step of providing the phosphate represented by the formula (1) in the dry state from the collected filtrate. This step provides the phosphate represented by the formula (1) hardly containing moisture. The phosphate represented by the formula (1) in the dry state may be obtained from the filtrate by heating the filtrate under reduced pressure to evaporate the solvent, and then collecting dried matter of the phosphate represented by the formula (1).

The phosphate represented by the formula (1) preferably has a fluoride ion concentration of 1 mass % or less. In particular, if the method includes the step of collecting the composition as a filtrate and the step of providing the phosphate represented by the formula (1) in the dry state from the collected filtrate, the method easily provides a composition containing fluoride ions and the phosphate represented by the formula (1) and having a fluoride ion concentration of 1 mass % or less relative to the composition. Thus, the phosphate represented by the formula (1) is preferably one obtained after the step of providing the phosphate represented by the formula (1) in the dry state. The lower the fluoride ion concentration is, the better the precipitation of insoluble matter is restrained in preparation of the electrolyte solution. The fluoride ion concentration is determined by the ion selective electrode method.

The purity of the resulting phosphate represented by the formula (1) (dry solid) may be quantified by the internal standard method utilizing $^1$H-NMR analysis. The alkali concentration in the phosphate represented by the formula (1) can be determined by neutralization titration using diluted hydrochloric acid. The moisture concentration in the phosphate represented by the formula (1) can be determined by, for example, the distillation method, the potentiometric Karl Fischer titration method, the coulometric Karl Fischer titration method, or the hydride reaction method, prescribed in JIS K2275. The potentiometric Karl Fischer titration method and the coulometric Karl Fischer titration method can employ a commercially available Karl Fischer moisture meter.

Since the phosphate represented by the formula (1) obtained by the manufacturing method of the present invention has a high purity, it can be suitably used as an additive for electrolyte solutions. Use of an electrolyte solution containing the phosphate represented by the formula (1) obtained by the manufacturing method of the present invention enables production of electrochemical devices whose internal resistance is less likely to increase even after repeated charge and discharge and whose cycle capacity retention ratio is high.

The electrolyte solution preferably contains a solvent, an electrolyte salt, and the phosphate represented by the formula (1) obtained by the manufacturing method of the present invention. Preferred types and amounts of the respective components can be those described for the electrolyte solution of the present invention.

EXAMPLES

The present invention will be described with reference to, but not limited to, examples.

Method for Manufacturing Fluoroalkyl Phosphate Monolithium Salt

Synthesis Example 1: Manufacturing of bis-2,2,2-trifluoroethyl Phosphate Monolithium Salt $((CF_3CH_2O)_2PO_2Li)$ A 1-L glass reactor was charged with 200 g (0.58 mol) of tris-2,2,2-trifluoroethyl phosphate $((CF_3CH_2O)_2PO)$, and the temperature was controlled by water bath such that the internal temperature was 25° C. A dropping funnel was charged with 320 g (0.67 mol) of a 5 mass % lithium hydroxide aqueous solution, and the solution was added dropwise to the system such that the internal temperature was 40° C. or lower. Although the product had two separated layers immediately after the dropwise addition, 24-hour stirring at the same temperature formed the product into a homogeneous solution.

The resulting reaction solution was analyzed by $^{31}$P NMR, and no peak derived from the material, i.e., tris-2,2,2-trifluoroethyl phosphate, was observed.

The resulting reaction solution (pH>12) was neutralized to the neutral point (pH=8.4) with 5 mass % hydrofluoric acid, which caused precipitation of white fine powder. The powder was filtered off. Most part of the filtrate was distilled off at a reduced pressure of 200 Pa and an internal temperature of 80° C., and then the residue was dried at a reduced pressure of 30 Pa and an internal temperature of 150° C. Thereby, 150.4 g of white solid was obtained.

The purity of bis-2,2,2-trifluoroethyl phosphate monolithium salt calculated by the internal standard method utilizing $^{19}$F NMR and $^{31}$P NMR was 99 mass % or more, and the alkali concentration determined by the neutralization titration using hydrochloric acid was 10 mass ppm or less. The moisture concentration calculated by the coulometric Karl Fischer titration method was 150 mass ppm. The fluoride concentration calculated by the ion selective electrode method was 1 mass % or less.

Synthesis Example 2: Manufacturing of bis-2,2,3,3,3-pentafluoropropyl Phosphate Monolithium Salt ((CF$_3$CF$_2$CH$_2$O)$_2$PO$_2$Li)

A 500-mL glass reactor was charged with 100 g (0.20 mol) of tris-2,2,3,3,3-pentafluoropropyl phosphate ((CF$_3$CF$_2$CH$_2$O)$_2$PO), and the temperature was controlled by water bath such that the internal temperature was 25° C. A dropping funnel was charged with 126 g (0.26 mol) of a 5 mass % lithium hydroxide aqueous solution, and the solution was added dropwise to the system such that the internal temperature was 40° C. or lower. Although the product had two separated layers immediately after the dropwise addition, 24-hour stirring at the same temperature formed the product into a homogeneous solution.

The resulting reaction solution was analyzed by $^{31}$P NMR, and no peak derived from the material, i.e., tris-2,2,3,3,3-pentafluoropropyl phosphate was observed.

The resulting reaction solution (pH>12) was neutralized to the neutral point (pH=8.4) with 5 mass % hydrofluoric acid, which caused precipitation of white fine powder. The powder was filtered off. Most part of the filtrate was distilled off at a reduced pressure of 200 Pa and an internal temperature of 80° C., and then the residue was dried at a reduced pressure of 30 Pa and an internal temperature of 150° C. Thereby, 70.8 g of white solid was obtained.

The purity of bis-2,2,3,3,3-pentafluoropropyl phosphate monolithium salt calculated by $^{19}$F NMR and the internal standard method utilizing $^{31}$P NMR was 99 mass % or more, and the alkali concentration determined by the neutralization titration using hydrochloric acid was 15 mass ppm. The moisture concentration calculated by the coulometric Karl Fischer titration method was 130 mass ppm. The fluoride ion concentration calculated by the ion selective electrode method was 1 mass % or less.

Synthesis Example 3: Manufacturing of bis-2,2,3,3-tetrafluoropropyl Phosphate Monolithium Salt ((HCF$_2$CF$_2$CH$_2$O)$_2$PO$_2$Li)

A 500-mL glass reactor was charged with 100 g (0.23 mol) of tris-2,2,3,3-tetrafluoropropyl phosphate ((HCF$_2$CF$_2$CH$_2$O)$_2$PO), and the temperature was controlled by water bath such that the internal temperature was 25° C. A dropping funnel was charged with 126 g (0.27 mol) of a 5 mass % lithium hydroxide aqueous solution, and the solution was added dropwise to the system such that the internal temperature was 40° C. or lower. Although the product had two separated layers immediately after the dropwise addition, 24-hour stirring at the same temperature formed the product into a homogeneous solution.

The resulting reaction solution was analyzed by $^{31}$P NMR, and no peak derived from the material, i.e., tris-2,2,3,3-tetrafluoropropyl phosphate, was observed.

The resulting reaction solution (pH>12) was neutralized to the neutral point (pH=8.4) with 5 mass % hydrofluoric acid, which caused precipitation of white fine powder. The powder was filtered off. Most part of the filtrate was distilled off at a reduced pressure of 200 Pa and an internal temperature of 80° C., and then the residue was dried at a reduced pressure of 30 Pa and an internal temperature of 150° C. Thereby, 70.9 g of white solid was obtained.

The purity of bis-2,2,3,3-tetrafluoropropyl phosphate monolithium salt calculated by the internal standard method utilizing $^{19}$F NMR and $^{31}$P NMR was 99 mass % or more, and the alkali concentration determined by the neutralization titration using hydrochloric acid was 15 mass ppm. The moisture concentration calculated by the coulometric Karl Fischer titration method was 180 mass ppm. The fluoride ion concentration calculated by the ion selective electrode method was 1 mass % or less.

Comparative Synthesis Example 1

A 200-mL glass reactor was charged with 20 g (0.06 mol) of tris-2,2,2-trifluoroethyl phosphate ((CF$_3$CH$_2$O)$_2$PO), and the temperature was controlled by water bath such that the internal temperature was 25° C. A dropping funnel was charged with 103 g (0.07 mol) of a 5 mass % lithium carbonate aqueous suspension, and the suspension was added dropwise to the system. No generation of heat due to the reaction was observed. The product had two separated layers immediately after the dropwise addition, which was remained even after 24-hour stirring at the same temperature.

The upper layer solution was analyzed by $^{31}$P NMR, and no peak derived from bis-2,2,2-trifluoroethyl phosphate monolithium salt was obtained.

The lower layer solution was analyzed by $^{31}$P NMR, and the peak derived from tris-2,2,2-trifluoroethyl phosphate alone was observed.

Experiment 1 (Evaluation of 4.4 V Grade Lithium Battery)

Electrolyte solutions of Examples 1 to 20 and electrolyte solutions of Comparative Examples 1 to 5 were prepared as follows and lithium ion secondary batteries were produced using the resulting electrolyte solutions. The resistance increasing rates and the cycle capacity retention ratios of the respective batteries were evaluated.

(Preparation of Electrolyte Solution)

An acyclic carbonate(s) and a cyclic carbonate(s) were mixed in a ratio shown in Table 1 under dry argon atmosphere. To this solution was added dry fluoroalkyl phosphate monolithium salt in an amount shown in Table 1, and dry LiPF$_6$ was further added so as to be a concentration of 1.0 mol/L. Thereby, a non-aqueous electrolyte solution was obtained. The amount of the fluoroalkyl phosphate monolithium salt blended was expressed by mass % relative to the acyclic carbonate(s) and the cyclic carbonate(s).

The compounds in Table 1 are as follows.

Acyclic Carbonates
  a: dimethyl carbonate
  b: ethylmethyl carbonate
  c: diethyl carbonate
  d: $CF_3CH_2OCOOCH_3$
  e: $CF_3CH_2OCOOCH_2CF_3$ Cyclic Carbonates
  EC: ethylene carbonate
  FEC: 4-fluoro-1,3dioxolan-2-one Additives
  F: $(CF_3CH_2O)_2PO_2Li$
  G: $(CF_3CF_2CH_2O)_2PO_2Li$
  H: $(HCF_2CF_2CH_2O)_2PO_2Li$ (Production of Negative Electrode)

Powder of artificial graphite used as a negative electrode active material, an aqueous dispersion of carboxymethyl cellulose sodium (concentration of carboxymethyl cellulose sodium: 1 mass %) used as a thickening agent, and an aqueous dispersion of styrene-butadiene rubber (concentration of styrene-butadiene rubber: 50 mass %) used as a binder were mixed in a water solvent to prepare a negative electrode mixture slurry. The solid content ratio of the negative electrode active material, the thickening agent, and the binder was 97.6/1.2/1.2 (mass % ratio). The slurry was uniformly applied to 20-μm-thick copper foil, followed by drying, and then the workpiece was compression-molded with a press. Thereby, a negative electrode was prepared.

(Production of Positive Electrode)

LiCoO₂ used as a positive electrode active material, acetylene black used as a conductive material, and a dispersion of polyvinylidene fluoride (PVdF) in N-methyl-2-pyrrolidone used as a binder were mixed to prepare a positive electrode mixture slurry. The solid content ratio of the positive electrode active material, the conductive material, and the binder was 92/3/5 (mass % ratio). The positive electrode mixture slurry was uniformly applied to a 20-μm-thick current collector made of aluminum foil, followed by drying, and then the workpiece was compression-molded with a press. Thereby, a positive electrode was prepared.

(Production of Lithium Ion Secondary Battery)

The above prepared negative electrode, a polyethylene separator, and the above prepared positive electrode were stacked in the given order to provide a battery element.

A bag made of a laminate film in which an aluminum sheet (thickness: 40 μm) was coated with a resin layer on each side was prepared. The above battery element was placed in the bag in such a manner that the terminals of the positive electrode and negative electrode stuck out of the bag. One of the electrolyte solutions of Examples 1 to and Comparative Examples 1 to 5 was poured into the bag and the bag was vacuum sealed. Thereby, a lithium ion secondary battery in a sheet form was produced.

<High-Temperature Cycle Capacity Retention Ratio>

The above produced secondary battery in the state of being sandwiched and pressurized between plates was subjected to constant current-constant voltage charge (hereinafter, referred to as CC/CV charge) (0.1 C cut off) to 4.4 V at a current corresponding to 0.2 C at 60° C. Then, the battery was discharged to 3 V at a constant current of 0.2 C. This process was counted as one cycle. The initial discharge capacity was determined from the discharge capacity of the third cycle. Here, 1 C means a current value required for discharging the reference capacity of a battery in an hour. For example, 0.2 C indicates a ⅕ current value thereof. The cycle was again repeated, and the discharge capacity after 100 cycles was defined as the capacity after cycles. The ratio of the discharge capacity after 100 cycles to the initial discharge capacity was determined, which was regarded as a cycle capacity retention ratio (%).

Cycle capacity retention ratio (%)=(discharge capacity after 100 cycles)/(initial discharge capacity)×100

<Resistance Increasing Rate>

A charge and discharge cycle under predetermined charge and discharge conditions (charge at 0.2 C and a predetermined voltage until the charge current reached 1/10 C, and discharge at a current corresponding to 1 C to 3.0 V) was defined as one cycle. The resistance after three cycles and the resistance after 100 cycles were determined. The measurement temperature was 25° C. The resistance increasing rate after 100 cycles was determined by the following formula.

Resistance increasing rate (%)=(resistance (Ω) after 100 cycles)/(resistance (Ω) after three cycles)×100

TABLE 1

| | Components constituting electrolyte solution | | | | | | |
|---|---|---|---|---|---|---|---|
| | Acyclic carbonate | | Cyclic carbonate | | Additive | | Cycle capacity | Resistance |
| | Structure | Mixing ratio (vol %) | Structure | Mixing ratio (vol %) | Structure | Mixing ratio (mass %) | retention ratio (%) | increasing rate (%) |
| Example 1 | Component (b) | 70 | EC | 30 | Component (F) | 2.0 | 96 | 141 |
| Example 2 | Component (b) | 70 | EC | 30 | Component (F) | 0.001 | 91 | 161 |
| Example 3 | Component (b) | 70 | EC | 30 | Component (F) | 0.01 | 93 | 155 |
| Example 4 | Component (b) | 70 | EC | 30 | Component (F) | 0.1 | 94 | 149 |
| Example 5 | Component (b) | 70 | EC | 30 | Component (F) | 0.5 | 95 | 145 |
| Example 6 | Component (b) | 70 | EC | 30 | Component (F) | 1.0 | 95 | 144 |
| Example 7 | Component (b) | 70 | EC | 30 | Component (F) | 5.0 | 94 | 139 |
| Example 8 | Component (b) | 70 | EC | 30 | Component (F) | 10.0 | 93 | 138 |
| Example 9 | Component (b) | 70 | EC | 30 | Component (F) | 13.0 | 90 | 137 |
| Example 10 | Component (a) | 70 | EC | 30 | Component (F) | 2.0 | 93 | 161 |
| Example 11 | Component (c) | 70 | EC | 30 | Component (F) | 3.0 | 94 | 148 |
| Example 12 | Component (a) | 70 | FEC | 30 | Component (F) | 2.0 | 93 | 151 |
| Example 13 | Component (b) | 70 | FEC | 30 | Component (F) | 2.5 | 95 | 148 |
| Example 14 | Component (c) | 70 | FEC | 30 | Component (F) | 2.5 | 95 | 146 |

TABLE 1-continued

| | Components constituting electrolyte solution | | | | | | Cycle capacity retention ratio (%) | Resistance increasing rate (%) |
|---|---|---|---|---|---|---|---|---|
| | Acyclic carbonate | | Cyclic carbonate | | Additive | | | |
| | Structure | Mixing ratio (vol %) | Structure | Mixing ratio (vol %) | Structure | Mixing ratio (mass %) | | |
| Example 15 | Component (a) + Component (b) | 25 + 45 | EC | 30 | Component (F) | 1.0 | 94 | 152 |
| Example 16 | Component (b) | 70 | EC + FEC | 20 + 10 | Component (F) | 2.0 | 94 | 148 |
| Example 17 | Component (b) | 50 | EC | 50 | Component (F) | 2.0 | 91 | 144 |
| Example 18 | Component (b) | 70 | EC | 30 | Component (G) | 2.0 | 93 | 147 |
| Example 19 | Component (b) | 80 | EC | 20 | Component (F) + Component (G) | 2.0 + 2.0 | 94 | 144 |
| Example 20 | Component (b) | 70 | EC | 30 | Component (H) | 2.0 | 91 | 149 |
| Comparative Example 1 | Component (b) | 70 | EC | 30 | — | — | 90 | 173 |
| Comparative Example 2 | Component (b) | 70 | EC | 30 | Component (F) | 20.0 | 74 | 204 |
| Comparative Example 3 | Component (b) | 70 | EC | 30 | Component (H) | 18.0 | 66 | 196 |
| Comparative Example 4 | Component (b) | 60 | EC + FEC | 20 + 20 | Component (G) + Component (H) | 8.0 + 8.0 | 70 | 187 |
| Comparative Example 5 | Component (b) | 60 | FEC | 40 | — | — | 91 | 178 |

The table shows that the lithium ion secondary batteries produced using the electrolyte solutions of Examples 1 to 20 had a higher cycle capacity retention ratio and a lower resistance increasing rate than the lithium ion secondary batteries produced using the electrolyte solutions of Comparative Examples 1 to 5.

Experiment 2 (Evaluation of 4.9 V Grade Lithium Battery)

Electrolyte solutions of Examples 21 to 39 and electrolyte solutions of Comparative Examples 6 to 11 were prepared as follows and lithium ion secondary batteries were produced using the resulting electrolyte solutions. The resistance increasing rates and the cycle capacity retention ratios of the respective batteries were evaluated.

(Preparation of Electrolyte Solution)

An acyclic carbonate(s) and a cyclic carbonate(s) were mixed in a ratio shown in Table 2 under dry argon atmosphere. To this solution was added dry fluoroalkyl phosphate monolithium salt in an amount shown in Table 2, and dry $LiPF_6$ was further added so as to be a concentration of 1.0 mol/L. Thereby, a non-aqueous electrolyte solution was obtained. The amount of the fluoroalkyl phosphate monolithium salt blended was expressed by mass % relative to the acyclic carbonate(s) and the cyclic carbonate(s).

The components shown in Table 2 are the same as those in Table 1.

(Production of Negative Electrode)

Powder of artificial graphite used as a negative electrode active material, an aqueous dispersion of carboxymethyl cellulose sodium (concentration of carboxymethyl cellulose sodium: 1 mass %) used as a thickening agent, and an aqueous dispersion of styrene-butadiene rubber (concentration of styrene-butadiene rubber: 50 mass %) used as a binder were mixed in a water solvent to prepare a negative electrode mixture slurry. The solid content ratio of the negative electrode active material, the thickening agent, and the binder was 97.6/1.2/1.2 (mass % ratio). The slurry was uniformly applied to 20-μm-thick copper foil, followed by drying, and then the workpiece was compression-molded with a press. Thereby, a negative electrode was prepared.

(Production of Positive Electrode)

$LiNi_{0.5}Mn_{1.5}O_4$ used as a positive electrode active material, acetylene black used as a conductive material, and a dispersion of polyvinylidene fluoride (PVdF) in N-methyl-2-pyrrolidone used as a binder were mixed to prepare a positive electrode mixture slurry. The solid content ratio of the positive electrode active material, the conductive material, and the binder was 92/3/5 (mass % ratio). The positive electrode mixture slurry was uniformly applied to a 20-μm-thick current collector made of aluminum foil, followed by drying, and then the workpiece was compression-molded with a press. Thereby, a positive electrode was prepared.

(Production of Lithium Ion Secondary Battery)

The above prepared negative electrode, a polyethylene separator, and the above prepared positive electrode were stacked in the given order to provide a battery element.

A bag made of a laminate film in which an aluminum sheet (thickness: 40 μm) was coated with a resin layer on each side was prepared. The above battery-element was placed in the bag in such a manner that the terminals of the positive electrode and negative electrode stuck out of the bag. One of the electrolyte solutions of Examples 21 to 39 and Comparative Examples 6 to 11 was poured into the bag and the bag was vacuum sealed. Thereby, a lithium ion secondary battery in a sheet form was produced.

<High-Temperature Cycle Capacity Retention Ratio>

The above produced secondary battery in the state of being sandwiched and pressurized between plates was subjected to constant current-constant voltage charge (hereinafter, referred to as CC/CV charge) (0.1 C cut off) to 4.9 V at a current corresponding to 0.2 C at 60° C. Then, the battery was discharged to 3 V at a constant current of 0.2 C. This process was counted as one cycle. The initial discharge capacity was determined from the discharge capacity of the third cycle. Here, 1 C means a current value required for discharging the reference capacity of a battery in an hour. For example, 0.2 C indicates a ⅕ current value thereof. The cycle was again repeated, and the discharge capacity after 100 cycles was defined as the capacity after cycles. The ratio of the discharge capacity after 100 cycles to the initial discharge capacity was determined, which was regarded as a cycle capacity retention ratio (%).

Cycle capacity retention ratio (%)=(discharge capacity after 100 cycles)/(initial discharge capacity)×100

<Resistance Increasing Rate>

A charge and discharge cycle under predetermined charge and discharge conditions (charge at 0.2 C and a predetermined voltage until the charge current reached 1/10 C, and discharge at a current corresponding to 1 C to 3.0 V) was defined as one cycle. The resistance after three cycles and the resistance after 100 cycles were determined. The measurement temperature was 25° C. The resistance increasing rate after 100 cycles was determined by the following formula.

Resistance increasing rate (%)=(resistance (Ω) after 100 cycles)/(resistance (Ω) after three cycles)×100

TABLE 2

| | Components constituting electrolyte solution | | | | | | Cycle capacity | Resistance |
|---|---|---|---|---|---|---|---|---|
| | Acyclic carbonate | | Cyclic carbonate | | Additive | | | |
| | Structure | Mixing ratio (vol %) | Structure | Mixing ratio (vol %) | Structure | Mixing ratio (mass %) | retention ratio (%) | increasing rate (%) |
| Example 21 | Component (d) | 60 | FEC | 40 | Component (F) | 2.0 | 92 | 154 |
| Example 22 | Component (d) | 60 | FEC | 40 | Component (F) | 0.001 | 86 | 163 |
| Example 23 | Component (d) | 60 | FEC | 40 | Component (F) | 0.01 | 88 | 159 |
| Example 24 | Component (d) | 60 | FEC | 40 | Component (F) | 0.1 | 89 | 157 |
| Example 25 | Component (d) | 60 | FEC | 40 | Component (F) | 0.5 | 90 | 156 |
| Example 26 | Component (d) | 60 | FEC | 40 | Component (F) | 1.0 | 90 | 156 |
| Example 27 | Component (d) | 60 | FEC | 40 | Component (F) | 5.0 | 89 | 150 |
| Example 28 | Component (d) | 60 | FEC | 40 | Component (F) | 10.0 | 88 | 151 |
| Example 29 | Component (d) | 60 | FEC | 40 | Component (F) | 13.0 | 85 | 153 |
| Example 30 | Component (e) | 60 | FEC | 40 | Component (F) | 2.0 | 88 | 154 |
| Example 31 | Component (d) + Component (e) | 30 + 30 | FEC | 40 | Component (F) | 3.0 | 89 | 155 |
| Example 32 | Component (d) + Component (e) | 55 + 5 | EC + FEC | 10 + 30 | Component (F) | 4.0 | 90 | 160 |
| Example 33 | Component (b) + Component (d) | 10 + 60 | FEC | 30 | Component (F) | 2.0 | 88 | 161 |
| Example 34 | Component (b) + Component (d) | 15 + 35 | FEC | 50 | Component (F) | 2.5 | 85 | 159 |
| Example 35 | Component (b) + Component (e) | 10 + 60 | FEC | 30 | Component (F) | 2.5 | 90 | 159 |
| Example 36 | Component (a) + Component (b) | 25 + 45 | EC | 30 | Component (F) | 1.0 | 89 | 161 |
| Example 37 | Component (d) | 70 | FEC | 30 | Component (G) | 2.0 | 88 | 166 |
| Example 38 | Component (d) | 80 | EC + FEC | 5 + 15 | Component (F) + Component (G) | 2.0 + 2.0 | 89 | 155 |
| Example 39 | Component (d) | 70 | FEC | 30 | Component (H) | 2.0 | 86 | 161 |
| Comparative Example 6 | Component (b) | 70 | EC | 30 | — | — | 41 | 225 |
| Comparative Example 7 | Component (d) | 60 | FEC | 40 | — | — | 81 | 165 |
| Comparative Example 8 | Component (d) | 70 | FEC | 30 | Component (H) | 18.0 | 61 | 196 |
| Comparative Example 9 | Component (d) + Component (e) | 55 + 5 | FEC | 40 | Component (F) | 20.0 | 73 | 179 |
| Comparative Example 10 | Component (b) | 60 | EC + FEC | 20 + 20 | Component (G) + Component (H) | 8.0 + 8.0 | 65 | 188 |
| Comparative Example 11 | Component (b) | 60 | FEC | 40 | — | — | 87 | 179 |

The table shows that the lithium ion secondary batteries produced using the electrolyte solutions of Examples 21 to 39 had a higher cycle capacity retention ratio and a lower resistance increasing rate than the lithium ion secondary batteries produced using the electrolyte solutions of Comparative Examples 6 to 11.

INDUSTRIAL APPLICABILITY

The electrolyte solution of the present invention can be suitably used as an electrolyte solution for electrochemical devices such as lithium ion secondary batteries.

The invention claimed is:

1. An electrolyte solution comprising:
   a solvent;
   an electrolyte salt; and
   a phosphate in an amount of 0.001 to 15 mass % relative to the solvent, the phosphate being represented by the following formula (1):

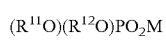

wherein $R^{11}$ and $R^{12}$ may be the same as or different from each other, and are individually represented by $Rf^{11}CH_2$—, wherein $Rf^{11}$ is a C1-C10 linear or branched fluoroalkyl group; and M is at least one selected from the group consisting of Li, Na, K, and Cs.

2. The electrolyte solution according to claim 1, wherein
   M is Li.

3. The electrolyte solution according to claim 1,
   wherein $R^{11}$ is represented by $Rf^{12}CH_2$—, where $Rf^{12}$ is a C1-C10 linear or branched fluoroalkyl group;
   $R^{12}$ is represented by $Rf^{13}CH_2$—, where $Rf^{13}$ is a C1-C10 linear or branched fluoroalkyl group;
   $Rf^{12}$ and $Rf^{13}$ are different fluoroalkyl groups; and
   M is Li.

4. The electrolyte solution according to claim 1,
   wherein the solvent comprises at least one selected from the group consisting of non-fluorinated saturated cyclic carbonates, fluorinated saturated cyclic carbonates, non-fluorinated acyclic carbonates, and fluorinated acyclic carbonates.

5. The electrolyte solution according to claim 1, wherein the electrolyte salt is at least one lithium salt selected from the group consisting of $LiPF_6$, $LiBF_4$, $LiSO_3CF_3$, $LiN(SO_2CF_3)_2$, $LiN(SO_2C_2F_5)_2$, lithium difluoro(oxalato)borate, lithium bis(oxalato)borate, and a salt represented by $LiPF_a(C_nF_{2n+1})_{6-a}$, where a is an integer of 0 to 5; and n is an integer of 1 to 6.

6. An electrochemical device comprising the electrolyte solution according to claim 1.

7. A secondary battery comprising the electrolyte solution according to claim 1.

8. A module comprising the electrochemical device according to claim 6.

9. A module comprising the secondary battery according to claim 7.

* * * * *